United States Patent
Sweeney et al.

(10) Patent No.: US 8,532,770 B2
(45) Date of Patent: Sep. 10, 2013

(54) CARDIAC MECHANICAL VIBRATION MONITOR USING INFORMATION INDICATIVE OF LEAD MOTION

(75) Inventors: Robert J. Sweeney, Woodbury, MN (US); Allan C. Shuros, St. Paul, MN (US); Krzysztof Z. Siejko, Maple Grove, MN (US); David C. Olson, Eden Prairie, MN (US); Frank Ingle, Palo Alto, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 71 days.

(21) Appl. No.: 13/168,547

(22) Filed: Jun. 24, 2011

(65) Prior Publication Data

US 2011/0319782 A1    Dec. 29, 2011

Related U.S. Application Data

(60) Provisional application No. 61/359,430, filed on Jun. 29, 2010.

(51) Int. Cl.
*A61N 1/365* (2006.01)

(52) U.S. Cl.
USPC ............................ 607/17; 607/18; 600/508

(58) Field of Classification Search
USPC .................. 607/17–18; 600/508–509
See application file for complete search history.

(56) References Cited

U.S. PATENT DOCUMENTS

| | | | |
|---|---|---|---|
| 3,012,192 A | 12/1961 | Lion | |
| 4,011,500 A | 3/1977 | Pelletier et al. | |
| 5,271,392 A | 12/1993 | Ferek-Petric | |
| 5,324,326 A | 6/1994 | Lubin | |
| 5,361,776 A | 11/1994 | Samuelson et al. | |
| 5,417,717 A | 5/1995 | Salo et al. | |
| 5,448,222 A | 9/1995 | Harman | |
| 5,554,177 A | 9/1996 | Kieval et al. | |

(Continued)

FOREIGN PATENT DOCUMENTS

| | | | |
|---|---|---|---|
| EP | 0578748 B1 | 5/1996 | |
| EP | 0670743 B1 | 12/2001 | |

(Continued)

OTHER PUBLICATIONS

U.S. Appl. No. 13/168,481, Response filed Feb. 19, 2013 to Non Final Office Action mailed Nov. 19, 2012, 11 pgs.

(Continued)

*Primary Examiner* — Rex R Holmes

(74) *Attorney, Agent, or Firm* — Schwegman Lundberg & Woessner, P.A.

(57) ABSTRACT

Systems and methods to monitor cardiac mechanical vibrations using information indicative of lead motion are described. In an example, a system including an implantable medical device can include an excitation circuit configured to provide a non-tissue stimulating, non-therapeutic electrical excitation signal to a portion of an implantable lead. A receiver circuit can be configured to obtain information indicative of a mechanical vibration of the implantable lead due at least in part to one or more of an impact of at least a portion of the heart to the implantable lead, or friction contact between the implantable lead and cardiac tissue. The system can include a processor circuit configured to determine one or more of a lead mechanical status, or information indicative of valvular activity using the information indicative of the mechanical vibration of the implantable lead.

21 Claims, 21 Drawing Sheets

(56) References Cited

U.S. PATENT DOCUMENTS

| | | | |
|---|---|---|---|
| 5,564,434 | A | 10/1996 | Halperin et al. |
| 5,693,074 | A | 12/1997 | Ferek-Petric |
| 5,694,943 | A | 12/1997 | Brewer et al. |
| 5,897,577 | A | 4/1999 | Cinbis et al. |
| 5,899,927 | A | 5/1999 | Ecker et al. |
| 6,094,981 | A | 8/2000 | Hochstein |
| 6,285,898 | B1 | 9/2001 | Ben-Haim |
| 6,317,628 | B1 | 11/2001 | Linder et al. |
| 6,445,951 | B1 | 9/2002 | Mouchawar |
| 6,591,143 | B1 | 7/2003 | Ekwall |
| 6,869,404 | B2 | 3/2005 | Schulhauser et al. |
| 6,873,870 | B2 | 3/2005 | Ferek-Petric |
| 6,980,866 | B2 | 12/2005 | Yu et al. |
| 7,025,727 | B2 | 4/2006 | Brockway et al. |
| 7,035,684 | B2 | 4/2006 | Lee |
| 7,047,083 | B2 | 5/2006 | Gunderson et al. |
| 7,248,923 | B2 | 7/2007 | Maile et al. |
| 7,689,286 | B2 | 3/2010 | Pastore et al. |
| 7,787,946 | B2 | 8/2010 | Stahman |
| 2005/0137636 | A1 | 6/2005 | Gunderson et al. |
| 2006/0282000 | A1 | 12/2006 | Zhang et al. |
| 2007/0299477 | A1 | 12/2007 | Kleckner et al. |
| 2008/0077333 | A1 | 3/2008 | Maxey et al. |
| 2008/0119750 | A1 | 5/2008 | Patangay et al. |
| 2008/0242976 | A1 | 10/2008 | Robertson et al. |
| 2008/0269820 | A1* | 10/2008 | Nilsson .................. 607/17 |
| 2009/0030334 | A1 | 1/2009 | Anderson et al. |
| 2009/0177110 | A1 | 7/2009 | Lyden et al. |
| 2009/0204163 | A1 | 8/2009 | Shuros et al. |
| 2009/0299432 | A1 | 12/2009 | Stadler et al. |
| 2010/0069768 | A1 | 3/2010 | Min et al. |
| 2010/0076279 | A1 | 3/2010 | Shuros et al. |
| 2010/0179421 | A1 | 7/2010 | Tupin |
| 2011/0319772 | A1 | 12/2011 | Ingle |
| 2011/0319776 | A1 | 12/2011 | Sweeney et al. |
| 2011/0319778 | A1 | 12/2011 | Sweeney et al. |
| 2011/0319779 | A1 | 12/2011 | Sweeney et al. |

FOREIGN PATENT DOCUMENTS

| | | |
|---|---|---|
| EP | 1469910 B1 | 12/2006 |
| EP | 1515770 B1 | 6/2009 |
| WO | WO-9503086 A2 | 2/1995 |
| WO | WO-9527531 A1 | 10/1995 |
| WO | WO-2004103458 A2 | 12/2004 |
| WO | WO-2005089638 A1 | 9/2005 |
| WO | WO-2008054261 A1 | 5/2008 |
| WO | WO-2009058638 A1 | 5/2009 |
| WO | WO-2010033190 A2 | 3/2010 |
| WO | WO-2012005985 A2 | 1/2012 |
| WO | WO-2012005985 A3 | 1/2012 |
| WO | WO-2012005987 A2 | 1/2012 |
| WO | WO-2012005987 A3 | 1/2012 |
| WO | WO-2012005988 A2 | 1/2012 |
| WO | WO-2012005988 A3 | 1/2012 |
| WO | WO-2012005989 A2 | 1/2012 |
| WO | WO-2012005989 A3 | 1/2012 |
| WO | WO-2012005991 A2 | 1/2012 |
| WO | WO-2012005991 A3 | 1/2012 |

OTHER PUBLICATIONS

U.S. Appl. No. 13/168,481, Examiner Interview Summary mailed Feb. 26, 2013, 3 pgs.
U.S. Appl. No. 13/168,481, Non Final Office Action mailed Nov. 19, 2012, 5 pgs.
U.S. Appl. No. 13/168,481, Notice of Allowance mailed Mar. 5, 2013, 5 pgs.
U.S. Appl. No. 13/168,507, Response filed Mar. 21, 2013 to Non Final Office Action mailed Dec. 21, 2012, 14 pgs.
U.S. Appl. No. 13/168,507, Non Final Office Action mailed Dec. 21, 2012, 10 pgs.
U.S. Appl. No. 13/168,531, Response filed Jan. 8, 2013 to Restriction Requirement mailed Dec. 21, 2012, 9 pgs.
U.S. Appl. No. 13/168,531, Restriction Requirement mailed Dec. 21, 2012, 6 pgs.
International Application Serial No. PCT/US2011/041834, International Preliminary Report on Patentability mailed Jan. 17, 2013, 7 pgs.
International Application Serial No. PCT/US2011/041834, International Search Report mailed Jan. 26, 2012, 3 pgs.
International Application Serial No. PCT/US2011/041834, International Written Opinion mailed Jan. 26, 2012, 5 pgs.
International Application Serial No. PCT/US2011/041850, International Preliminary Report on Patentability mailed Jan. 17, 2013, 7 pgs.
International Application Serial No. PCT/US2011/041850, International Search Report mailed Feb. 1, 2012, 4 pgs.
International Application Serial No. PCT/US2011/041850, International Written Opinion mailed Feb. 1, 2012, 5 pgs.
International Application Serial No. PCT/US2011/041854, International Preliminary Report on Patentability mailed Jan. 17, 2013, 6 pgs.
International Application Serial No. PCT/US2011/041854, International Search Report Mailed Jan. 26, 2012, 4 pgs.
International Application Serial No. PCT/US2011/041854, International Written Opinion Mailed Jan. 26, 2012, 4 pgs.
International Application Serial No. PCT/US2011/041860, International Preliminary Report on Patentability mailed Jan. 17, 2013, 7 pgs.
International Application Serial No. PCT/US2011/041868, International Preliminary Report on Patentability mailed Jan. 17, 2013, 7 pgs.
International Application Serial No. PCT/US2011/041868, International Search Report mailed Jan. 26, 2012, 4 pgs.
International Application Serial No. PCT/US2011/041868, International Written Opinion mailed Jan. 26, 2012, 5 pgs.
International Serial No. PCT/US2011/041860, International Search Report Jan. 26, 2012, 4 pgs.
International Serial No. PCT/US2011/041860, International Written Opinion mailed Jan. 26, 2012, 5 pgs.
"Japanese Name Application Serial No. [Pending], Voluntary Amendment filed Dec. 27, 2012", With English Claims, 49 pgs.
"Lion's Twin-T Circuit Revisited", IEEE Engineering in Medicine and Biology, (Sep. 1992), 61-66.
Brusich, Sandro, et al., "Cardiac Lead Used as Contractility Sensor: Animal Study", HRS 2011, Innovators Poster Session—Esplanade Foyer Moscone South, (May 6, 2011), 7 pgs.

* cited by examiner

CARDIAC MECHANICAL VIBRATION MONITOR USING INFORMATION INDICATIVE OF LEAD MOTION

CLAIM OF PRIORITY

This patent application claims the benefit of priority, under 35 U.S.C. Section 119(e), to Ingle U.S. Provisional Patent Application Ser. No. 61/359,430, entitled "Lead Motion Sensing Using Cable Microphonics," filed on Jun. 29, 2010, which is hereby incorporated by reference herein in its entirety.

CROSS REFERENCE TO RELATED APPLICATIONS

This patent application is related to:
(1) U.S. patent application Ser. No. 13/168,481;
(2) U.S. patent application Ser. No. 13/168,507; and
(3) U.S. patent application Ser. No. 13/168,531; each of which is hereby incorporated herein by reference in its respective entirety.

BACKGROUND

An ambulatory medical device, such as an implantable medical device (IMD), can be configured for implant in a subject, such as a patient. An IMD can be configured to be coupled to a patient's heart such as via one or more implantable leads. Such an IMD can obtain diagnostic information or generate therapy to be provided to the patient, such as via the coupled implantable lead. Examples of such devices can include cardiac function management (CFM) devices including one or more of implantable pacemakers, implantable cardioverter-defibrillators (ICDs), cardiac resynchronization therapy devices (CRTs), or one or more other devices. Such devices can include one or more electrodes coupled, such as via the implantable lead, to circuitry located on or within the IMD. Such circuitry can be configured to monitor electrical activity, such as to obtain information indicative of electrical activity of the heart.

A cardiac electrotherapy device to measure cardiac contractions using an elongated lead body that forms a high frequency transmission line is mentioned in U.S. Pat. No. 5,693,074 entitled "Cardiac Electrotherapy Device for Cardiac Contraction Measurement."

A time domain reflectometry impedance sensor for measuring body impedance along a lead or catheter implanted in a patient's cardiovascular system is mentioned in U.S. Pat. No. 5,361,776 entitled "Time Domain Reflectometer Impedance Sensor Method of Use and Implantable Cardiac Stimulator Using Same."

Overview

Generally, an IMD can obtain information indicative of cardiac activity such as by monitoring cardiac electrical signals obtained via an implantable lead tethered to the IMD, or by monitoring an electrical signal indicative of the motion of the implantable lead. An implantable lead can be positioned to include a distal end within the right ventricle, such as crossing an opening of the tricuspid valve. During diastole, the heart tissue is relaxes opening the atrioventricular valves so that blood can flow into the atria and the ventricle. With depolarization, the atria contract providing an "atrial kick" of blood volume into the ventricles. During a ventricular contraction, the atrioventricular valves close, preventing blood from flowing back into the atria.

The present inventors have recognized, among other things, that mechanical information indicative of cardiac, blood, or vascular motion can be detected using the motion of one or more conductors electrically coupled to an ambulatory device, such as an IMD. Such information can be used by the IMD in one or more of determining a lead mechanical status or determining information indicative of valvular activity. In an example the information indicative of valvular activity can be used for at least one of detecting heart sounds, detecting dissynchrony between the right and left sides of the heart, or guiding a cardiac resynchronization therapy (CRT). For example, the present inventors have also recognized that an implantable lead electrically and mechanically tethered to the IMD can provide information indicative of the motion of the lead, such as using one or more electrical measurements as described in the following examples, such as to detect cardiac, blood, or vascular motion. Such information indicative of motion can be used to adjust therapy timing or other therapy parameters, to obtain information about the effectiveness of a cardiac therapy (e.g., electrostimulation), or to diagnose one or more cardiac conditions. The present inventors have also recognized, among other things, that such information can be obtained via measurement of variation in electrical parameters corresponding to the motion of one or more therapy-conducting or activity-sensing conductors located on or within the lead assembly, without requiring a dedicated mechanical or acceleration sensor incorporated into the lead assembly.

Cardiac mechanical vibration can be monitored via lead motion. In an example, a system including an implantable medical device can include an excitation circuit configured to provide a non-tissue stimulating, non-therapeutic electrical excitation signal, including a first range of frequencies, to a conductor comprising a portion of an implantable lead. The system can include a receiver circuit configured to be electrically coupled to the conductor and to obtain information indicative of a mechanical vibration of the implantable lead due at least in part to one or more of an impact of at least a portion of the heart to the implantable lead, or frictional contact between the implantable lead and cardiac tissue. The system can include a processor circuit configured to determine one or more of a lead mechanical status, or information indicative of valvular activity using the information indicative of the mechanical vibration of the implantable lead.

Example 1 can include subject matter (such as a system, a method, a means for performing acts, or a machine-readable medium including instructions that, when performed by the machine, cause the machine to perform acts, etc.) that can include an implantable medical device (IMD) that can include (1) an excitation circuit configured to provide a non-tissue stimulating, non-therapeutic electrical excitation signal to a conductor comprising a portion of an implantable lead, the signal comprising a time-varying signal including a first range of frequencies, (2) a receiver circuit configured to obtain, in response to the excitation signal, information indicative of a mechanical vibration of the implantable lead due at least in part to one or more of impact of at least a portion of the heart to the implantable lead or friction between the implantable lead and cardiac tissue, and (3) a processor circuit configured to determine one or more of a lead mechanical status, or information indicative of valvular activity, using the information indicative of the mechanical vibration of the implantable lead.

In Example 2, the subject matter of Example 1 can optionally be configured such that the processor circuit can determine a lead mechanical status using the information indicative of the mechanical vibration of the implantable lead.

In Example 3, the subject matter of Examples 1 or 2 can optionally be configured such that the processor circuit can determine information indicative of valvular activity using the information indicative of the mechanical vibration of the implantable lead.

In Example 4, the subject matter of Examples 1-3 can optionally be configured such that the processor can obtain frequency components including or above an audio frequency range, the frequency components including energy corresponding to impact or frictional contact of the implantable lead with at least a portion of the heart.

In Example 5, the subject matter of Examples 1-4 can optionally be configured such that the processor can determine a lead mechanical status including one or more of lead fault information or lead maturity information.

In Example 6, the subject matter of Examples 1-5 can optionally be configured such that the lead fault information can include a lead dislodgement indication, including information indicative of a partial dislodgement or information indicative of a full dislodgement, that can be determined at least in part using the information indicative of the mechanical vibration of the implantable lead, such as to determine information about a connection of the implantable lead to at least a portion of the heart.

In Example 7, the subject matter of Examples 1-6 can optionally be configured such that the information indicative of valvular activity can include information indicative of a mechanical vibration of a heart valve, the mechanical vibration coupled to the implantable lead when the implantable lead is located within or near the heart.

In Example 8, the subject matter of Examples 1-7 can optionally be configured such that the mechanical vibration of the heart valve comprises information indicative of a valve impacting an implantable lead within the heart, including information indicative of at least one of valve closure, or valve opening.

In Example 9, the subject mater of Examples 1-8 can optionally be configured to include a heart sound sensing circuit, wherein the heart sound sensing circuit can be configured to determine heart sound information using the information indicative of the mechanical vibration of a heart valve.

In Example 10, the subject matter of Examples 1-9 can optionally be configured such that the heart sound sensing circuit can determine heart sound information using information indicative of radial compression of at least a portion of the implantable lead, the compression correlative to blood pressure.

In Example 11, the subject matter of Examples 1-10 can optionally be configured to include an implantable lead configured to be located within or near the heart, wherein the implantable lead can include a piezoelectric acoustic transducer. The piezoelectric acoustic transducer can be configured to receive acoustic information indicative of the movement of the implantable lead, such as including information indicative of the mechanical vibration of the implantable lead, and the piezoelectric acoustic transducer can be coupled to a conductor included in the implantable lead.

In Example 12, the subject matter of Examples 1-11 can optionally be configured to include a conductor comprising a portion of the implantable lead, wherein the conductor can include one or more of a cardiac therapy delivery conductor or a cardiac electrical activity sensing conductor, wherein the conductor can be configured to be coupled to an implantable electrode included as a portion of the implantable lead.

In Example 13, the subject matter of Examples 1-12 can optionally be configured such that the information indicative of the mechanical vibration of the implantable lead can include one or more of magnitude information, or phase information, corresponding to one or more frequencies included in the first range of frequencies, the magnitude information, or phase information, determined at least in part using an electrical response signal provided by the implantable lead in response to the excitation signal and the movement or mechanical vibration of the implantable lead.

In Example 14, the subject matter of Examples 1-13 can optionally be configured such that one or more of the magnitude information, or the phase information, can include a time-varying portion corresponding to the movement or mechanical vibration of the implantable lead.

In Example 15, the subject matter of Examples 1-14 can optionally be configured to include the implantable lead, including the conductor, wherein the implantable lead can be located within or near the heart.

Example 16 can include, or can be combined with the subject matter of one or any combination of Examples 1-15 to optionally include, subject matter (such as an apparatus, a method, a means for performing acts, or a machine-readable medium including instructions that, when performed by the machine, cause the machine to (1) provide a non-tissue stimulating, non-therapeutic electrical excitation signal to a conductor comprising a portion of an implantable lead, the signal comprising a time-varying signal including a first range of frequencies, (2) obtain, in response to the excitation signal, information indicative of a mechanical vibration of the implantable lead due at least in part to one or more of impact of at least a portion of the heart with the implantable lead or friction between the implantable lead and cardiac tissue, and (3) determine one or more of a lead mechanical status, or information indicative of valvular activity using the information indicative of the mechanical vibration of the implantable lead.

In Example 17, the subject matter of Example 16 can optionally include instructions that, when executed by the processor, cause the processor to obtain frequency components including or above an audio frequency range, wherein the frequency components can include energy corresponding to impact or frictional contact of the implantable lead with at least a portion of the heart.

In Example 18, the subject matter of Examples 16 or 17 can optionally include instructions that, when executed by the processor, cause the processor to determine the lead mechanical status, and can optionally include instructions to determine one or more of lead fault information or lead maturity information.

In Example 19, the subject matter of any one or any combination of Examples 16-18 can optionally include instructions, when executed by the processor, cause the processor to determine heart sound information using the information indicative of the mechanical vibration of the implantable lead, such as including information indicative of the mechanical vibration of a heart valve.

In Example 20, the subject matter of any one or any combination of Examples 16-19 can optionally include instructions, when executed by the processor, cause the processor to use information indicative radial compression on at least a portion of the implantable lead, wherein the compression can correspond to a blood pressure when the implantable lead is located in or near a blood vessel.

Example 21 can include subject matter, or can be combined with the subject matter of one or any combination of Examples 1-20, (such as a system, a method, a means for performing acts, or a machine-readable medium including instructions that, when performed by the machine, cause the machine to perform acts, etc.) that can include (1) a means for providing a non-tissue stimulating, non-therapeutic electrical excitation signal to a conductor comprising a portion of an implantable lead, the signal comprising a time-varying signal including a first range of frequencies, (2) a means for obtaining, in response to the excitation signal, information indicative of a mechanical vibration of the implantable lead due at least in part to one or more of impact of at least a portion of the heart with the implantable lead or friction between the implantable lead and cardiac tissue, and (3) a means for detecting one or more of a lead mechanical status, or information indicative of valvular activity using the information indicative of the mechanical vibration of the implantable lead.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventors have recognized, among other things, that mechanical information indicative of cardiac, blood, or vascular motion can be detected such as by using a motion of one or more conductors electrically coupled to an ambulatory device, such as one or more conductors included as a portion of an implantable lead coupled to an IMD. Such information can be used, such as by the IMD or other device, in one or more of detecting a change to cardiovascular health, monitoring the effectiveness of a generated therapy, or guiding therapy. Information indicative of the motion of the implantable lead can be used, in addition to, or instead of sensed cardiac electrical activity.

For example, an implantable lead electrically and mechanically tethered to the IMD can provide information indicative of the motion of the lead, such as using one or more electrical measurements as described in the following examples. Such information indicative of the motion of the implantable lead can be used to adjust therapy parameters (e.g., one or more of therapy timing, a therapy delivery location, one or more therapy energy levels, etc.), or to obtain information about the effectiveness of a cardiac therapy (e.g., electrostimulation). Such monitored mechanical information can be used to obtain diagnostic information about one or more cardiac conditions or diseases. The present inventors have recognized, among other things, that such information can be obtained via measurement of variation in electrical parameters correlative to the motion of one or more therapy-conducting or activity-sensing conductors located on or within the lead assembly, without requiring a dedicated mechanical or acceleration sensor incorporated into the lead assembly.

Figure 1:
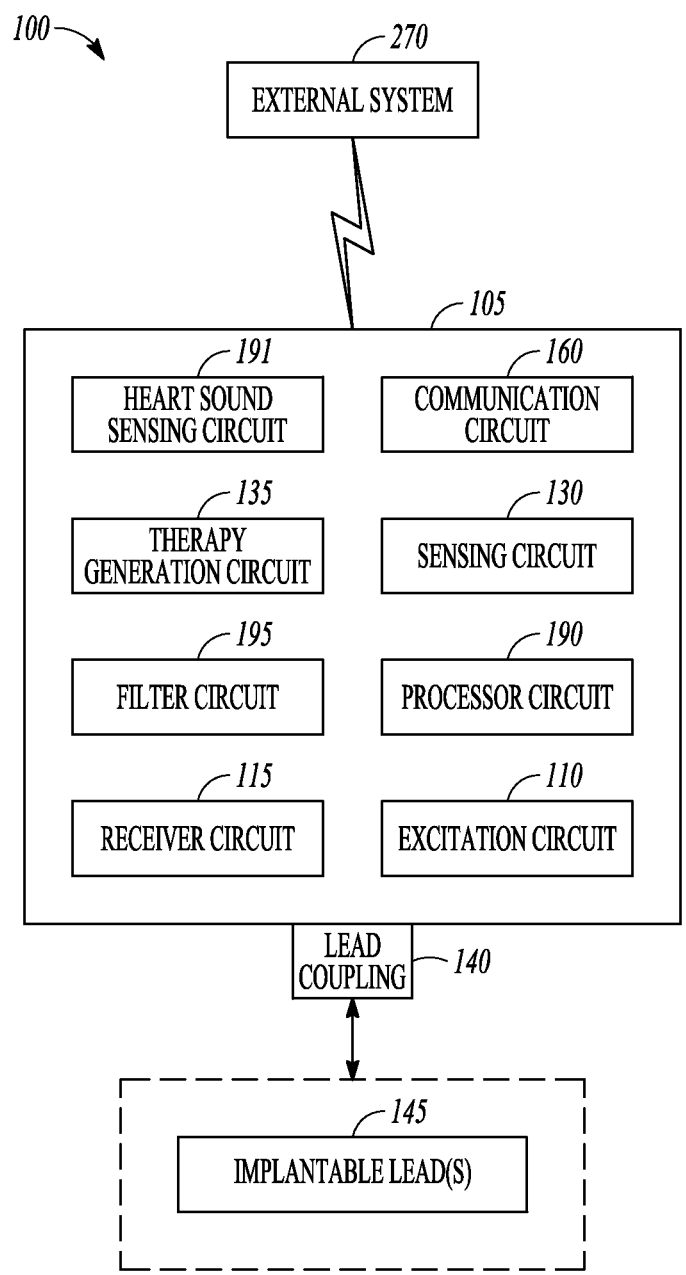
FIG. 1 illustrates generally an example of a portion of an ambulatory system that can analyze information indicative of the movement of an implantable lead.

FIG. 1 illustrates generally an example of a portion of a system 100 that can be used for analyzing information indicative of the movement of an implantable lead. The ambulatory system 100 can include an ambulatory medical device, such as the implantable medical device (IMD) 105. The IMD 105 that can include an excitation circuit 110, a receiver circuit 115, a sensing circuit 130, a therapy generation circuit 135, a heart sound sensing circuit 191, a communication circuit 160, a processor circuit 190, and a filter circuit 195. In an example, the IMD 105 can include an interconnection, such as the lead coupling 140, configured to electrically couple the IMD 105 to one or more implantable leads, such as the implantable lead 145. In an example, the IMD 105 can be communicatively coupled to an external system 270, such as by using a communicative coupling 187 (e.g., an inductive or electromagnetic telemetry link, an acoustic link, an optical link, a wired connection, etc.).

One or more of the excitation circuit 110, the receiver circuit 115, the sensing circuit 130, the therapy generation circuit 135, the heart sound sensing circuit 191, the communication circuit 160, the processor circuit 190, or the filter circuit 195 can be realized on or within a commonly shared substrate, such as on a commonly-shared integrated circuit, module, circuit board, or the like. In an example, one or more of the circuits of FIG. 1 can be included in one or more separate assemblies or a separate ambulatory device, such as using one or more wired or wireless communication techniques to exchange information between such devices.

In an example, the IMD 105 can include a communication circuit 160, such as to permit wired or wireless communication using the communicative coupling 187 such as to an external system 270. The external system 270 can include a monitoring device (e.g., a local monitoring device, or a remotely located monitoring device, etc.), an ambulatory sensor, a non-ambulatory sensor, or a programmer. In an example, a sensor included with the external system 270 can include a sensing circuit (e.g., an external ECG sensor) such as configured to provide a signal indicative of cardiac electrical activity (e.g., at least a portion of a surface ecg).

The system 100 can include processing capability, such as included within the IMD 105, or included in a portion of the external system 270, such as the monitoring device, the ambulatory sensor, or the non-ambulatory sensor. Thus, various techniques can be implemented at one or more of such locations, such as on-board the IMD 105 or at one or more externally located processor, either located locally (e.g., within a programmer, or local monitoring device) or at a more remote location (e.g., within a remote monitoring system.) In an example, one or more portions of various techniques can be distributed between such locations.

For example, the IMD 105 can include processing capability, such as the processor circuit 190. For example, the various techniques can be implemented such as using an application-specific integrated circuit (ASIC) configured to perform one or more functions, or a general-purpose circuit programmed to perform such functions. Such a general-purpose circuit can include a microprocessor, a microcontroller, or a programmable logic circuit, or a portion of one or more of these. In an example, the IMD 105 can include a processor-readable medium such as a memory circuit (e.g., an EEPROM, an SRAM, or one or more other memory technology devices). The processor circuit 190 can be configured to perform one or more instructions stored on the processor-readable medium. Such processing techniques can be performed within the IMD 105, or within a device included in the external system 270.

In an example, the IMD 105 can include an excitation circuit (e.g., the excitation circuit 110) that can be coupled to at least one of the receiver circuit 115 or the implantable lead 145. The excitation circuit 110 can be configured to provide a time varying signal including a first range of frequencies such as including a non-tissue stimulating, non-therapeutic electrical excitation signal, such as for coupling to the implantable lead 145. In an example, the excitation signal can include a time-varying voltage or current including one or more frequencies within a specified frequency range (e.g., a range from about 10 KHz to about 5 MHz, from about 5 MHz to about 30 MHz, from about 30 MHz to about 150 MHz, or including one or more other ranges of frequencies). In an example, the excitation signal can include a pulsed electrical signal, such as including one or more current or voltage pulses including a specified or desired amplitude, duration, pulse repetition rate, duty cycle, or morphology, among other parameters.

In an example, the excitation circuit 110 can be coupled to one or more implantable leads, such as the implantable lead 145 via the lead coupling 140. The lead coupling 140 can include a header or other connector included as a portion, part, or component of the IMD 105. In an example, an impedance measurement can be made at least in part using the excitation circuit 110, such as to obtain the information indicative of lead motion. The impedance measurement can include injecting a current between a first terminal such as at least a portion of the lead coupling 140 and one or more other conductive elements, such as the housing of the IMD 105 or a second terminal, and measuring the voltage developed across the respective conductive elements, or vice versa. In an example, a synchronous current injection and voltage measurement can be used, such as discussed in relation to the physiologic impedance measurement techniques of the commonly assigned U.S. patent application Ser. No. 12/350,728, entitled "IMPEDANCE MEASUREMENT AND DEMODULATION USING IMPLANTABLE DEVICE," filed on Jan. 8, 2009, which is herein incorporated by reference in its entirety, including its description of injecting one or more non-tissue-stimulating bi-phasic current pulses and synchronously measuring the voltage induced by the one or more bi-phasic current pulses.

In an example, the implantable lead 145 can be coupled to circuitry within the IMD 105 such as via the lead coupling 140 (e.g., a header or other connector block included as a portion of the IMD 105). For example, the implantable lead 145 can include one or more conductors (e.g., a cardiac therapy delivery conductor, a cardiac electrical activity sensing conductor, etc.) that can provide electrical coupling between one or more electrodes located at or near tissue (e.g., cardiac tissue, neural tissue, etc.) and the IMD 105. In an example, the implantable lead 145 can be located at a site within or on the body (e.g., including one or more surface, subcutaneous, or intravascularly-located electrodes or conductors).

In an example, the receiver circuit 115 can be electrically or communicatively coupled to an implantable lead 145 such as through the lead coupling 140. For example, one or more separate conductors in the implantable lead 145 can be attached to one or more terminal blocks such as included in a lead coupling 140 attached to a housing of the IMD 105. For example, the lead coupling 140 can provide electrical contact between one or more conductors of the implantable lead 145 and circuitry within the IMD 105 (e.g., excitation circuit 110, the receiver circuit 115, the therapy generation circuit 135, etc.). In an example, the receiver circuit 115 can be configured to receive a response signal, such as including a signal indicative of the motion of the implantable lead, hereinafter referred to as a lead motion indicating (LMI) signal. For example, a response signal can be obtained in response to an interaction between an excitation signal, such as provided by the excitation circuit 110, and the electrical characteristics of the implantable lead 145 (e.g., one or more motion-dependent passive electrical characteristics of the lead) such as during a movement of the implantable lead 145. For example, such electrical characteristics of the lead can vary as portions of the lead are compressed or flexed (e.g., such as due to bending, torsion, frictional contact, impact, radial compression, etc.), such as altering the spacing between portions of one or more conductors included in the lead assembly. In an example, the receiver circuit 115 can be configured to receive or process one or more response signals obtained from one or more implantable leads 145 concurrently with or subsequently to the excitation circuit 110 providing the excitation signal to the one or more implantable leads. For example, the receiver circuit 115 can be configured to receive magnitude information or phase information corresponding to one or more frequencies included in a range of frequencies provided in the excitation signal. In an example, the magnitude information or the phase information can include time-varying information indicative of the movement of the implantable lead 145.

For example, the receiver circuit 115 can be configured to obtain information about the movement of a first implantable lead located (e.g., a first LMI signal), such as located within or near a first location of the heart using a first response signal obtained from the first implantable lead. Additionally, the receiver circuit 115 can be configured to obtain information about the movement of a second implantable lead (e.g., a second LMI signal), such as located within or near a second location of the heart, using a second response signal obtained from the second implantable lead. For example, the information about the movement of an implantable lead can be determined or extracted from the LMI signal (e.g., using information about an amplitude, a frequency, a phase, a noise floor, a signal-to-noise ratio, a duration between peaks or other features, a waveform morphology or shape, or one or more other characteristics of the LMI signal).

In an example, the receiver circuit 115 can be configured to process the response signal (e.g., using a filter), such as to provide a time-varying signal indicative of the motion of the implantable lead (e.g., the LMI signal) for analysis. For example, the response signal can include a first component (e.g., a carrier signal), such as including information about the excitation signal, and a second component (e.g., a signal indicative of lead motion that can modulate the carrier), such as the LMI signal. In an example, the LMI signal can include time-varying information indicative of the motion of the implantable lead. In an example, the receiver circuit 115 can be configured to transfer at least a portion of the LMI signal to a circuit configured for signal processing (e.g., processor circuit 190, etc.) to be analyzed. For example, the processor circuit 190 can analyze at least a portion of the LMI signal such as to obtain information indicative of the motion of the implantable lead such that can contain information about a cardiac mechanical contraction (e.g., a mechanical contraction waveform, a mechanical vibration waveform, etc.).

In an example, the receiver circuit 115 can be configured to determine amplitude information of one or more LMI signals. For example, the amplitude information can be determined such as by using one or more of a central tendency (e.g., an average, a median, a mean, etc.), a peak-to-peak determination, a peak determination, a root-mean-square determination, a relative indication of information about a portion of the LMI signal (e.g., a percentage of an absolute or local maximum or minimum), or an absolute value of at least a portion of the LMI signal. In an example, the receiver circuit 115 can be configured to analyze at least a portion of the LMI signal, such as to compare amplitude information obtained from the LMI signal to a criterion (e.g., a threshold) or to amplitude information corresponding to a second LMI signal. The receiver circuit 115 can use such an analysis to determine whether the LMI signal can be sent for further analysis, such as by the processor circuit 190.

In an example, the IMD 105 can include a filter circuit 195 such as communicatively coupled to one or more of the receiver circuit 115 or the processor circuit 190. In an example, the filter circuit 195 can be configured to provide an LMI signal, including a mechanical vibration waveform, from the response signal. For example, the filter circuit 195 can provide the mechanical vibration waveform such as by using a high-pass filter configured to pass frequencies over a specified frequency (e.g., above about 10 Hz) such that the processor circuit 190 can provide information indicative of mechanical vibration of the mechanical lead. The high-pass filter can be configured to provide a mechanical vibration waveform over a specified frequency range, such as including an audio frequency range (e.g., from about 10 Hz to about 20 KHz). The mechanical vibration waveform can include information about frictional contact (e.g., between about 100 Hz to about 1 KHz) or valvular contact (e.g., above about 1 KHz) between at least a portion of the heart and the implantable lead 145.

In an example, the mechanical vibration waveform can include vibrational information (e.g., information corresponding to a change in blood pressure, blood flow, regurgitation or other factors), such as can be associated with heart sounds. The heart produces mechanical vibrations as it progresses through a cardiac cycle. Such mechanical vibration can correspond to a number of factors, including one or more of a change in blood pressure, a change in blood flow, the opening and closing of the heart valves, regurgitation of blood past a heart valve, etc. Occurring in a characteristic sequence, the heart sound are referred to as the first heart sound (S1), the second heart sound (S2), the third heart sound (S3) and the fourth heart sound (S4). For example, S1 can be indicative of the maximum rate of change of pressure in the left ventricle during a cardiac cycle. In an example, the heart sounds can be coupled to a portion of the implantable lead, with the lead structure acting as a mechanical-to-electrical transducer. For example, mechanical vibrations coupled to the implantable lead can result in an LMI signal that can include information indicative of one or more heart sounds S1, S2, S3, or S4, or other events in or near the heart.

In an example, the filter circuit 195 can be configured to provide an LMI signal (e.g., a mechanical contraction waveform) from the response signal. For example, the filter circuit 195 can provide the LMI signal such as by using a band-pass filter over a specified frequency range (e.g., from about 0.5 Hz to about 10 Hz) such that the processor circuit 190 can provide information indicative of the motion of the implantable lead. For example, a band-pass filter such as configured to pass frequencies between about 0.5 Hz and about 2 Hz can be used to provide a mechanical contraction waveform (e.g., a signal, a time-series, or other information) indicative of the mechanical contraction of the heart. The mechanical contraction waveform can be conditioned such that the waveform approaches zero amplitude when averaged (e.g., reducing or removing a DC-offset) or can approach zero during an interval of no motion. Although band-pass and high-pass filters are generally described, any combination of analog or digital filters can be used, including a one or more high-pass filters, low-pass filters, notch filters, passive filters (e.g., having "T" sections, "π" sections, "L" sections, etc.), active filters (e.g., Bessel filter, Chebyshev filter, Butterworth filter, etc.), IIR filters, FIR filters, or the like.

In an example, the IMD 105, can include a processor circuit, such as the processor circuit 190, configured to be communicatively coupled to one or more of the excitation circuit 110, the receiver circuit 115, the sensing circuit 130, the therapy generation circuit 135, or the filter circuit 195. In an example, the processor circuit 190 can be configured such as to determine information about cardiac function, such as including information about valvular activity, or determine information about the mechanical status of the implantable lead 145 over one or more cardiac contraction cycles.

In an example, the processor circuit 190 can be configured to receive information indicative of the motion of an implantable lead, such as an LMI signal, from one or more of the receiver circuit 115 or the filter circuit 195. In an example, the processor circuit 190 can be configured to receive a signal indicative of cardiac electrical activity, such as from the sensing circuit 130 or a sensor included in the external system 270 (e.g., an ambulatory sensor or a non-ambulatory sensor). The processor circuit 190 can be configured to determine whether a cardiac mechanical contraction occurred during a specified interval, such as included in at least a portion of the LMI signal, such as a mechanical cardiac waveform or a mechanical vibration waveform. In an example, the processor circuit 190 can be configured to determine a relationship between an indication of cardiac electrical activity and an indication of cardiac mechanical motion, such as determined using at least a portion of an LMI signal and a portion of the signal indicative of cardiac electrical activity. For example, the processor circuit 190 can be configured to determine one or more of a lead mechanical status or information indicative of valvular activity using the information indicative of the vibration of the mechanical lead. The processor circuit 190 or the heart sound sensing circuit 191 can be configured to determine heart sound information using the information indicative of valvular activity, information indicative of cardiac electrical activity, or acoustic information.

Movement of the implantable lead 145 can include a physical displacement of one or more portions of the implantable lead 145, such as with respect to an equilibrium position. In an illustrative example, the implantable lead 145 can undergo a physical displacement, such as from a mechanical coupling to, or physical contact with, moving tissue. In an example, the information indicative of movement of the implantable lead 145 can include a time varying signal (e.g., the LMI signal), where the LMI signal corresponds to a movement of the heart (e.g., a cardiac contraction cycle, an impact of a heart valve to the implantable lead 145, a frictional contact of cardiac tissue to the implantable lead 145, or mechanical contact of the lead to vibrating tissue, etc.).

In an example, the processor circuit 190 can be configured to obtain the mechanical contraction waveform or the mechanical vibration waveform at least in part by using one or more filters, such as using the filter circuit 195. In an example, the processor circuit 190 can be configured such as to obtain the mechanical contraction waveform or the mechanical vibration waveform indicative of the mechanical motion of at least a portion of a heart (e.g., one or more of the tricuspid valve, the right atrium, the left atrium, the right ventricle, or the left ventricle). For example, the response signal, such as obtained by the receiver circuit 115, can be filtered using a band-pass filter configured to pass frequencies within a specified frequency range (e.g., between about 0.05 Hz and about 10 Hz), or using a high-pass filter configured to pass frequencies, such as within an audible frequency range, (e.g., over about 10 Hz), such as discussed below with FIGS. 8 and 12. In an example, the processor circuit 190 can be configured to analyze the mechanical contraction waveform or the mechanical vibration waveform continuously over one or more cardiac contraction cycles. In an example, the processor circuit 190 can be configured to analyze a specified duration of lead motion information including one or more mechanical contractions, such as a specified duration of contraction information or a specified duration of vibrational information obtained at a specified interval (e.g., once a minute, hourly, daily, weekly, etc.), or obtained following a specified event (e.g., a user initiated event, an occurrence of a physiological event, or in response to one or more other criteria).

In an example, the processor circuit 190 can obtain a composite LMI signal, such as by using a mixer circuit. Such composite LMI signals can include information about a motion originating in or detected nearby an atrial region, a motion originating in or detected nearby a ventricular region, other motion of the implantable lead independent of the motion of the heart, or a vibration such as due to a valve impact against a region of the lead. For example, the mixer circuit can combine one or more LMI signals additively, such as to provide a composite LMI signal having information about atrial and ventricular contractions. In an example, the mixer circuit can be configured to combine at least a portion of two or more LMI signals such as to provide a mechanical contraction waveform primarily associated with ventricular motion or primarily associated with atrial motion.

Figure 8:
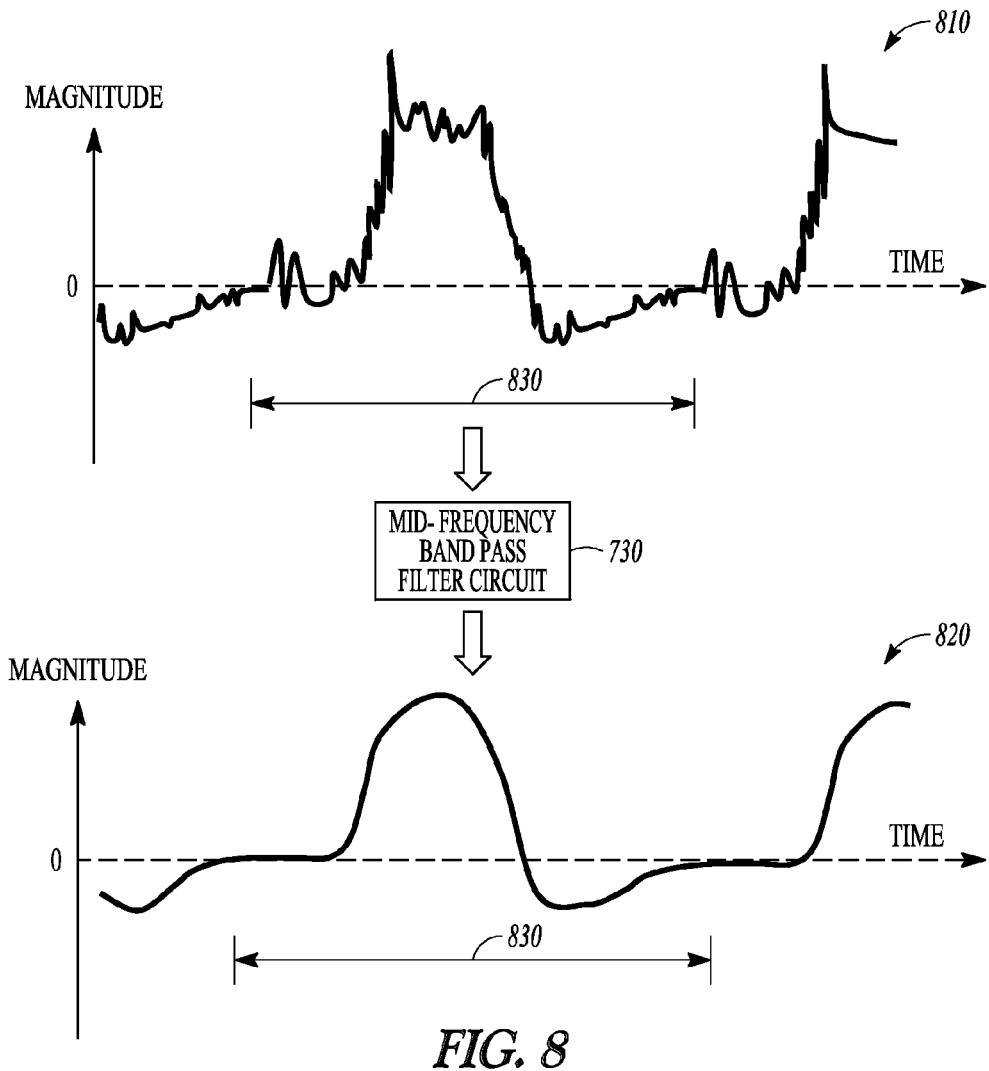
FIG. 8 illustrates generally an illustrative example that can include filtering or otherwise conditioning a response signal.
Figure 12:
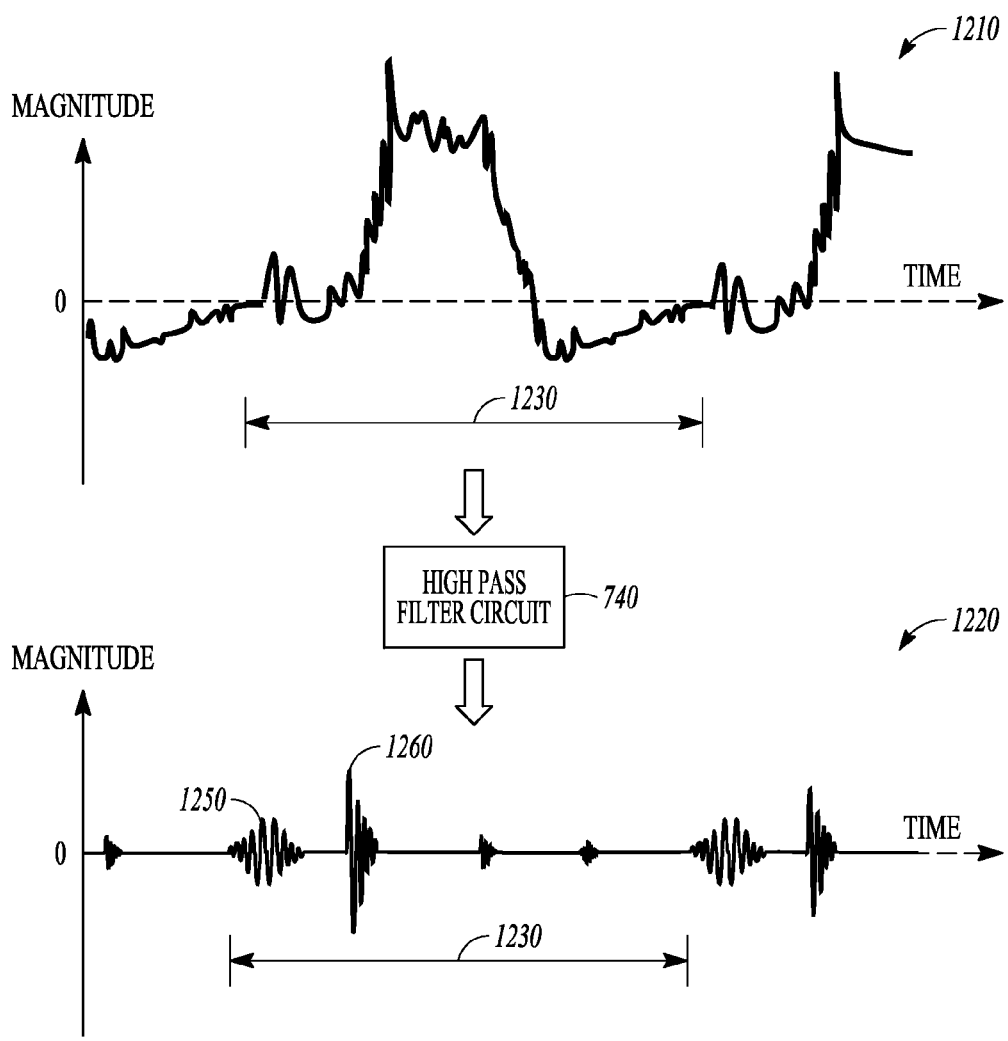
FIG. 12 illustrates generally an illustrative example that can include filtering or otherwise conditioning a response signal.

In an example, the processor circuit 190 can be configured to obtain electrical activity information such as using a signal indicative of cardiac electrical activity over one or more cardiac contraction cycles (e.g., from the sensing circuit 130 or from an ambulatory or non-ambulatory sensor such as included in the external network 270). For example, the electrical activity information can include an electrical signal as can be represented by an electrogram over at least a portion of one or more cardiac contraction cycles. In an example, the processor circuit 190 can be configured to obtain mechanical motion information about the heart, such as from an LMI signal (e.g. a mechanical contraction waveform or a mechanical vibration waveform) over the one or more cardiac contraction cycles (e.g., from the receiver circuit 115, or the filter circuit 195). For example, the mechanical motion information can include at least a portion of one or more mechanical contraction waveforms as shown in FIGS. 8 and 12.

In an example, a subject can have one or more implantable leads (e.g., a right ventricular (RV) lead, a right atrial (RA) lead, or a left ventricular (LV) lead) located within or near the heart, as discussed below with FIG. 2. The implantable leads can enter the right atrium via the superior vena cava, where at least a portion of the implantable lead remains. For example, the distal end of the RA lead can be affixed to at least one location of the epicardium (e.g., using fixed tines, a retractable helix, etc.). The RV lead can be disposed within the heart such that the lead passes from the SVC, through the right atrium, and into the right ventricle via the tricuspid valve, such as including a distal tip at or near the apical region of the right ventricle. The LV lead can be disposed such that the lead is routed to a location near the left ventricle via the coronary sinus, from the right atrial region, such that the distal end of the LV lead is located in a coronary vein located near the left ventricle.

During the cardiac contraction cycle, the atrioventricular valves (e.g., the tricuspid and mitral valves) open during myocardial relaxation such as to provide blood to the ventricles. During a ventricular contraction, the atrioventricular valves close due to the increase in pressure and blood is expelled through the pulmonary and aortic valves. The first heart sound, S1, can correspond in part to the turbulent blood flow resulting from the blood flow stopping at the closure of the atrioventricular valves.

In an example, the processor circuit 190 can be configured to analyze information indicative of a mechanical vibration of the implantable lead 145. The mechanical vibration can be due at least in part to one or more of an impact of at least a portion of the heart to the implantable lead, frictional contact between at least a portion of the heart to the implantable lead 145, frictional contact between a portion of two or more implantable leads, or an impact of at least a portion of a first implantable lead and a second implantable lead. In an example, the RV lead can be impacted by the tricuspid valve as the valve closes during systole. In an example, an impact to the implantable lead 145 can result in a deformation or compression to at least a portion of the implantable lead 145. The deformation or compression can cause a transitory change of the electrical characteristics of the implantable lead resulting in an electrical signature (e.g., a waveform) indicative of the mechanical vibration. For example, over a specified frequency range (e.g., from about 100 Hz to about 1 KHz), the mechanical vibration waveform can include a damped oscillating vibration waveform having a peak deflection followed by a number of damped peaks. Over a second specified frequency range (e.g., over 1 KHz), the mechanical vibration waveform can correspond to an impulse indicative of the impact of the valve to the implantable lead 145. In an example, the closure of the tricuspid valve can cause frictional contact between a portion of the heart (e.g., the tricuspid valve or a portion of the endocardium) and the implantable lead 145. For example, the frictional contact can correspond to a transitory oscillating waveform corresponding to the frictional contact between the heart and a portion of the implantable lead 145. In an example, the cardiac contraction can cause a first implantable lead to make transitory contact to a second implantable lead, such as an impact or frictional contact between the first and the second implantable leads.

In an example, amplitude information of the mechanical vibration waveform can be determined such as by using one or more of a central tendency (e.g., an average, a median, a mean, etc.), a peak-to-peak determination, a peak determination, a root-mean-square determination, a statistical ranking (e.g., a percentile), or an absolute value of at least a portion of the LMI signal. For example, the amplitude information (e.g., the peak determination, peak-to-peak determination, etc.) of the damped oscillating waveform, or the impulse signal can correspond to the forcefulness of the tricuspid valve closure. For example, a high rate of change to the blood pressure during systole (e.g., dP/dt) can result in a forceful closure of the tricuspid valve and a corresponding peak magnitude of the mechanical vibration waveform. Similarly, a less forceful tricuspid valve closure (e.g., a peak determination of less than a baseline or a waveform feature duration of less than a baseline) can correspond to a change in the physiological condition of the subject including one or more of a reduced dP/dt, a leaky tricuspid valve, or valvular stenosis.

In an example, the processor circuit 190 can use the information indicative of a mechanical vibration of the implantable lead 145 such as to determine a lead mechanical status, including at least one of a lead "maturity" indication, a lead dislodgement indication, or a lead fracture indication. Generally, a newly implanted lead can move relative to the heart during a cardiac contraction cycle, anchored at one or more locations (e.g., using tines, a helical screw, or other techniques to securing the implantable lead 145 to the endocardium). Over time, the mechanical placement and electrical behavior of the implantable lead becomes generally less variable (e.g., the lead "matures"). For example, the implantable lead 145 can become mechanically anchored such as via tissue ingrowth or endothelialization, securely coupling the lead assembly to a portion of the heart (e.g., endocardium or epicardium). Fibrous tissue growth can provide a secure mechanical connection between the implantable lead 145 and the heart tissue. Such secure anchoring can provide a more repeatable or less variable mechanical vibration waveform representative of movement of at least a portion of the heart.

During a mechanical contraction, the implantable lead 145 can experience frictional contact to a portion of the heart or another implantable lead. During the "maturation" process, the connection of the implantable lead 145 to a portion of the heart gradually becomes more stable such that the frictional content of the mechanical vibration waveform can be reduced or can otherwise vary in an observable manner. For example, the frictional contact to the implantable lead 145 can be included in a mechanical vibration waveform, such as a frictional portion corresponding to a specified frequency range (e.g., about an audio frequency range or from about 100 Hz to about 1 KHz), or via time-gating a portion of the mechanical contraction waveform.

Once the lead has "matured," the frictional contact content of the mechanical vibration waveform can be reduced or eliminated. For example, the implantable lead 145 can be said to have "matured" once a measure of the frictional content of the mechanical contraction waveform meets a specified criterion, (e.g., exceeds a threshold, lies within or outside a specified range, etc.) The baseline value can be obtained such as by using a metric (e.g., a peak determination, a peak-to-peak determination, a central tendency, a duration, etc.) of the frictional content of the mechanical vibration waveform at the time of implantation, or over a specified duration near the time of implantation. In an example, the processor 190 can deem the implantable lead 145 to have matured when the measure of the frictional content is less than a specified maturity threshold.

In an example, the processor 190 can determine a lead mechanical status corresponding to lead dislodgement. As discussed above, the implantable lead 145 can be said to have "matured" once the fibrous tissue growth have stabilized the movement of the implantable lead such as to meet the specified criterion, such as a maturity threshold. However, an implantable lead may occasionally become dislodged from the connective tissue resulting from the tissue ingrowth or the point of fixation (e.g., partial dislodgement), or both (full dislodgement). For example, dislodgement, either full or partial, can be an indication of a mechanically damaged or compromised lead (e.g., including a fracture, a compression, an abrasion, etc.) or has been moved from the desired site of implantation. For example, clavicular compression of the lead can damage the lead mechanically, or the lead can be dislodged by persistent rotation of the IMD 105 in the subcutaneous tissue pocket by the patient (e.g., "twiddler's syndrome).

Figure 13A:
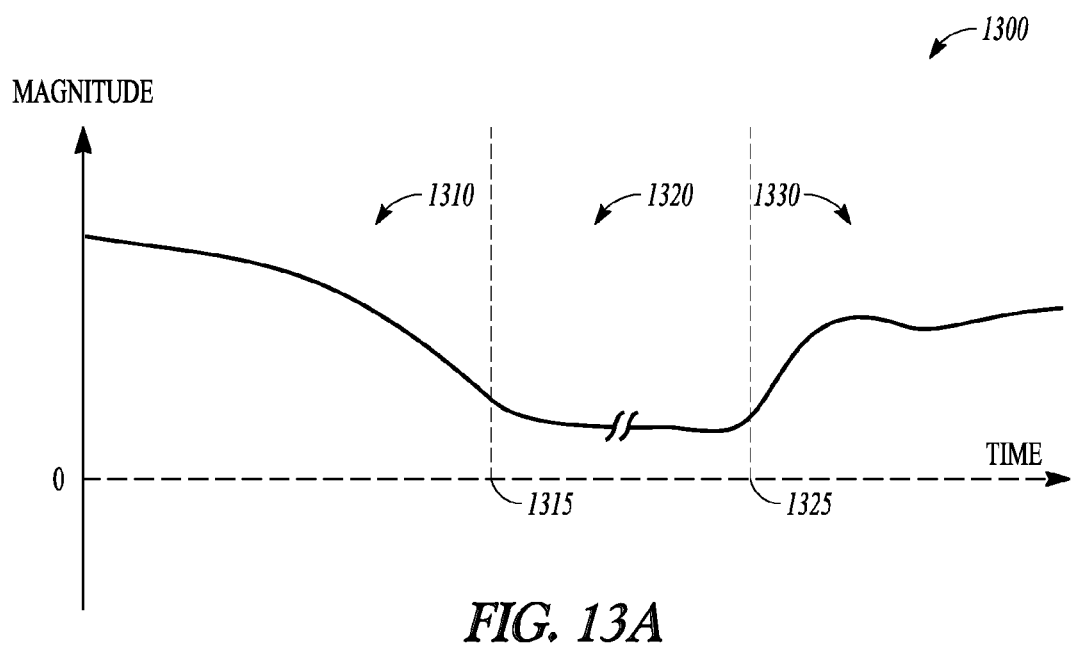
FIGS. 13A-13B illustrate generally an illustrative example information indicative of a change to a lead status.

The processor 190 can be configured to determine a lead mechanical status corresponding to lead dislodgement such as by comparing a first indication of lead maturity to a second indication of lead maturity, where the comparison meets a lead dislodgement criterion, as illustrated in the example of FIG. 13A. The lead dislodgement criterion can include a threshold, a specified range of values, or can vary as a function of one or more characteristics of the LMI signal or a physiological signal. For example, the first indication of lead maturity can correspond to a metric of the mechanical vibration waveform measured over time, such as a central tendency of the frictional portion of the waveform (e.g., an average) over a specified long duration (e.g., a day, a week, a month, etc.). The second indication of lead maturity can be determined over a second (e.g., shorter) duration, such as over an hour or a day.

In an example, the processor circuit 190 can determine an indication of partial lead dislodgement when the comparison of the first and second indications of lead maturity meets a criterion, such as exceeding a partial lead dislodgement threshold. In an example, the lead dislodgement threshold can be the same as or different from the lead maturity threshold. In an example, the processor circuit 190 can determine an indication of full lead dislodgement, such as when the comparison value exceeds a range of values up to or including the lead maturity baseline value, such as the maturity threshold.

Figure 6:
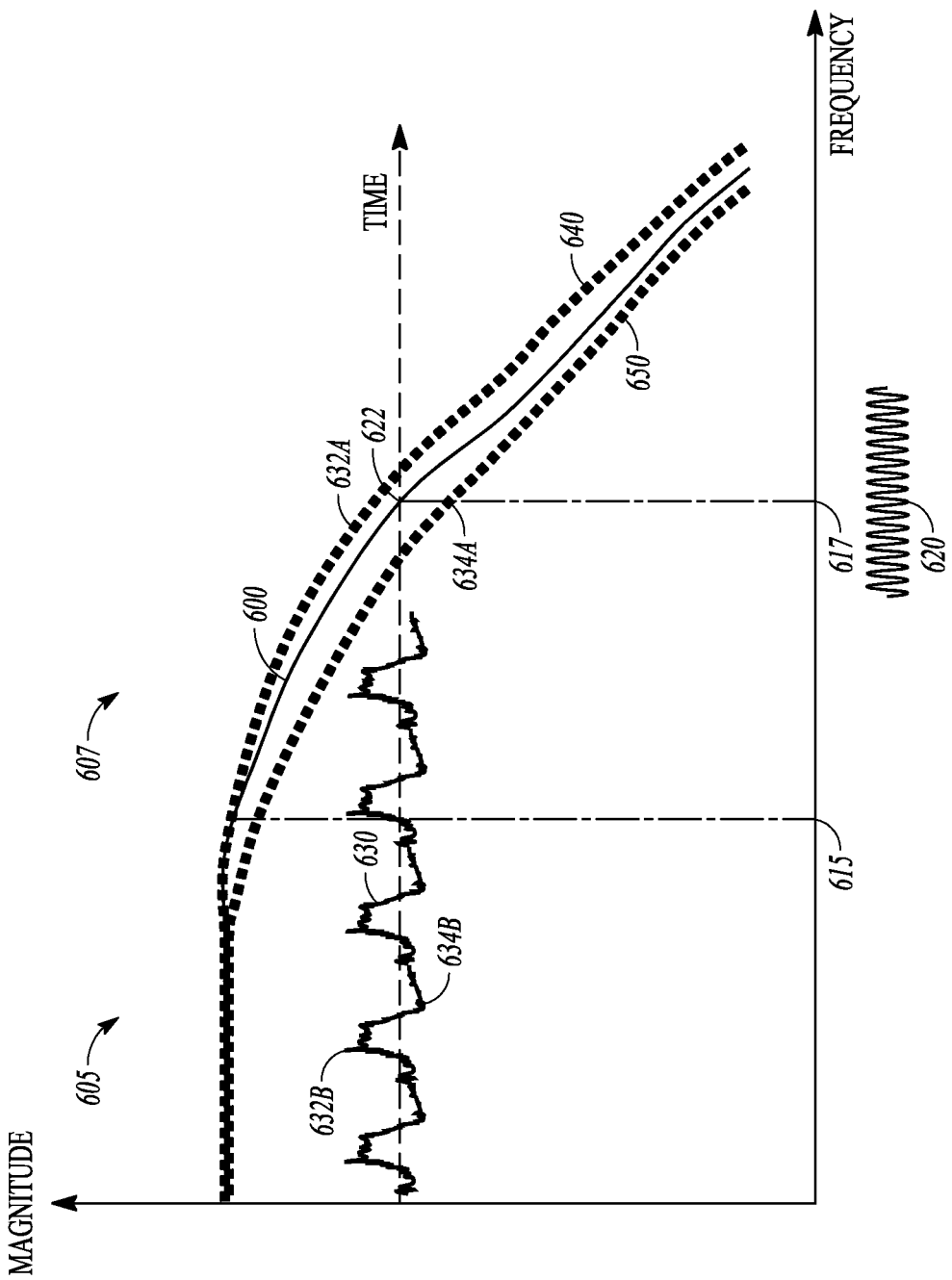
FIG. 6 illustrates generally an illustrative example of a relationship between a magnitude of a response signal vs. frequency.

In an example, the lead mechanical status can include a lead integrity indication. For example, the electrical characteristics of the implantable lead 145, as discussed in FIGS. 3 and 6, can change over time as the implantable lead 145 ages. For example, the processor circuit 190 can monitor the frequency characteristics, as shown in FIG. 6, over time to determine an indication of a lead failure. For example, a sudden change or slow drift in the magnitude of the response signal at a specified frequency (e.g., 30 MHz) can indicate a lead failure. In an example, the processor circuit 190 can be configured to determine a lead integrity characteristic (e.g., an LMI magnitude at a specified frequency, a central tendency of LMI magnitudes at the specified frequency over a specified duration, etc.) for the implantable lead 145 at occasional, or periodic intervals (e.g., hourly, daily, weekly, etc.) and store the result in memory. The processor circuit 190 can determine an indication of lead failure (e.g., fracture, aging, etc.) by comparing a current lead integrity characteristic to a previous lead integrity characteristic. In an example, a lead failure indication can be determined such as when the difference between the current lead integrity characteristic and a baseline lead integrity characteristic (e.g., a characteristic determined at or near a time of known lead integrity such as implantation) meets a specified criterion (e.g., exceeds a threshold, lies within or outside a specified or desired range, etc.).

In an example, the lead integrity indication can correspond to a transient response, such as from an intermittent failure such as due to a lead fracture. For example, the movement of the implantable lead during a cardiac contraction cycle (e.g., gross mechanical movement, an impact, frictional contact, etc.) can cause an intermittent electrical connection within at least a portion of the implantable lead 145. In an example, a rise time corresponding to a contraction metric such as an average magnitude over a current duration can indicate a lead fracture (e.g., an impulse over a short duration).

In an example, the processor circuit 190, or the heart sound sensing circuit 191 can be configured such as to use at least one of the mechanical vibration information, radial compression of the implantable lead due to blood pressure, the mechanical contraction information or a physiological signal such as an indication of cardiac electrical activity or a waveform indicative of heart sounds. For example, at least a portion of the heart sounds can be associated with the closure of the atrioventricular valves, or the semilunar valves (e.g., the aortic or the pulmonary valves). In an example, physiological information, (e.g., heart sounds, posture, etc.) can be derived using a relationship between valve closures. For example, the heart sounds (e.g., S1 or S2) can be "split," such as can be associated with delay between the closure of the aortic an pulmonary valve, or between the mitral and tricuspid valves. For example, S2 can be "split" due to a right bundle branch block, resulting in delayed pulmonic valve closing. Left bundle branch block may cause the aortic valve to close slower than the pulmonary valve. If, for example, the tricuspid valve closes after the Mitral valve, then S1 can be associated with a right bundle branch block.

In an example, an indication of an impact to the implantable lead, such as described above in reference to the tricuspid valve, can correspond to an indication of S1. In an example, the audible heart sounds can be transmitted such as using a mechanical vibration waveform. In an example, a metric, such as a signal magnitude of the mechanical vibration waveform can be used by the heart sound sensing circuit 191 such as to determine amplitude and timing of the heart sounds. Heart sounds sensed using the mechanical vibration waveform or the microphonic transmission of the heart sounds using the implantable lead can allow greater accuracy in identifying heart sound amplitudes and timing than audible heart sounds sensed externally from the subject.

In an example, the processor circuit 190 can be configured to determine a trend associated with the lead mechanical status using one or more lead mechanical vibration metrics. Data trending can be performed using various forms of regression analysis, such as a linear regression, a non-linear regression, a least-squares technique, a Bayesian technique, a quintile regression, or a nonparametric regression, or using one or more other techniques.

In an example, the system 100 can include the sensing circuit 130, such as to obtain a signal indicative of cardiac electrical activity. For example, the obtained signal can be used to provide a graphical representation of the cardiac electrical activity, such as an intracardiac electrogram or a surface ecg. In an example, the IMD 105 can be configured to detect a cardiac condition (e.g. an arrhythmia) or therapy effectiveness (e.g., cardiac capture following a electrostimulation pulse), such as using signal information (e.g., magnitude or interval information) detected using the sensing circuit 130, such as magnitude or interval information from the signal representative of cardiac electrical activity. For example, the processor circuit 190 can be configured to use electrogram timing information, such as a time interval obtained between successive atrial contractions, ventricular contractions, or between an atrial contraction and a ventricular contraction.

In an example, the timing information can be compared to a criterion, such as to detect or classify an indication of an arrhythmia when the criterion has been met (e.g., exceeding a threshold, lying within or outside of a specified range, etc.). In an example, the timing information can include a timing reference corresponding to a magnitude meeting a specified criterion. For example, the timing reference can include a duration (e.g., such as a duration during which a magnitude exceeds a value or remains within a specified range of values), or a fiducial (e.g., such as a time associated with a magnitude crossing a specified threshold). For example, the criterion (e.g., the specified range of values, or the specified threshold) can vary automatically, such as by using automatic gain control. In an example, the criterion can vary based on one or more physiological conditions, such as detected using the signal information (e.g., a magnitude or timing information of a signal indicative of cardiac electrical activity).

In an example, the IMD 105 can be configured to generate an electrostimulation, such as using one or more of a pacing or a cardiac resynchronization therapy (CRT) circuit (e.g., the therapy generation circuit 135). Such a therapy generation circuit 135 can be configured to generate bradycardia pacing or a resynchronization electrostimulation therapy for delivery to cardiac tissue, or one or more other therapies. In an example, the therapy generation circuit 135 can include a neural stimulator device, such as to provide electrical, mechanical, optical, acoustic or chemical stimulation to one or more neural targets.

In an example, the therapy generation circuit 135 can include one or more of: a pacing circuit, an anti-tachyarrhythmia therapy circuit, a cardiac resynchronization therapy circuit, a cardiac contractility modulation (CCM) circuit, or one or more other therapy generation circuits. For example, the anti-tachyarrhythmia therapy circuit can include a defibrillation circuit, or an anti-tachyarrhythmia pacing (ATP) circuit, or the like. In an example, the therapy generation circuit 135 can be configured to determine a therapy, or therapy protocol, such as to guide an arrhythmia therapy.

In an example, the therapy generation circuit 135 can be configured to withhold generation of a therapy such as when an arrhythmia condition is not present. In an example, the therapy generation circuit 135 can be configured to withhold, or delay, generation of an arrhythmia therapy, such as when a rhythm, such as a detected arrhythmia, has been determined to be supraventricular in origin.

In an example, the therapy generation circuit 135, or the processor circuit 190, can be configured to automatically adjust one or more of an electrostimulation pulse width, an electrostimulation pulse amplitude, or a timing of delivery of electrostimulation therapy. For example, the processor circuit 190 can be configured to monitor the mechanical contraction waveform after the therapy generation circuit 135 generating a therapy to the heart (e.g., pacing energy). In response to information obtained while monitoring the therapy, the processor circuit 190 can determine information corresponding to the effectiveness of the delivered therapy (e.g., captured the myocardium, achieved fusion or another specified timing relationship between paced ventricular activation relative to an intrinsic atrial beat, or improved cardiac synchrony via CRT).

Figure 2:
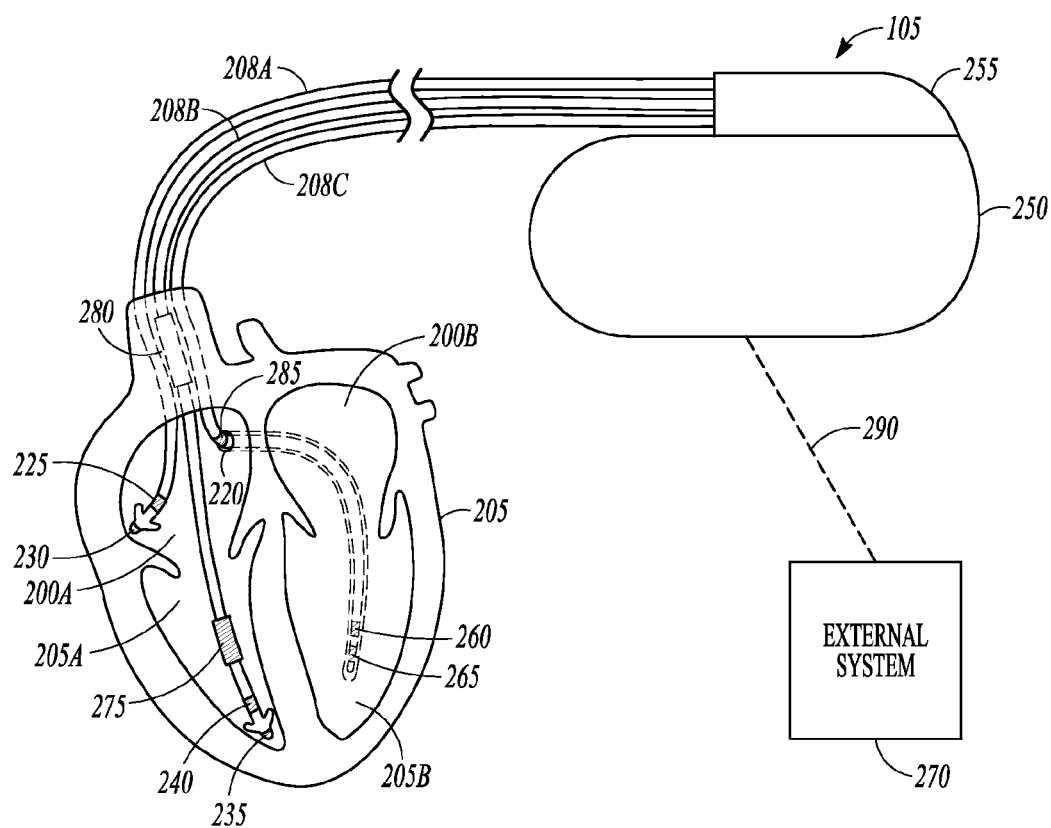
FIG. 2 illustrates generally a portion of a system that can include an implantable medical device.

FIG. 2 illustrates generally a portion of a system that can include an IMD 105. Examples of the IMD 105 can include cardiac function management (CFM) devices such as including one or more of implantable pacemakers, implantable cardioverter-defibrillators (ICDs), cardiac resynchronization therapy devices (CRTs), or one or more other devices. The system can include an IMD programmer or other external system 270, such as a local monitoring device, capable of communicating wirelessly, via communicative coupling 290, with the IMD 105, using a communication or computer network, radio frequency (RF) signals, or other telemetry capabilities. In an example, a remote monitoring device can be communicatively coupled, such as via a communication or computer network, to a remote monitoring device, such as at a remote location away from the local monitoring device (e.g., a central server, a caregiver workstation, etc.).

The IMD 105 can be coupled via one or more leads 208A-C to the heart 205. Cardiac leads 208A-C (e.g., the implantable lead 145) can include a proximal end coupled to the IMD 105 and a distal end, capable of being electrically coupled by one or more electrodes to one or more portions of the heart 205. The electrodes can deliver cardioversion, defibrillation, pacing, or resynchronization therapy, or combinations thereof, such as from the therapy generation circuit 135, to one or more chamber of the heart 205. The electrodes can be electrically coupled to sense amplifiers configured to receive electrical signals indicative of cardiac activity, such as the sensing circuit 130.

The heart 205 includes a right atrium 200A, a left atrium 200B, a right ventricle 205A, a left ventricle 205B, and a coronary sinus 220 extending from the right atrium 200A. The atrial lead 208A can include electrodes (e.g., electrical contacts, such as a ring electrode 225 or a tip electrode 230, etc.) capable of being disposed in the atrium 100A of the heart 205, such as for sensing signals, delivering pacing therapy, or both, to the atrium 200A.

The ventricular lead 208B can include one or more electrodes, such as the tip electrode 235 or the ring electrode 240, such as for sensing cardiac electrical activity, delivering pacing therapy, or both. The lead 208B can include additional electrodes, such as for delivering atrial cardioversion, atrial defibrillation, ventricular cardioversion, ventricular defibrillation, or combinations thereof to the heart 205. Such electrodes can have larger surface areas than do pacing electrodes, such as to accommodate defibrillation energy or to provide a specified or desired current density in a specified region of the heart. In an example, the lead 208B can deliver resynchronization therapy to the heart 205.

The IMD 105 can include a third cardiac lead 208C capable of being attached to the IMD 105 through the header 255. The third cardiac lead 208C can include one or more electrodes such as electrodes 260 and 265, such as placed in a coronary vein nearby the left ventricle (LV) 205B. The third cardiac lead 208C can include a ring electrode 285, such as positioned near the coronary sinus (CS) 220.

The lead 208B can include one or more of a first defibrillation coil electrode 275, such as located near the tip and ring electrodes 235, 240, such as for placement in a right ventricle (RV), or a second defibrillation coil electrode 280, such as located proximal to the first defibrillation coil 275, the tip electrode 235, and the ring electrode 240, such as for placement in or near the superior vena cava (SVC). In an example, a cardioversion or a shock therapy can be delivered from the first coil (e.g., the RV coil 275) to the second coil (e.g., the SVC coil 280). In an example, the SVC coil 280 can be electrically tied to an electrode formed on a hermetically-sealed IMD housing 250 ("can"), such as to provide an adjustable defibrillation "vector" or "pathway" for energy to pass between the RV coil 275 and the housing 250 via the myocardium. In an example, the therapy can be delivered from the RV coil 275, such as only to the electrode formed on the IMD can 250. The present methods and systems can be adjustably configured to provide one or more pacing or defibrillation therapies across specified electrode configurations, such as using information about electrical or mechanical cardiac activity as described in the examples above and below.

Figure 3:
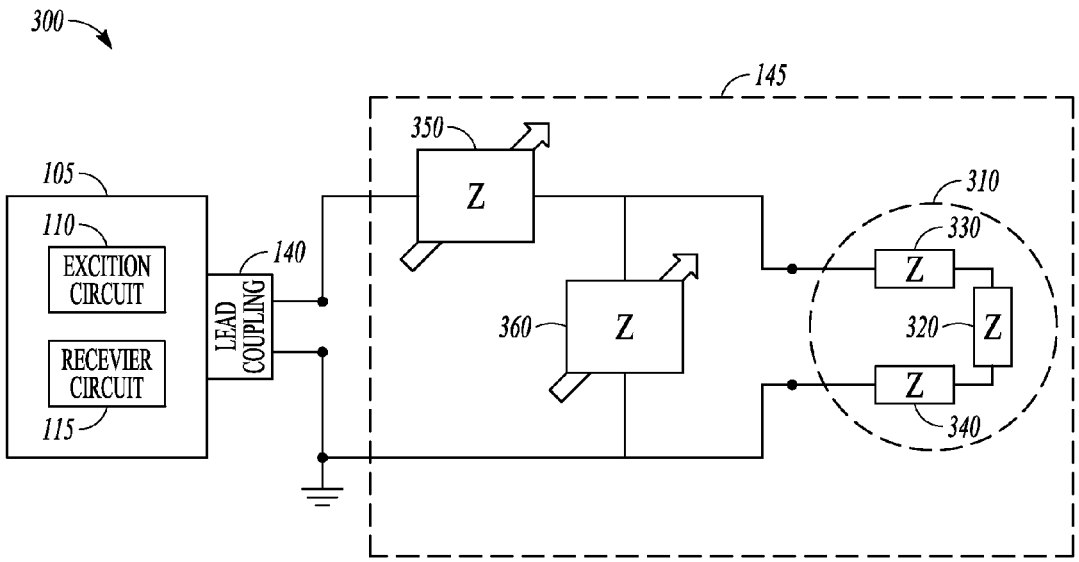
FIG. 3 illustrates generally a portion of a system that can include detecting information indicative of the movement of the implantable lead.

FIG. 3 illustrates generally a portion of a system 300 that can include detecting information indicative of the movement of one or more implantable leads, such as the implantable lead 145. In an example, the system 300 can include an IMD 105, and the implantable lead 145, such as configured to provide a therapy (e.g., an arrhythmia therapy) to a heart 205, to sense a physiological signal associated with a subject (e.g., an electrogram), or both. In an example, the IMD 105 can include the excitation circuit 110 and the receiver circuit 115, and the lead coupling 140 as described above. In an example, the implantable lead 145 can be configured to be implanted within a subject such that a distal end of the lead body 310 can be located within or near the heart 205 (e.g., at a tissue interface location), and a proximal end can be configured to be electrically coupled to the IMD 105 (e.g., at the lead coupling 140), such as to provide a therapy, to sense a physiological signal, or both. In an example, the excitation circuit 110 can be configured to provide an excitation signal to the implantable lead 145. Such an excitation signal can interact with the electrical characteristics of the implantable lead such as to provide a response signal, as can be obtained by the receiver circuit 115.

In an example, the implantable lead 145 can include one or more conductors (e.g., filers), such as one or more filers that spiral or otherwise traverse the length of the lead, such as from a connector at the proximal end of the lead to one or more electrodes along the lead or near the distal end. In an example, a lead body can be represented as a combination of resistive, capacitive, and inductive elements. In an example, the electrical characteristics of the implantable lead can be represented, such as using lead body impedance (e.g., lead impedance 350-360) and the distal end of the lead can be modeled, such as using one or more of an electrode impedance 330-340, a cardiac tissue interface impedance 320, or the like. In an example, the impedance 330-360 can represent the electrical characteristics of various lead portions (e.g., passive electrical characteristics such as the resistance of a filer, an inductance of a loop formed by one or more filers, a capacitance between one or more filers, etc.) over a specified frequency range. In an example, the tissue interface impedance can include electrode impedance, such as a characteristic impedance of an electrode, and an impedance 320 at the tissue interface, such as an impedance corresponding to a connection of the implantable lead to the cardiac tissue.

In an example, the frequency dependent components of the impedances 320-360 can vary over a specified frequency range (e.g., from about 10 KHz to about 30 MHz, from about 30 MHz to about 150 MHz, etc.), corresponding to one or more of capacitive or inductive coupling between two or more portions of the implantable lead 145. In an example, an implantable lead can include an active element, such as an accelerometer, or piezoelectric elements, that can be used to obtain information about the motion of the implantable lead 145 separately from, or additionally to the passive electric characteristics.

In an example, the electrical characteristics of the implantable lead can vary as a function of frequency, such as shown in FIG. 6, over a specified frequency range (e.g., from about 10 KHz to about 100 KHz, from about 10 KHz to about 30 MHz, from about 10 MHz to about 150 MHz, etc.), such as a result of the capacitive or inductive interaction between a conductive portion of the lead and another conductor either located within the lead or elsewhere. In an example, the implantable lead 145 can be physically connected to the heart 205, or physically located near or within the heart 205, such that movement of the heart (e.g., a cardiac contraction cycle) can result in movement of the lead body. Such movement of the lead body can cause a corresponding change to the electrical characteristics (e.g., lead capacitance, lead inductance, etc.).

For example, the lead impedances 350-360 can vary as a function of time corresponding to the movement of the implantable lead, such as during a cardiac cycle. Lead motion can include movement, or physical manipulation, of the implantable lead due to motion, such as caused by a cardiac contraction cycle (e.g., bending, stretching, twisting, impact, torsion, compression, friction, etc.). In an example, the motion of the implantable lead 145 can include physical disturbance to the lead due to impact (e.g., a heart valve impact), frictional movement (e.g., frictional contact to cardiac tissue, or other tissue), radial compression (e.g., such as due to variation in blood pressure), or the like. In an example, lead motion can include, physical translation, or rotation of the lead body relative to a point fixed in space (e.g., a point on the body, inertial frame, etc.), such as might be measurable with a lead based accelerometer.

Figure 4A:
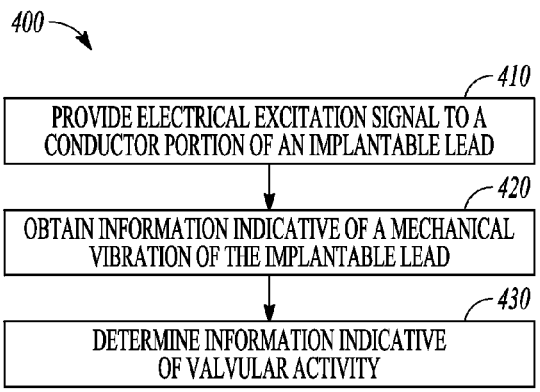
FIGS. 4A-4B illustrate generally examples of techniques that can include analyzing information indicative of a vibration of the implantable lead.
Figure 9:
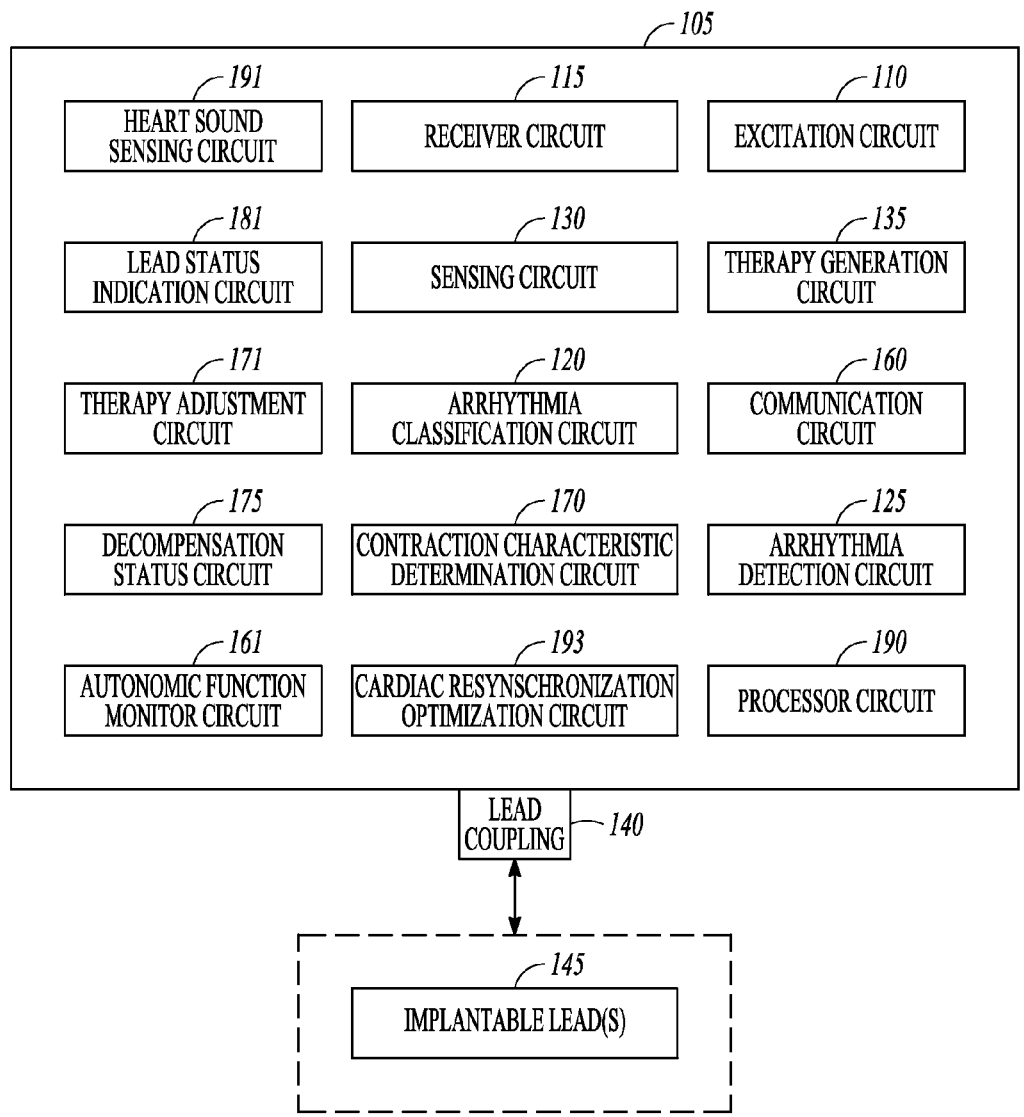
FIG. 9 illustrates generally an example of an ambulatory medical device that can be configured to analyze a signal indicative of the movement of the implantable lead.

FIG. 4A illustrates generally an example of a technique 400 for analyzing information indicative of a vibration of an implantable lead, such as included in the IMD of one or both of FIGS. 1 and 9. At 410, an excitation circuit, such as the excitation circuit 110, can provide a non-tissue stimulating, non-therapeutic electrical excitation signal to the implantable lead 145, as discussed in FIG. 1. At 420, the receiver circuit 115 of the IMD 105 can obtain an LMI signal including a mechanical contraction waveform or a mechanical vibration waveform from the implantable lead 145 in response to the excitation signal. At 430, information indicative of valvular activity can be determined from the mechanical vibration waveform, such as by the processor 190 as described in FIG. 1. In an example, the mechanical vibration waveform can be extracted from the LMI signal using one or more filters, such as the filter circuit 195.

Figure 4B:
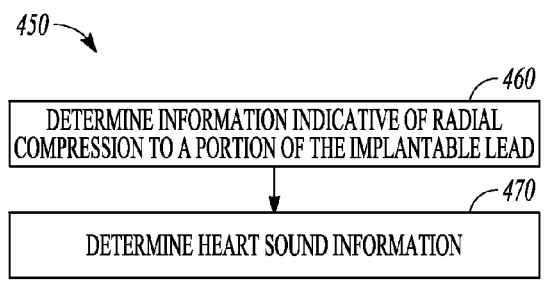

FIG. 4B illustrates generally an example of a technique 450 for analyzing information indicative of a vibration of an implantable lead, such as included in the IMD of one or both of FIGS. 1 and 9. At 460, information indicative of radial compression to the implantable lead corresponding to blood pressure or blood flow can be determined from the mechanical vibration waveform such as by the processor circuit 190 of FIGS. 1 and 9 using one or more filters, such as the filter circuit 195. At 470, heart sound information, including magnitude information, duration information, or timing information, can be determined from the radial compression information or the mechanical vibration waveform.

Figure 5A:
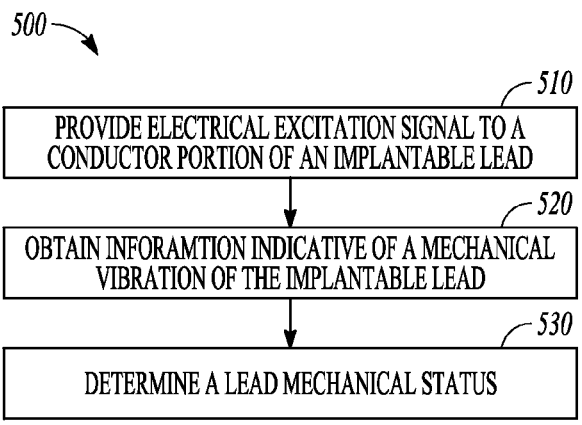
FIGS. 5A-5B illustrate generally examples of techniques that can include analyzing information indicative of a vibration of the implantable lead.

FIG. 5A illustrates generally an example of a technique 500 for analyzing information indicative of a vibration of an implantable lead, such as included in the IMD of one or both of FIGS. 1 and 9. At 510, an excitation circuit, such as the excitation circuit 110, can provide a non-tissue stimulating, non-therapeutic electrical excitation signal to the implantable lead 145, as discussed in FIG. 1. At 520, the receiver circuit 115 of the IMD 105 can obtain an LMI signal including a mechanical contraction waveform or a mechanical vibration waveform from the implantable lead 145 in response to the excitation signal. At 530, a lead mechanical status can be determined from the mechanical vibration waveform, such as by the processor 190 as described in FIG. 1. In an example, the mechanical vibration waveform can be extracted from the LMI signal using one or more filters, such as the filter circuit 195.

Figure 5B:
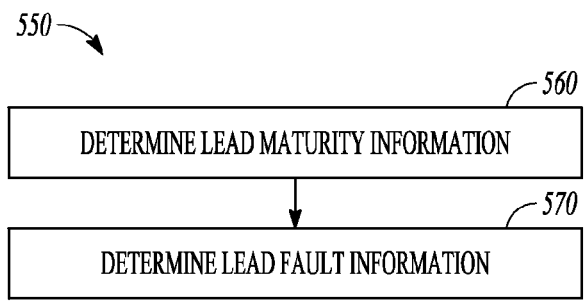

FIG. 5B illustrates generally an example of a technique 550 for analyzing information indicative of a vibration of an implantable lead, such as included in the IMD of one or both of FIGS. 1 and 9. At 560, lead "maturation" information can be determined, such as by the processor of FIG. 1, such as indicated one or more metrics obtained from the mechanical vibration waveform from the implantable lead 145. At 570, lead fault information can be determined via an analysis over time of the one or more metrics obtained from the mechanical vibration waveform. For example, a metric associated with a current duration can be compared to a metric associated with a baseline (e.g., a metric associated with a "mature" lead.). When the comparison results in a difference meeting a specified criterion (e.g., within a specified range of values), the processor 190 can provide an indication of a lead fault.

FIG. 6 illustrates generally an illustrative example of a relationship between the magnitude of a response signal versus frequency. As described above, the IMD 105 can include a receiver circuit 115, for example, configured to receive a signal indicative of the motion of the implantable lead, such as the response signal, obtained in response to an excitation signal provided by the excitation circuit 110. In an example, the magnitude 600 of the response signal can vary as a function of frequency due the electrical characteristics of the implantable lead 145 over a specified frequency range. For example, a relatively stable or "flat" magnitude response (e.g., a magnitude value within a defined range) can result from the interaction of the electrical characteristics of the implantable lead 145 and the excitation signal in a first frequency range 605, such as between DC or near-DC (e.g., about 0 Hz) and a second frequency 615 (e.g., about 10 KHz), such as due to the resistive components of the lead impedances 350-360 having more influence than the capacitive, or inductive components. However, for an excitation signal within a second frequency range 607 (e.g., from about 50 MHz to about 150 MHz), the capacitive or inductive elements of the lead impedances 350-360 can dominate the response, such as causing the response signal magnitude 610 to decline as a function of frequency over the second frequency range 607.

In an example, the interaction of an excitation signal at a frequency, such as frequency 617, and the electrical characteristics of the implantable lead 145 can result in a response signal 620, such as having a magnitude 622. In an example, the electrical characteristics of the implantable lead 145 can result from inductive or capacitive coupling between portions of the implantable lead such as due to the position and or location of the implantable lead 145 within or near the heart. In an example, the motion of the heart, such as a cardiac contraction cycle, can result in corresponding motion of the implantable lead 145. In an example, the motion of the implantable lead can cause the electrical characteristics of the implantable lead 145 to vary as a function of time. For example, the motion of the implantable lead can cause the magnitude of the response signal to vary as a function of time over a specified frequency range. Such magnitude signals 640, 650, can result from the variance in the electrical characteristics due to motion of the implantable lead caused, at least in part, by motion of the heart 205.

In an example, an excitation signal at a frequency 617, such as provided by the excitation circuit 110, can interact with the time-varying electrical characteristics of the implantable lead 145, such as to provide a signal indicative of the motion of the implantable lead 145 (e.g., a response signal at least in part including an LMI signal 630). For example, the excitation signal at a frequency 617 can interact with the time-varying electrical characteristics of the implantable lead 145 during motion of the implantable lead. The motion of the implantable lead 145, such as caused a cardiac contraction cycle, can result in a response signal at a specified frequency having a time-varying magnitude value that can vary between a peak value 632A and a minimum value 634A. In an example, the response signal can include a carrier signal at the excitation frequency 617, and a modulating signal, such as a time-varying component resulting from the motion of the implantable lead (e.g., the LMI signal 630). For example, the magnitude of the LMI signal 630 can correspond to the time-varying magnitude of the response signal at the specified frequency such that the magnitude of the LMI signal 630 can vary between a peak value 632B and a minimum value 634B. In an example, the response signal can be conditioned such as to extract or otherwise provide the LMI signal for use by an analysis circuit, such as the arrhythmia classification circuit 120. Phase information can also be obtained, such as with respect to a reference phase corresponding to the excitation signal. Thus, the techniques above can be applied generally to magnitude or phase information, or to a real part or imaginary part of the response signal, in the case of a complex response signal.

Figure 7:
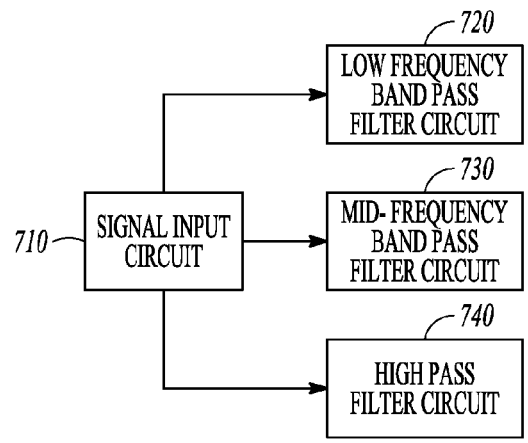
FIG. 7 illustrates generally an example of a system that can be used for conditioning a signal.

FIG. 7 illustrates generally an example of a system that can be used for conditioning a response signal for analysis. In an example, the receiver circuit 115 can include a signal input circuit 710, such as configured to receive a response signal from the implantable lead 145. In an example, the signal input circuit can include circuitry such as configured to provide, or otherwise obtain, the LMI signal from the response signal. For example, the LMI signal provide or otherwise obtained via demodulation, such as to remove a carrier frequency 617, such as to provide the LMI signal (e.g., via AM demodulation such as envelope detection or filtering, or via FM demodulation such as using a phase-locked loop, etc.). In an example, the LMI signal can include information about the motion of the implantable lead, such as caused by mechanical manipulation of the one or more leads caused by motion of at least one of the heart muscle, a heart valve, respiratory musculature, lungs, skeletal musculature, a variation in blood pressure, or other forces acting directly on the one or more leads.

In an example, the receiver circuit 115 can include one or more filters to provide information about one or more physiological conditions associated with the heart, such as information about the motion of the implantable lead in the LMI signal. In an example, the implantable lead 145 can be moved slowly, such as due to bending resulting from a cardiac contraction cycle. The implantable lead 145 can move quickly, such as caused by an impact on the lead resulting from a valve closure. In an example, the LMI signal can be filtered in one or more frequency ranges, such as to distinguish between one or more causes of the motion of the implantable lead. In an example, the receiver circuit 115 can include a low-frequency band-pass filter circuit 720, a mid-frequency band-pass filter circuit 730, or a high-pass filter circuit 740. In an example, the filter circuits 720-740 can include a near-DC filter circuit, such as a high-pass filter circuit 740 configured to attenuate or remove signal noise under a frequency (e.g., about 0.05 Hz), configured to provide a baseline such as by filtering near-DC signal components. For example, the baseline can correspond to a near zero-energy or near-zero magnitude LMI signal when the implantable lead is not moving. In an example, the near-DC filter circuit can be included in one or more of the low-frequency band-pass filter circuit 720, the mid-frequency band-pass filter circuit 730, or the high-pass filter circuit 740.

In an example, the low-frequency band-pass filter circuit 720 can be configured to filter the LMI signal, for example, at a low frequency range (e.g., from about 0.05 Hz to about 10 Hz), such as to provide information indicative of the motion of the implantable lead 145, such as due to mechanical motion of the heart 205. For example, the low-frequency band-pass 720 filter can provide a filtered LMI signal representative of the motion of the implantable lead due to motion caused by a cardiac contraction cycle. In an example, the filtered LMI signal can provide information representative of motion of the one or more implantable leads such as useful for verification of capture of a electrostimulation pulse, managing fusion in capture detection applications or CRT applications, or monitoring to detect a lead dislodgment. In an example, the filtered LMI signal can be used for monitoring myocardial contraction such as to manage a CRT therapy, to detect myocardial ischemia, to determine relative changes in stroke volume, or cardiac output, to detect abnormalities with relaxation of the cardiac muscle, or to detect abnormal mechanical contraction and to monitor electro-mechanical delay in the myocardium.

In an example, the mid-frequency band-pass filter circuit 730 can be configured to filter the LMI signal, such as over a mid-frequency range (e.g., from about 0.05 Hz to about 30 Hz), such as to provide information indicative of the motion of the implantable lead 145, such as due to mechanical motion of the heart 205. For example, the mid-frequency band-pass filter 730 can provide a filtered LMI signal representative of the motion of the implantable lead due to motion caused by a cardiac contraction cycle. For example, the filtered LMI signal can provide information useful for decompensation detection, rhythm discrimination using myocardial contraction morphology or myocardial contraction spectrum, such as to guide therapy to determine if ATP should be attempted before a shock, determine the timing of the shock, to detect an arrhythmia, or to assess autonomic function. In an example, the filtered LMI signal can be used to monitor the integrity of the implantable lead.

In an example, the high-pass filter circuit 740 can be configured to filter the LMI signal, such as to filter signal out signal components under a specified frequency range (e.g., above about 10 Hz), such as to provide information indicative of the motion of the implantable lead 145, such as due to mechanical motion of the heart 205. For example, the high-pass filter 740 can provide a filtered LMI signal representative of the motion of the implantable lead due to motion caused by one or more portions of the heart during a cardiac contraction cycle (e.g., a valve impact, frictional contact between cardiac muscle and the implantable lead, etc.). For example, the filtered LMI signal can provide information useful to detect heart sounds, or to detect the timing and amplitude of valve impact on leads. In an example, the filtered LMI signal can be used to detect lead maturity (e.g., a connection between myocardial tissue and the implantable lead 145), or lead dislodgement. In an example, the filtered LMI signal can be used for dissynchrony measurement or CRT optimization, such as by detecting right side and left side heart sounds.

FIG. 8 illustrates generally an illustrative example that can include filtering or otherwise conditioning a response signal. In an example, an LMI signal can be obtained by the receiver circuit 115, such as can include an LMI signal indicative of the motion of the implantable lead 145, such as the LMI signal 810. In an example, the LMI signal 810 can be filtered, such as to provide information about the cardiac contraction cycle. For example, the LMI signal 810 can be filtered, such as by the low-frequency band-pass filter 720, such as to provide a filtered LMI signal 820 such as a mechanical contraction waveform.

FIG. 9 illustrates generally an example of an ambulatory medical device that can be configured to analyze a signal indicative of the movement of the implantable lead 145, such as for an indication of the movement of the heart 205 during a cardiac contraction cycle. In an example, the IMD 105 of FIG. 1 can include one or more of the excitation circuit 110, the receiver circuit 115, an arrhythmia detection circuit 120, an arrhythmia classification circuit 125, the sensing circuit 130, the therapy generation circuit 135, the lead interface connection 140, the communication circuit 160, an autonomic function monitor circuit 161, a contraction characteristic determination circuit 170, a therapy adjustment circuit 171, a decompensation status circuit 175, a lead status indication circuit 181, the processor circuit 190, a heart sound sensing circuit 191, or a cardiac resynchronization optimization circuit 193.

In an example, the processor circuit 190 can include the arrhythmia detection circuit 120 or the arrhythmia classification circuit 125. For example, the arrhythmia detection circuit 120 can be configured to detect an arrhythmia using information (e.g., amplitude information) from the LMI signal such as within one or more frequency ranges. For example, the arrhythmia detection circuit 120 can be configured to compare amplitude information determined over a first frequency range to amplitude signal information determined over a second frequency range, such as from one or more LMI signals, as described above. In an example, the first frequency range can correspond to a lower frequency range (e.g., from about 0.05 to about 2 Hz), such that the obtained amplitude information can include information corresponding to movement of the myocardium, such as due to bending or compression of the implantable lead 145 during a normal cardiac contraction cycle. In an example, amplitude information such as determined over an upper frequency range (e.g., near 10 Hz) can correspond to motion indicative of an arrhythmia (e.g., ventricular arrhythmia, ventricular fibrillation, etc.). In an arrhythmic example, such as during an arrhythmia, the arrhythmia detection circuit 120 can obtain information including the second frequency range, such as due to motion associated with rapid or uncoordinated contractions of the heart (e.g., arrhythmia, fibrillation, etc.), even if gross myocardial motion is reduced or absent.

In an example, the arrhythmia detection circuit 120 can be configured to declare an arrhythmia such by comparing a relative indication of information about LMI signal magnitudes determined during a first duration (e.g., an interval of time corresponding to current, possibly arrhythmic, cardiac activity) against LMI signal information obtained during a previous duration (e.g., a template of normal or arrhythmic activity). For example, the arrhythmia detection circuit 120 can be configured to determine a ratio of the LMI signal magnitude within the upper frequency range to a LMI signal magnitude within a lower frequency range within a current duration. The arrhythmia detection circuit 120 can be configured to compare the ratio of LMI signal magnitude information from the current duration to a ratio of LMI signal magnitude information from a previous duration such as using a criterion. For example, an arrhythmia can be declared when a comparison of the value of the ratio of the current duration to the value of the ratio of the previous duration meets the criterion, such as exceeding a threshold. The arrhythmia detection circuit 120 can be configured to confirm an arrhythmia condition diagnosis, such as an arrhythmia detected using an electrogram sensed by the sensing circuit 130. For example, the IMD 105 can be configured to detect an arrhythmia using interval information or one or more other criteria, such as using information about an electrical signal obtained by a sensing circuit 130.

For example, the arrhythmia classification circuit 125 can be configured to determine, (e.g., from one or more metrics from an LMI signal as described above), one or more of a location (e.g., atrium ventricle, etc.), or a type (e.g., ventricular, supraventricular, etc.) of an arrhythmia, such as in response to the arrhythmia detection circuit 120 determining that an arrhythmia is occurring or has occurred.

In an example, the arrhythmia classification circuit 125 can be configured to discriminate between arrhythmias such as by comparing an LMI signal obtained during a first duration of time (e.g., such as an LMI signal measured during an identified normal sinus rhythm, or an otherwise hemodynamically-stable rhythm) to an LMI signal obtained during second duration of time (e.g., during a time of an identified arrhythmia). In an example, the arrhythmia classification circuit 125 can be configured to determine an arrhythmia type, or arrhythmia location using one or more of (1) myocardial contraction morphology, (2) a myocardial contraction spectrum, or other techniques to analyze information corresponding to the motion of the implantable lead 145, such as including information obtained from an LMI signal.

In an example, the IMD 105 can be configured to determine an arrhythmia classification using a morphology-based technique, such as disclosed in the commonly assigned U.S. Pat. No. 6,275,732, "Multiple Stage Morphology-Based System Detecting Ventricular Tachycardia and Supraventricular Tachycardia" which is incorporated herein by reference in its entirety, including its description of determining and classifying ventricular and supraventricular tachyarrhythmia using a signal representative of cardiac electrical activity.

In an example, the arrhythmia classification circuit 125 can be configured to determine whether the arrhythmia has a ventricular or supraventricular origin using the determinations of whether the first LMI signal is the same as or different from the second LMI signal for the one or more implantable leads, such as the implantable lead 145. In an example, the arrhythmia classification circuit can classify a ventricular arrhythmia as a result of a supraventricular determination. For example, if the arrhythmia classification circuit 125 determines that a detected arrhythmia is not supraventricular, then the arrhythmia classification circuit 125 can deem the arrhythmia to have ventricular origin. For example, the arrhythmia detection circuit 125 can identify a supraventricular arrhythmia, such as by determining a 1:1 correlation exists between atrial and ventricular beats. In an example, a ventricular arrhythmia can be identified, such as by using the LMI signal, when an indication of an atrial beat, if even present, is followed by indications of two or more ventricular beats.

In an example, an arrhythmia can be classified using information about a location of high-rate or uncoordinated activity, such as using one or more LMI signals received from the one or more implantable leads. In an example, the arrhythmia classification circuit 125 can be configured to determine whether a detected arrhythmia has ventricular or supraventricular origin, such as by comparing the arrhythmia indications determined from the one or more LMI signals to a criterion. For example, the criterion can be determined using a LMI signal during a duration of a known sinus rhythm of the subject's heart such as a 1:1 correlation of atrial beats to ventricular beats within a specified heart rate range (e.g., sixty to one hundred beats per minute). In an example, the arrhythmia classification circuit 125 can be configured to determine a ventricular or supraventricular determination from the LMI signal information, such as by using timing information or morphology information obtained during a specified interval or duration. For example, a ventricular arrhythmia can be indicated, such as when a count of indicated ventricular beats exceeds a count of identified atrial beats during a specified duration. Similarly, if an identified ventricular contraction follows an atrial contraction, during a duration, the arrhythmia can be determined to be supraventricular. For example, if the one or more LMI signals indicative of a supraventricular arrhythmia meet a criterion, such as exceed a threshold, the arrhythmia can be deemed supraventricular.

In an example, the processor circuit 190 can include the therapy adjustment circuit 171 configured to adjust a therapy provided by the therapy generation circuit 135. For example, the therapy adjustment circuit 171 can be configured to adjust an anti-tachyarrhythmia pacing (ATP) therapy or a shock therapy using metrics obtained from at least one of the mechanical contraction waveform, the mechanical vibration waveform, or the signal indicative of cardiac electrical activity, as described above. The ATP therapy can be based on the current state of the subject (e.g., as indicated by one or more metrics of the mechanical contraction waveform as described above) and can permit the ATP therapy to be delivered, or can be used to trigger an extension of the ATP therapy duration as compared to a subject state where defibrillation therapy is to be delivered immediately.

In an example, an arrhythmia can be detected and classified, such as by the arrhythmia detection circuit 120 or the arrhythmia classification circuit 125, but the heart 205 is still adequately meeting the patients metabolic demand. Such an arrhythmia can be classified as "hemodynamically stable." Often such arrhythmias can self-terminate. In such cases, a shock therapy, such as provided by the therapy generation circuit 135 to terminate the non-sustained arrhythmia, can be delayed or inhibited to avoid unnecessary shocks to the subject. In some cases, a sustained ventricular arrhythmia can be re-entrant and therefore susceptible to termination via a generated ATP therapy. The ATP therapy can be delivered to at least one pacing site (e.g., within the right ventricle) and be designed to cause a depolarization within the myocardium to terminate the arrhythmia by interfering with the timing of the re-entrant arrhythmia depolarization.

In an example, the therapy adjustment circuit 171 can be configured to determine whether an arrhythmia is hemodynamically stable, such as by using at least one of a hemodynamic stability metric or a hemodynamic stability concordance metric. For example, the arrhythmia can be determined to be hemodynamically stable when at least one of the hemodynamic stability metric or the hemodynamic stability concordance metric meets a specified criterion (e.g., exceeds a threshold or is within a specified range).

For example, the hemodynamic stability metric or the hemodynamic stability concordance metric can be determined such as by using one or more contraction metrics (e.g., a peak determination, a peak-to-peak determination, a number of deflections within a specified duration, etc.), as described above and obtained from the mechanical contraction waveform. In an example, the hemodynamic stability metric can be determined using a central tendency of the contraction metric, such as a peak-to-peak determination, over a specified duration. In an example, the central tendency can be determined using contraction metrics that meet a specified criterion (e.g., a minute, an hour, etc.). For example, peak-to-peak determinations that exceed a specified threshold or are within a specified range can be used for computing the central tendency over the specified duration. In an example, a concordance metric can be determined using a contraction metric, as described above, obtained from one or more mechanical contraction waveforms received from at least one implantable lead 145.

The concordance metric can correspond to the concordance of the synchrony of the contraction metrics obtained from the one or more mechanical contraction waveforms. For example, determining a concordance of the metrics can be accomplished using one or more techniques, such as the techniques described in one or more of Lawrence I-Kuei Lin *A Concordance Correlation Coefficient to Evaluate Reproducibility, Biometrics* (International Biometric Society) 45 (March 1989) at 255-268, Reinhold Müller & Petra Büttner *A Critical Discussion of Intraclass Correlation Coefficients*, Statistics in Medicine 13 (23-24) (December 1994) at 2465-2476, or Klaus Krippendorff *Bivariate Agreement Coefficients for Reliability of Data*, In E. F. Borgatta and G. W. Bohnstedt (Eds.) *Sociological Methodology*, Jossey-Bass. (1970) at 139-150. The concordance metric can have a value between zero and one, where one corresponds to the highest synchrony between the contraction metrics of the mechanical contraction waveforms. In an example, the hemodynamic stability concordance metric can be determined by multiplying the concordance metric by the hemodynamic stability metric.

In an example, the therapy adjustment circuit 171 can be configured to allow the therapy generation circuit 135 to generate an ATP therapy such as when one of the hemodynamic stability metric or the hemodynamic stability concordance metric meets a specified criterion. While the ATP therapy is being generated and the arrhythmia is still present, the therapy adjustment circuit 171 can be configured to compute the hemodynamic stability metric or the hemodynamic stability concordance metric continuously, or at specified intervals (e.g., once per minute, etc.). In an example, the ATP therapy can be terminated by the therapy adjustment circuit 171 determines that the arrhythmia is no longer present, or when a shock therapy is needed because the arrhythmia is no longer hemodynamically stable.

In an example, the therapy adjustment circuit 171 can be configured such as to determine a timing of a defibrillation shock therapy. The effectiveness of a defibrillation shock delivered to myocardial tissue can depend on the local current density produced by the shock in such tissue. For example, the ability of the shock to terminate an arrhythmia can depend on the current carrying characteristics of the myocardial tissue at the location of the delivered shock (e.g., such as an RV coil located near the lateral surface of the LV apex). Generally, current densities resulting from a delivered shock can be determined using the cardiac geometry and the physical location of the myocardial tissue relative to the shock electrodes, where the current density is associated with the energy delivered over an area (e.g., an area of myocardial tissue contacting or near the shock electrode). When the myocardial tissue contracts, more of the tissue can be exposed to higher current densities than when the tissue is relaxed. For example, within the cardiac tissue, individual cardiac muscle cells are connected to form a three dimensional structure. The cardiac muscle cells (e.g., cardiac myocytes) have a generally tubular shape that shorten during a cardiac contraction to produce force. Because, more cardiac muscle cells lie within a given area (e.g., the area adjacent to the shock electrode) during the contraction, more cardiac muscle cells can be exposed to the higher current densities delivered by the shock electrode. During ventricular fibrillation, the amount of contraction of the myocardial tissue can vary over time.

In an example, a shock delivered during a cardiac contraction can require about fifteen percent lower energy to defibrillate than when the myocardial tissue is in its relaxed state. Timing the generation of a defibrillation shock to a time period during a myocardial contraction can improve the effectiveness of the shock. In an example, the therapy adjustment circuit 171 can use an electrogram feature (e.g., a QRS complex from an electrogram received from an implantable lead 145 within the RV), or a contraction metric of a mechanical contraction waveform to time the generation of a defibrillation shock (e.g., trigger). However, if an electrogram is unavailable, the defibrillation shock can be generated asynchronously.

In an example, one or more contraction metrics (e.g., a peak-to-peak determination, a peak determination, timing information, etc.), as described above, can be determined from one or more mechanical contraction waveforms. The contraction metrics can be used by the therapy adjustment circuit 171 to determine the timing of a generated defibrillation shock. As described above, a contraction metric can be analyzed to determine whether periodic contractions (e.g., a periodic arrhythmia) exist. A central tendency (e.g., an average, median, mean, etc.) of the contraction metric (e.g., a magnitude of a peak-to-peak deflection) can be analyzed such by comparing the central tendency to a criterion (e.g., a threshold) such as to determine whether periodic contractions exist. In an example, the central tendency can be calculated using contraction metrics meeting a criterion, such as exceeding a threshold or being within a specified range. In an example, a periodic contraction can be identified when the central tendency of the contraction metrics of the one or more mechanical contraction waveforms meet a specified criterion.

In an example, the therapy adjustment circuit 171 can determine the timing of the defibrillation shock using one or more mechanical contraction waveforms. For example, the timing of the defibrillation shock can be determined using the contraction metrics of the mechanical contraction waveform having the largest peak-to-peak magnitudes, or using a composite mechanical contraction waveform as described above. In an example, the defibrillation shock can be timed to be generated such as when the peak-to-peak characteristic reaches a maximum value.

In an example, the processor circuit 190 can include the autonomic function monitor circuit 161. Generally, cardiac function can be strongly influenced by sympathetic and parasympathetic activity. For example, heart rate, the contraction strength of the myocardial tissue and the synchrony of contractions between two or more heart chambers can be increased by sympathetic activity and reduced by parasympathetic activity. One or more contraction metrics of one or more mechanical contraction waveforms or mechanical vibration waveforms can be associated with the autonomic function of the subject's body. Particularly, rich variability of one or more contraction metrics can correspond to normal autonomic control over cardiac function. Conversely, reduced variability can correspond to a lessening of the effectiveness of a subject's autonomic function.

In an example, the autonomic function monitor circuit 161 can be configured to determine a contraction metric (e.g., a peak-to-peak determination, a peak determination, a root-mean-square determination, a relative indication of information about a portion of the LMI signal such as a percentage of an absolute or local maximum or minimum or an absolute value of at least a portion of the mechanical contraction waveform), or a central tendency of the contraction metric (e.g., an average, a median, a mean, etc.). In an example, the relative indication of information about a portion of the LMI signal can include a rise time (e.g., from about 10% to about 90% of a peak value), a fall time (e.g., from about 90% to about 10% of a peak value), a rising or falling slope (e.g., between about 10% to about 90% of a peak value).

The autonomic function monitor circuit 161 can be configured to determine one or more contraction metrics from the one or more mechanical contraction waveforms occasionally or periodically (e.g., once every few minutes, hourly, several times per day, or during or between one or more other specified intervals) for an variability indication of cardiac function. For example, the autonomic function monitor circuit 161 can be configured to determine a contraction metric during a duration (e.g., one or more minutes, several seconds, etc.) between the occasional or periodic samples. In an example, the contraction metric can be determined during a duration of low physiological activity (e.g., during sleep, during a period of low activity, during a period where heart rate is within a specified range, etc.). In an example, the autonomic function monitor circuit 161 can be configured such as to determine a contraction metric during a duration between a specified start time and a specified end time. In an example, the contraction metric can be determined over one or more contiguous intervals of a specified duration.

In an example, the autonomic function monitor circuit 161 can be configured to determine an indication of autonomic function using a variability metric of the one or more determined contraction metrics. In an example, the variability metric can be calculated during a specified duration or between two or more durations. In an example, a variability metric can correspond to a standard deviation of a contraction metric over two or more durations, such as to determine a variability coefficient for the metric and associated with the analyzed duration. In an example, a characteristic of the variability metric (e.g., a central tendency, a square root of the central tendency, etc.) can be determined for one or more mechanical contraction waveforms. In an example, the indication of autonomic function can include, for example, the square root of an average variability metric divided by the average of the corresponding contraction metric).

In an example, the processor circuit 190 can include the cardiac resynchronization optimization circuit 193 In an example, the processor circuit 190 can be configured to modify a therapy, such as a cardiac resynchronization therapy (CRT), such as by synchronizing the contractions of the right and left ventricles. For example, an indications of an RV contraction or an LV contraction can be determined from the mechanical contraction waveform or the mechanical vibration waveform received from an RV lead or an LV lead, respectively. The mechanical contraction waveform and the mechanical vibration waveform of the two or more implantable leads can be obtained simultaneously with a signal indicative of cardiac electrical activity (e.g., such as an optionally obtained an intracardiac electrogram) from either the RV lead, the LV lead, or both. In an example, the processor circuit 190 can determine a synchrony metric, such as between the RV and the LV, using one or more metrics of contraction as described above. For example, a synchrony metric can correlate the synchrony between the RV and LV contractions using timing information obtained from, for example, the LMI signals received from the RV lead and the LV lead.

In an example, the processor circuit 190 can include a decompensation detection circuit 175. In a subject experiencing congestive heart failure (HF), the subject may experience one or more physiological changes to the heart associated with a decompensation event. For example, a change in one or more mechanical contraction signals can indicate a reduction in one or more of cardiac contractility, cardiac output, stroke volume, or can indicate abnormal filling. The decompensation detection circuit 175 can be configured to determine an indication of a change to the mechanical contraction signal such as can indicate the onset or occurrence of a HF decompensation event. For example, during decompensation, the mechanical contraction waveform can have smaller amplitudes (e.g., peak determinations) indicative of a smaller difference between the relaxed and contracted states of the heart due to increased heart size or a reduced ejection fraction. Additionally, a reduction in a relative indication of information about a portion of the LMI signal (e.g., a percentage of an absolute or local maximum or minimum) can be indicative of a reduction to the vigor of cardiac mechanical contractions.

In an example, the decompensation detection circuit 175 can be configured to determine one or more contraction metrics from the one or more mechanical contraction waveforms occasionally or periodically (e.g., once every few minutes, hourly, several times per day, or during or between one or more other specified intervals). For example, the decompensation detection circuit 175 can be configured to determine a contraction metric during a duration (e.g., one or more minutes, several seconds, etc.) between the occasional or periodic samples. In an example, the contraction metric can be determined during a duration of low physiological activity (e.g., during sleep, during a period of low activity, during a period where heart rate is within a specified range, etc.). In an example, the autonomic function monitor circuit 161 can be configured such as to determine a contraction metric during the duration between a specified start time and a specified end time. In an example, the contraction metric can determine over one or more contiguous intervals of a specified duration.

In an example, the decompensation detection circuit 175 can be configured to determine a contraction metric (e.g., a peak-to-peak determination, a peak determination, a root-mean-square determination, a relative indication of information about a portion of the LMI signal such as a percentage of an absolute or local maximum or minimum or an absolute value of at least a portion of the mechanical contraction waveform), or a central tendency of the contraction metric (e.g., an average, a median, a mean, etc.). In an example, the relative indication of information about a portion of the LMI signal can include a rise time (e.g., from about 10% to about 90% of a peak value), a fall time (e.g., from about 90% to about 10% of a peak value), a rising or falling slope (e.g., between about 10% to about 90% of a peak value). The decompensation detection circuit 175 can be configured to store the determined contraction metric and compare recent contraction metrics to the stored contraction metrics. In an example a reduction in a contraction metric (e.g., peak-to-peak deflection, a rise time, a fall time, etc.) can cause the decompensation detection circuit 175 to generate a decompensation indication when the reduction meets a specified criterion (e.g., exceeds a threshold, lies outside a specified range, etc.).

Figure 10:
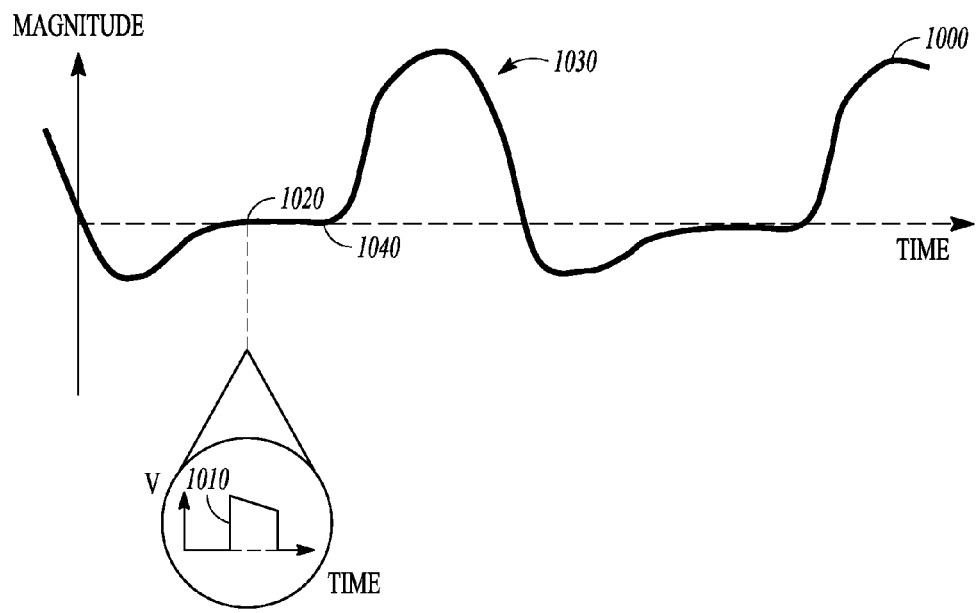
FIG. 10 illustrates generally an illustrative example of a relationship between a pacing pulse and a mechanical cardiac contraction.

FIG. 10 illustrates generally an illustrative example of a relationship between a pacing pulse 1010 and a mechanical cardiac contraction 1030. A patient receiving a pacing therapy, such as a pacing therapy for treating an arrhythmia, the mechanical contraction waveform 1000 can provide an indication of therapy effectiveness (e.g., capture verification information). Such an indication can be determined such as by using interval information between time of the generation 1020 of the pacing pulse 1010 and a time 1040 at or near the start of the mechanical cardiac contraction 1030. In an example, capture verification information can be determined, such as by the processor circuit 190, using a portion of signal indicative of cardiac electrical activity (e.g., electrogram information indicative of electrical depolarization following pacing pulse generation). However, electrical depolarization alone may not be indicative of capture, such as due to one or more sources of electrical signal interference (e.g., fusion with another beat, variation in sensed event timing or morphology, noise, etc.). In an example, the processor circuit 190 can receive, such as from the receiver circuit 115 or the filter circuit 195, an LMI signal, such as including the mechanical contraction waveform 1000. A pacing pulse 1010 can be deemed to have captured a corresponding contraction 1030 such as when the interval between the time of generation 1020 and a point near or at the start of a cardiac mechanical contraction is less than a threshold (e.g., within about 100 ms, or about 200 ms, of a delivered electrostimulation pulse).

Figure 11:
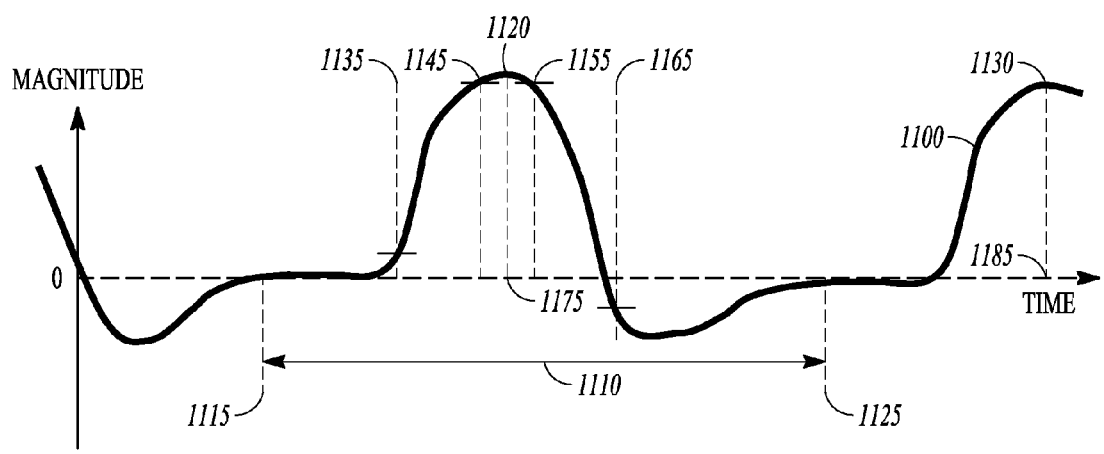
FIG. 11 illustrates generally an illustrative example of information indicative of a change to cardiac health information using information indicative of the movement of the implantable lead.

FIG. 11 illustrates generally an illustrative example of information that can be determined from a mechanical contraction waveform 1100. In an example, a mechanical contraction waveform 1100 can be obtained from one or more implantable leads 145 such as to provide information indicative of a mechanical cardiac contraction. In an example, the mechanical contraction waveform 1100 can include interval information such as between a first locus at 1115 and a second locus 1125, such as indicative of a mechanical contraction cycle 1110 of the heart.

In an example, the mechanical contraction waveform 1100 can include peak information 1120, 1130, such as can indicate a peak magnitude associated with the mechanical contraction of the heart. For example, an interval associated with successive or adjacent peaks 1120, 1130 can provide interval information (e.g., between time 1175 and time 1185), such as indicative of a heart rate.

In an example, the mechanical contraction waveform can include rate of change information such as a rise time (e.g., between time 1135 and time 1145) or a fall time (e.g. between time 1155 and time 1165). For example, the rise time can be computed between two or more times associated with a specified magnitudes, such as time 1135 associated with a magnitude 10% of the peak value and time 1145 associated with a magnitude of 90% of the peak value, or using one or more other criteria. Conversely, a fall time can be computed between time 1155 associated with a magnitude of 90% of the peak value and time 1165 associated with a magnitude of 10% of the peak value, or using one or more other criteria.

FIG. 12 illustrates generally an illustrative example of information that can include filtering or otherwise conditioning a response signal. In an example, an LMI signal can be obtained by the receiver circuit 115, such as can include an LMI signal indicative of the motion of the implantable lead 145, such as the LMI signal 1210. In an example, the LMI signal 1210 can be filtered, such as to provide information about the cardiac contraction cycle. For example, the LMI signal 1210 can be filtered, such as by the high-pass filter 740, such as to provide a filtered LMI signal 1220 such as a mechanical vibration waveform. The mechanical vibration waveform can include features such as associated with frictional contact with the implantable lead 145, such as feature 1250, or an impact to the implantable lead, such as feature 1260.

FIG. 13A illustrates generally an illustrative example of information indicative of a lead mechanical status 1300 that can be determined from a mechanical vibration waveform. The waveform 1300 can correspond to a metric of the mechanical vibration waveform associated with a magnitude of a frictional component associated with frictional contact of the implantable lead to a portion of the heart 205, as described above. For example, a portion 1310 of the waveform can correspond to the "maturation" process of the implantable lead 145 associated with tissue ingrowth or endothelialization to a portion of the heart 205. At a time 1315, tissue lead maturity can be reached such as when the magnitude of the frictional component meets a specified criterion. At 1325, an event (e.g., a fracture, a sudden movement) can cause the implantable lead to become dislodged from the heart completely (e.g., a full dislodgement of tissue ingrowth and at the point of fixation) or a partial dislodgment (e.g., dislodgement of either the tissue ingrowth or at the point of fixation). After dislodgement at time 1325, the waveform 1330 can increase from the "maturation" level.

Figure 13B:
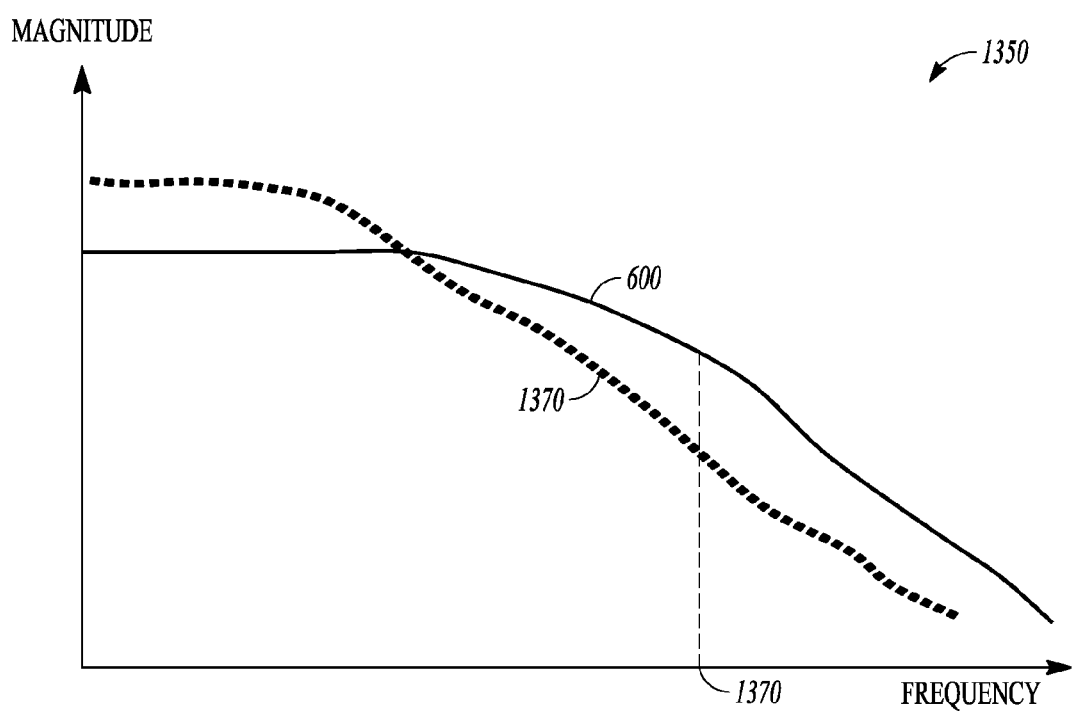

FIG. 13B illustrates generally an illustrative example of information indicative of a lead mechanical status 1300 that can be determined from a mechanical vibration waveform. In an example, the magnitude 600 of the response signal can vary as a function of frequency due the electrical characteristics of the implantable lead 145 over a specified frequency range. Over time, the electrical characteristics of the implantable lead can change as the implantable lead ages or as a result of abrasion or other physical changes, such as magnitude 1370. At a specified frequency 1370, such as at the frequency of the excitation signal, a lead mechanical status can be determined from the difference between the magnitude 600 and magnitude 1370 at the excitation signal frequency 1370.

Figure 14:
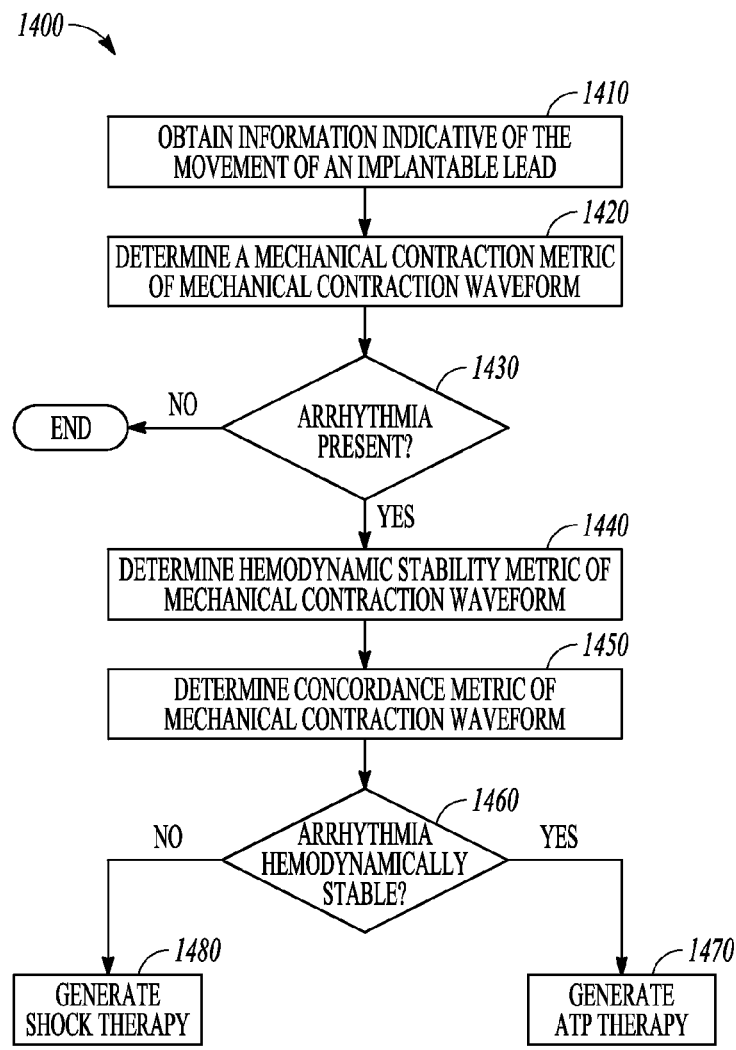
FIG. 14 illustrates generally a technique for adjusting a therapy using information indicative of the movement of the implantable lead.

FIG. 14 illustrates generally an example of a technique 1400 for analyzing information indicative of the motion of an implantable lead, such as included in the functionality of the IMD 105 of FIGS. 1 and 9. At 1410, the information indicative of the motion of the implantable lead 145 can be obtained such as by the processor circuit 190, such as to analyze at least a portion of a mechanical contraction waveform indicative of a mechanical contraction (e.g., a portion of the mechanical contraction waveform including peak information). At 1420, a mechanical contraction metric can be determined from one or more mechanical contraction waveforms, such as by the processor circuit 190. At 1430, the mechanical contraction metric is analyzed to detect whether an arrhythmia is present, such as by the arrhythmia detection circuit 120. Optionally, the arrhythmia classification circuit 125 can determine whether the detected arrhythmia has ventricular or supraventricular origin. If, at 1430, the arrhythmia is present, the mechanical contraction waveform can be analyzed to determine an indication of hemodynamic stability at 1440. If not, the technique ends.

At 1450, a hemodynamic concordance metric can be determined such as by the therapy adjustment circuit 171 from the mechanical contraction metric from one or more mechanical contraction waveforms from one or more implantable leads. At 1460, one or more of the hemodynamic stability metric or the hemodynamic concordance metric can be used to determine whether the detected arrhythmia is hemodynamically stable. If so, an ATP therapy can be generated, such as by the therapy generation circuit 135, and flow continues to 1430 to determine whether the arrhythmia condition is still present. Returning to 1460, if the detected arrhythmia is not hemodynamically stable, then flow continues to 1480 and a defibrillation shock can be generated, such as by the therapy generation circuit 135.

Figure 15:
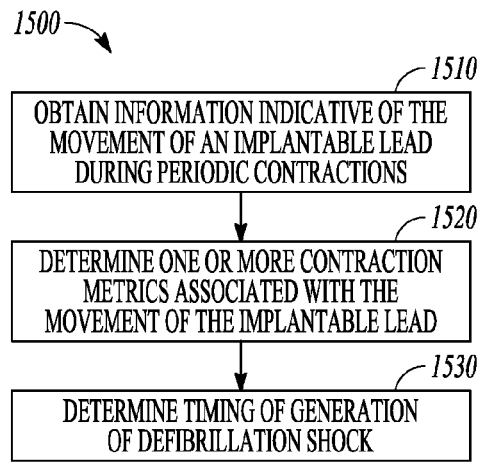
FIG. 15 illustrates generally a technique for adjusting a therapy using information indicative of the movement of the implantable lead.

FIG. 15 illustrates generally an example of a technique 1500 for analyzing information indicative of the motion of an implantable lead, such as included in the IMD of one or both of FIGS. 1, 2, and 9. At 1510, the information indicative of the motion of the implantable lead 145 can be obtained such as by the processor circuit 190, such as to analyze at least a portion of a mechanical contraction waveform indicative of a mechanical contraction (e.g., a portion of the mechanical contraction waveform including peak information). At 1520, one or more mechanical contraction metrics can be determined from one or more mechanical contraction waveforms, such as by the processor circuit 190. At 1530, the one or more mechanical contraction metrics can be analyzed such as by the therapy adjustment circuit 171 such as to determine the timing for delivery of a defibrillation shock.

Figure 16:
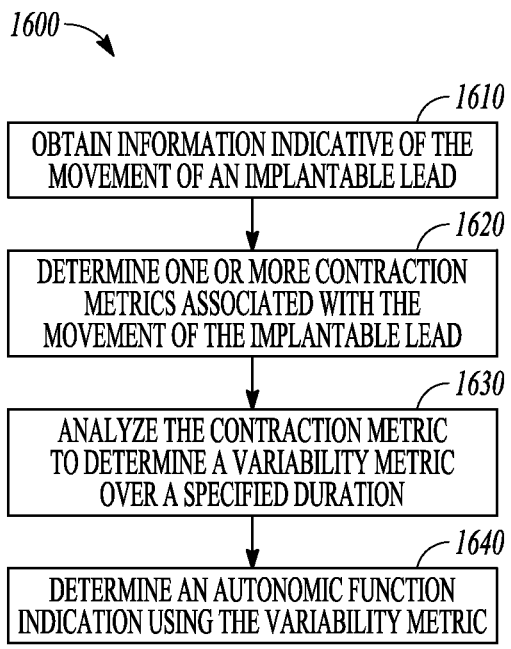
FIG. 16 illustrates generally a technique for determining an autonomic function indication using information indicative of the movement of the implantable lead.

FIG. 16 illustrates generally an example of a technique 1600 for analyzing information indicative of the motion of an implantable lead, such as included in the IMD of one or both of FIGS. 1, 2, and 9. At 1610, the information indicative of the motion of the implantable lead 145 can be obtained such as by the processor circuit 190, such as to analyze at least a portion of a mechanical contraction waveform indicative of a mechanical contraction (e.g., a portion of the mechanical contraction waveform including peak information). At 1620, one or more mechanical contraction metrics can be determined from one or more mechanical contraction waveforms, such as by the processor circuit 190. At 1630, the one or more mechanical contraction metrics can be analyzed such as by the autonomic function monitor circuit 161 to determine a variability metric over a specified duration of the one or more mechanical contraction metrics. At 1640, the variability metric can be analyzed over a duration such as to determine an indication of the autonomic function of the subject, where a higher variability metric can be associated with an improved physiological condition.

Figure 17:
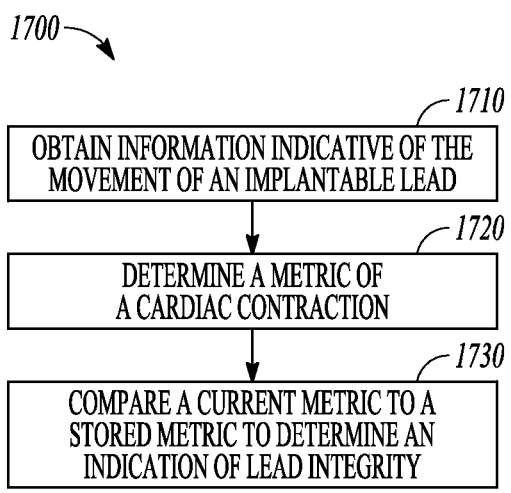
FIG. 17 illustrates generally a technique for determining a lead status indication using information indicative of the movement of the implantable lead.

FIG. 17 illustrates generally an example of a technique 1700 for analyzing information indicative of a vibration of an implantable lead, such as included in the IMD of one or both of FIGS. 1, 2, and 9. At 1710, the information indicative of the motion of the implantable lead 145 can be obtained such as by the processor circuit 190, such as to analyze at least a portion of a mechanical contraction waveform indicative of a mechanical contraction (e.g., a portion of the mechanical contraction waveform including peak information). At 1720, one or more mechanical contraction metrics, including magnitude information, can be determined from one or more mechanical contraction waveforms, such as by the processor circuit 190. At 1730, a contraction metric obtained over a current duration can be compared to one or more contraction metrics obtained previously, such as to determine an indication of lead integrity. For example, if the difference between the current contraction metric and the one or more previous contraction metrics is greater than a threshold, the processor 190 can indication that the lead is aging.

Additional Examples

Generally, a healthy heart can provide at least two distinct heart sounds. The first sound, "S1," is typically produced by the closing of the atrioventricular valve leaflets. The second sound, "S2," is typically produced by the closing of the semilunar valve leaflets. In a clinical setting, these events can be detected such as through cardiac auscultation by an examiner, using a stethoscope.

In some individuals, various cardiac conditions can cause additional detectable mechanical vibrations, though these may or may not be audible to the examiner. For example, a heart murmur can occur when blood is flowing harder or faster than in an otherwise healthy individual. Such a murmur can indicate a serious heart problem or merely a benign cardiac event. In another example, an "S3" sound, also known as a protodiastolic gallop, can indicate a failing left ventricle. An "S4" sound, also known as presystolic gallop, can sometimes be detected in patients exhibiting restrictive cardiomyopathy.

In addition to vibrations or sounds indicative of heart function, blood flowing through blood vessels can also produce detectable vibrations useful for diagnosis and assessment of various medical conditions. The location, velocity, and pressure of blood flow are variables that can be assessed by detection of such vibration, among other variables. Thus, mechanical vibration monitoring capabilities can be included in an implantable or an ambulatory medical device, such as to store such information for later review or analysis, or to respond to such mechanical information. For example, an individual with an implantable medical device, such as a pacemaker, can benefit from mechanical vibration monitoring, including heart sound monitoring. Such monitoring can be used for diagnosis, or an initiation or adjustment of treatment. By identifying a mechanical vibration (e.g., including one or more heart sounds), therapy can be tailored to an individual's needs, or heart sound abnormalities can be provided to a caregiver for assessment or treatment.

Implantable acoustic and mechanical transducers can be used in detecting heart and blood mechanical vibrations (e.g., including one or more heart sounds). However, the resulting acoustic information from these transducers can produce a low signal level that can be degraded by extraneous noise. Furthermore, devices having a dedicated acoustic or mechanical transducer can require additional sensors within, on, or attached to the implantable or ambulatory device, such as resulting in a greater surface area, physical volume, or number of interconnects as compared to a comparable implantable device lacking such a dedicated acoustic or mechanical transducer.

The present inventor has recognized, among other things, that mechanical information indicative of cardiac, blood, or vascular motion can be detected using a motion of one or more conductors electrically coupled to the ambulatory or implantable device. For example, the present inventors have also recognized that an implantable lead electrically and mechanically tethered to an implantable or ambulatory medical device can provide information indicative of the motion of the lead, such as using one or more electrical measurements as described in the following examples, such as to detect cardiac, blood, or vascular motion. Such information indicative of motion can also be used to time or to verify the effectiveness of a cardiac therapy (e.g., electrostimulation), in addition to diagnosing one or more cardiac conditions.

An ambulatory medical device can include an excitation circuit configured to be electrically coupled to an implantable lead, the excitation circuit configured to provide a non-tissue-stimulating first signal to the implantable lead when the implantable lead is located at or near a tissue site. In an example, the system can include a detection circuit configured to be electrically coupled to the implantable lead and configured to receive a second signal, in response to the first signal, from the implantable lead, the second signal determined at least in part by a motion of the implantable lead.

Figure 18:
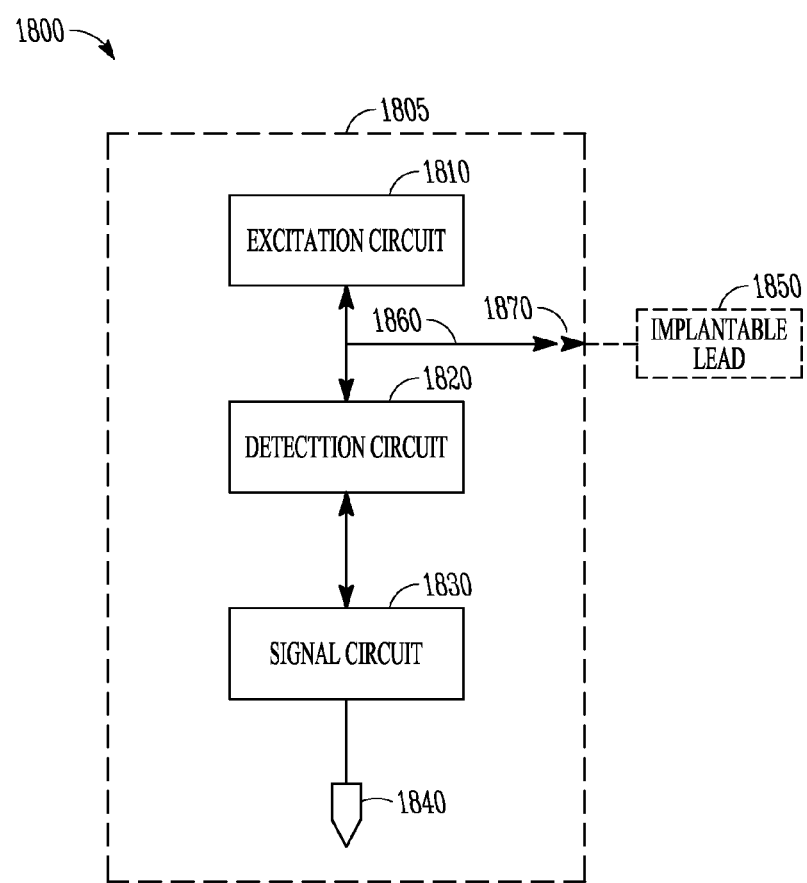
FIG. 18 illustrates generally an example of a system comprising an ambulatory medical device that can include an excitation circuit, a detection circuit, a coupling to an implantable lead, a signal processor, or an output.

FIG. 18 is a diagram illustrating generally an example of a system 1800 comprising an ambulatory medical device 1805 that can include an excitation circuit 1810, a detection circuit 1820, a signal processor 1830, an output 1840, an interconnect 1860, or a lead coupling 1870. In an example, an implantable lead 1850 can be coupled to the lead coupling 1870. One or more of the excitation circuit 1810, detection circuit 1820, signal processor 1830, output 1840, or interconnect 1860 can be realized on or within a commonly shared substrate, such as on a commonly-shared integrated circuit, module, circuit board, or the like. In another example, each block can be included in a physically separate ambulatory device, such devices coupled as shown in the example of FIG. 18, such as using one or more wired or wireless communicative couplings.

In the example of FIG. 18, the ambulatory medical device 1805 can include a cardiac stimulator, such as including pacing or cardiac resynchronization therapy (CRT) circuitry configured to deliver pacing or resynchronization energies to cardiac tissue. In an example, the ambulatory medical device 1805 can include a neural stimulator device, such as to provide electrical, mechanical, optical, acoustic or chemical stimulation to one or more neural targets.

In the example of FIG. 18, the excitation circuit 1810 can be coupled to a detection circuit 1820. The excitation circuit 1810 generally provides an excitation energy, such as including a first signal. In an example, the first signal can include an oscillating electrical signal, such as a time-varying voltage or current. In an example, the first signal can include a pulsed electrical signal, such as including one or more current or voltage pulses including a specified amplitude, duration, pulse repetition rate, duty cycle, or morphology, among other parameters. In an example, the excitation circuit 1810 can be coupled to the lead coupling 1870 via interconnect 1860, such as using a header or other connector included as a portion, part, or component of the medical device 1805.

In the example of FIG. 18, an implantable lead 1850 can be coupled to the lead coupling 1870. For example, the implantable lead 1850 can include one or more conductors. In an example, the implantable lead 1850, such as coupled to the implantable lead coupling 1870, can be located at a site within or on the body (e.g., including one or more surface, subcutaneous, or intravascularly-located electrodes or conductors). In an example, the implantable lead 1850 can be implanted or otherwise place within a body, such as within or near a heart, either temporarily or more permanently, such as for ambulatory monitoring or therapy delivery.

In the example of FIG. 18, the detection circuit 1820 can be coupled both to a signal processor 1830 and the lead coupling 1870 via a commonly-shared interconnect 1860. In an example, the implantable lead 1850, or an external lead, can be coupled to the lead coupling 1870. In an example, the detection circuit 1820 can be configured to receive a second signal provided by the implantable lead 1850. For example, the detection circuit 1820 can be configured to interpret or processes the first signal, such as by providing the first signal to the implantable lead 1850 before or during receiving the second signal.

In the example of FIG. 18, the detection circuit 1820 can be configured to receive a second signal, such as from the implantable lead 1850 via the lead coupling 1870 and the interconnect 1860 (e.g., in response to the first signal). In an example, the detection circuit 1820 can be configured to interpret and process a received second signal before transmitting the received second signal to the signal processor 1830. For example, the detection circuit 1820 can be configured to determine a first characteristic of the second signal (e.g., information about an amplitude, frequency, noise floor, signal-to-noise ratio, or one or more other characteristics). In an example, the amplitude characteristic of the second signal can be compared to a threshold value, and the result of the comparison can be used to determine if the received second signal can be further processed by the signal processor 1830. For example, if the amplitude of the second signal meets or exceeds a threshold value, the detection circuit 1820 can be configured to transmit the second signal to the signal processor 1830 for further analysis. Conversely, if the amplitude of the second signal is below the threshold value, the detection circuit can withhold transmission of the second signal or otherwise indicate to the signal processor 1830 that further analysis should be withheld (e.g., if the second signal is so low in amplitude that extraction of motion information would be difficult).

In the example of FIG. 18, the signal processor 1830 can be coupled to the detection circuit 1820 and the output 1840. In an example, the signal processor 1830 can be configured to receive information derived from the second signal. The signal processor 1830 can be configured to extract from the second signal information indicative of motion of the implantable lead 1850. Such motion of the implantable lead 1850 can include a physical displacement of any constituent element of implantable lead 1850 with respect to an equilibrium position. In an illustrative example, the implantable lead 1850 can experience a physical displacement because the implantable lead is mechanically coupled to a vibrating tissue, such as implanted within or near contractile tissue in the heart. In an example, the information indicative of motion of the implantable lead 1850 can include audible or acoustic information such as provided by a heart sound, or other higher or lower-frequency mechanical information not necessarily within the audible frequency spectrum.

In an example, information indicative of motion of the implantable lead 1850 can include impedance information, such as including a change in lead impedance determined at least in part by mechanically coupling cardiac or vascular mechanical vibrations to the implantable lead 1850. For example, impedance information can be interpreted by the signal processor 1830 to detect, classify, or monitor one or more physiological events. Such physiological events can include the closing of the atrioventricular or semilunar valve leaflets in the heart.

In the example of FIG. 18, the output 1840 can be coupled to the signal processor 1830. In an example, the output 1840 can receive information from the signal processor 1830. The received information can be passed through an output 1840 to one or more other portions, parts or components of the ambulatory medical device 1805. In an example, the output 1840 can be coupled to another device via a wired or wireless communicative connection (e.g., to transfer information to one or more other implantable or ambulatory devices, or to an external assembly). In an example, the signal processor 1830 can perform one or more signal adjustments such as impedance or level adjustments, among others, before providing the lead motion information to the one or more other portions via the output 1840.

Figure 19:
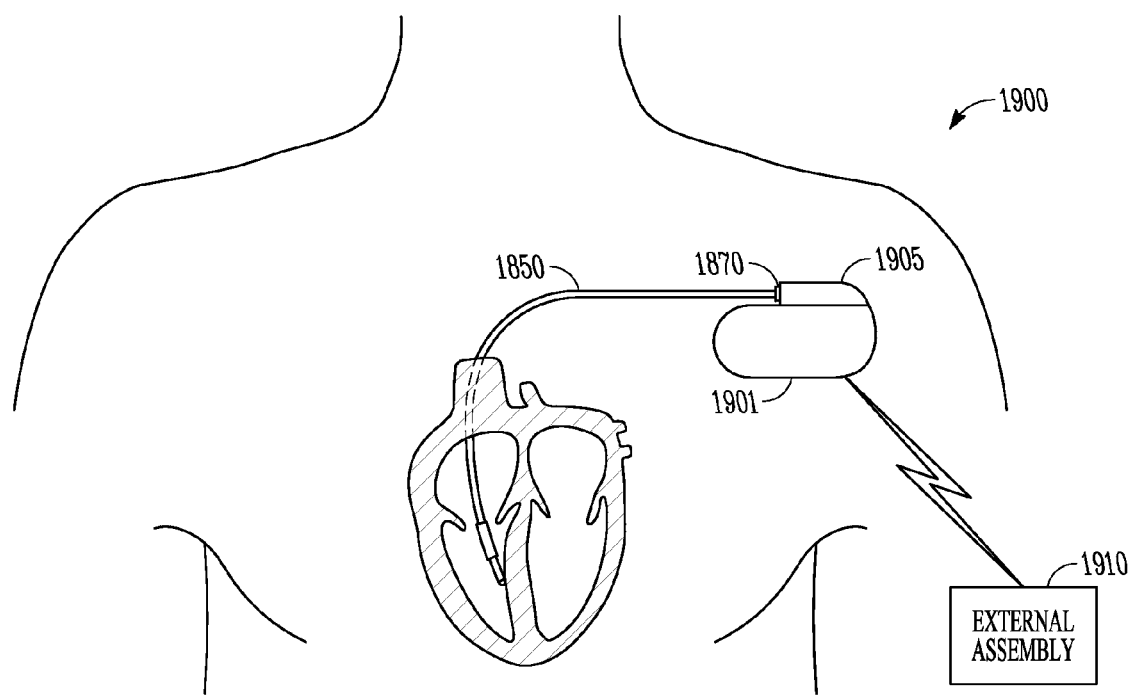
FIG. 19 illustrates generally an example of a portion of a system that can include an implantable medical device, an implantable lead, or a communicative coupling between the implantable medical device and an external assembly.

FIG. 19 illustrates generally an example of a system 1900 that can include an implantable medical device 1905. In this example, the implantable medical device 1905 can include one or more implantable lead couplings, such as a lead coupling 1870. In certain examples, the implantable medical device 1905 includes a hermetically-sealed or similar housing 1901 coupled to the implantable lead coupling 1870. For example, the housing 1901 can include titanium or other biocompatible material, such as one or more other conductive materials.

In the example of FIG. 19, the system 1900 can include an implantable lead 1850 implanted in a heart, such as implanted endocardially via an intravascular route from one or more of a subclavian vein or a femoral artery. In an example, the implantable lead 1850 can include one or more conductors, such as one or more concentric or laterally-separated conductors. In an example, one or more conductors can include a braided or coiled shield conductor. The one or more conductors can be insulated from one another and from the environment surrounding the implantable lead 1850, such as using a silicone or a poly-ether-ether-ketone (PEEK) insulation, among others. In an example, the conductors to be used for mechanical vibration sensing can be selected based on measurement of RF coupling or an AC impedance between the conductors. Such RF coupling or impedance measurements can be used to determine a conductor pair or combination likely to exhibit higher mechanical vibration sensitivity than other pairs or combinations. Such measurements can also be used to find a conductor pair or combination including an input impedance most closely matched to a conjugate of the output impedance of one or more of a detection circuit, excitation circuit, or interconnect as shown in FIG. 18, and FIGS. 20-22.

In an example, the implantable medical device 1905 can be configured to communicate with the external assembly 1910. The communication between the implantable medical device 1905 and an external assembly 1910 can be wireless or through a wired connection, or using one or more other communication schemes (e.g., using an optical communication link or an acoustic communication link, among others). For example, the external assembly 1910 can be a portion or part of a patient management system, such as including or in communication with one or more remote or web-based clients communicatively coupled to one or more servers comprising medical and patient databases.

In an example, the implantable medical device can include one or more of a pacemaker, a defibrillator, an implantable monitor, a drug delivery device, a cardiac resynchronization therapy device, a neural stimulation device, or one or more other implantable assemblies configured to monitor a person or configured to provide one or more treatments to the person. Such monitoring or treatment can include, among others, electrostimulation of tissue such as cardiac tissue, or electrical monitoring of muscular or cardiac activity, among others.

Figure 20:
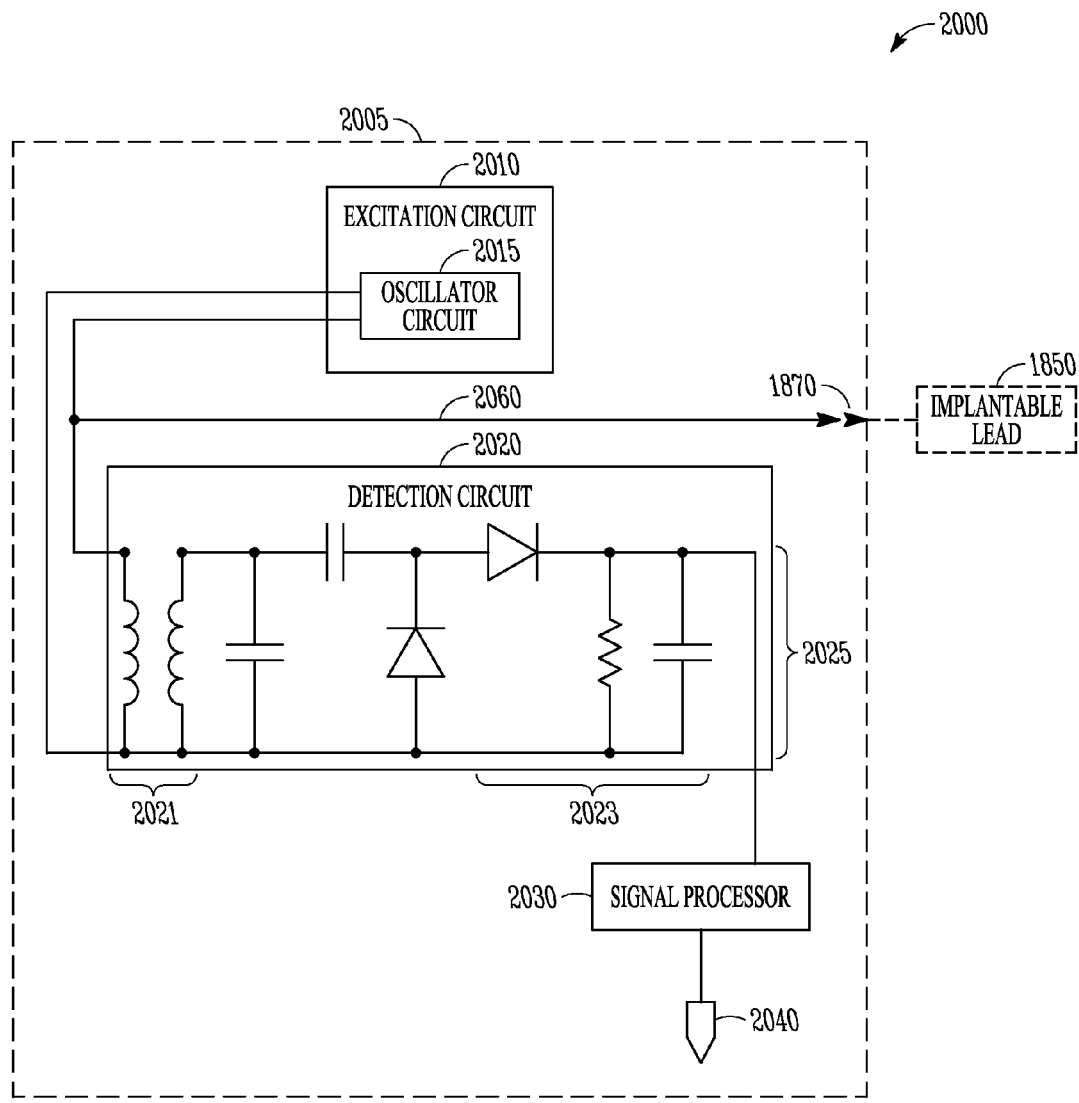
FIG. 20 illustrates generally an example of a portion of a system comprising an excitation circuit that can include an oscillator circuit, a detection circuit, a coupling to an implantable lead, a signal processor circuit, or an output.

FIG. 20 illustrates generally an example of a system 2000 that can include an ambulatory medical device 2005, such as including an implantable device as shown in the example of FIG. 19, an externally-worn assembly, or a combination of implantable and external portions. In this example, an excitation circuit 2010 can include an oscillator circuit 2015 such as configured to provide a first signal. In an example, the oscillator circuit can provide an RF signal (e.g. from about 180 to about 30 megaHertz), such as including a specified current level.

In an example, an interconnect 2060 can be coupled to one or more of the excitation circuit 2010 or a detection circuit 2020. In this example, the first signal (e.g., an excitation current signal) can be provided by the excitation circuit 2010 to develop a voltage across two conductors included in the lead coupling 1870 via the interconnect 2060. For example, the first signal can include one or more current signals provided to one of the conductors, and received from the other conductor. The detection circuit 2020 can be configured to receive a second signal (e.g. a developed voltage) across the lead coupling 1870.

In an example, the detection circuit 2020 can include a demodulation circuit 2025. The demodulation circuit 2025 can include an envelope detector 2023 or a tuned resonant transformer 2021 that can be impedance-matched to one or more other attached components. In an example, the envelope detector 2023 can demodulate or extract a relatively low frequency component of time-varying voltage from the second signal, such as containing information indicative of motion of an implantable lead 1850 attached to the lead coupling 1870. The demodulation circuit 2025 can be coupled to a signal processor 2030. In an example, the signal processor 2030 can be configured to extract information indicative of motion of the implantable lead 1850, such as including protodiastolic or presystolic gallop sounds, or other mechanical vibrations such as indicative of blood flow, or pressure, among others.

In an example, additional elements can be included in the system 2000 to enhance sensitivity or provide additional mechanical event information. For example, multiple implantable leads can be implanted in multiple locations within or on a body and lead motion information can be collected from one or more of the multiple locations. For example, a second lead comprising at least one electrical conductor can be coupled to a second lead coupling, or the implantable lead 1850 can include multiple electrical conductors that can be coupled to one or more lead couplings. In an example, one or more mechanical events can provide a change in the impedance of the system comprising the multiple conductors, such as detectable using the second signal provided in response to the first signal. In an example, the signal processor 2030 can be coupled to an output 2040, and extracted information indicative of motion of the implantable lead 1850 can be communicated to another assembly via the output 2040. Such other assemblies can include, among others, an additional ambulatory medical device located internally or externally to a body, or an external assembly 1910, a combination of one or more implantable and external assemblies.

Figure 21:
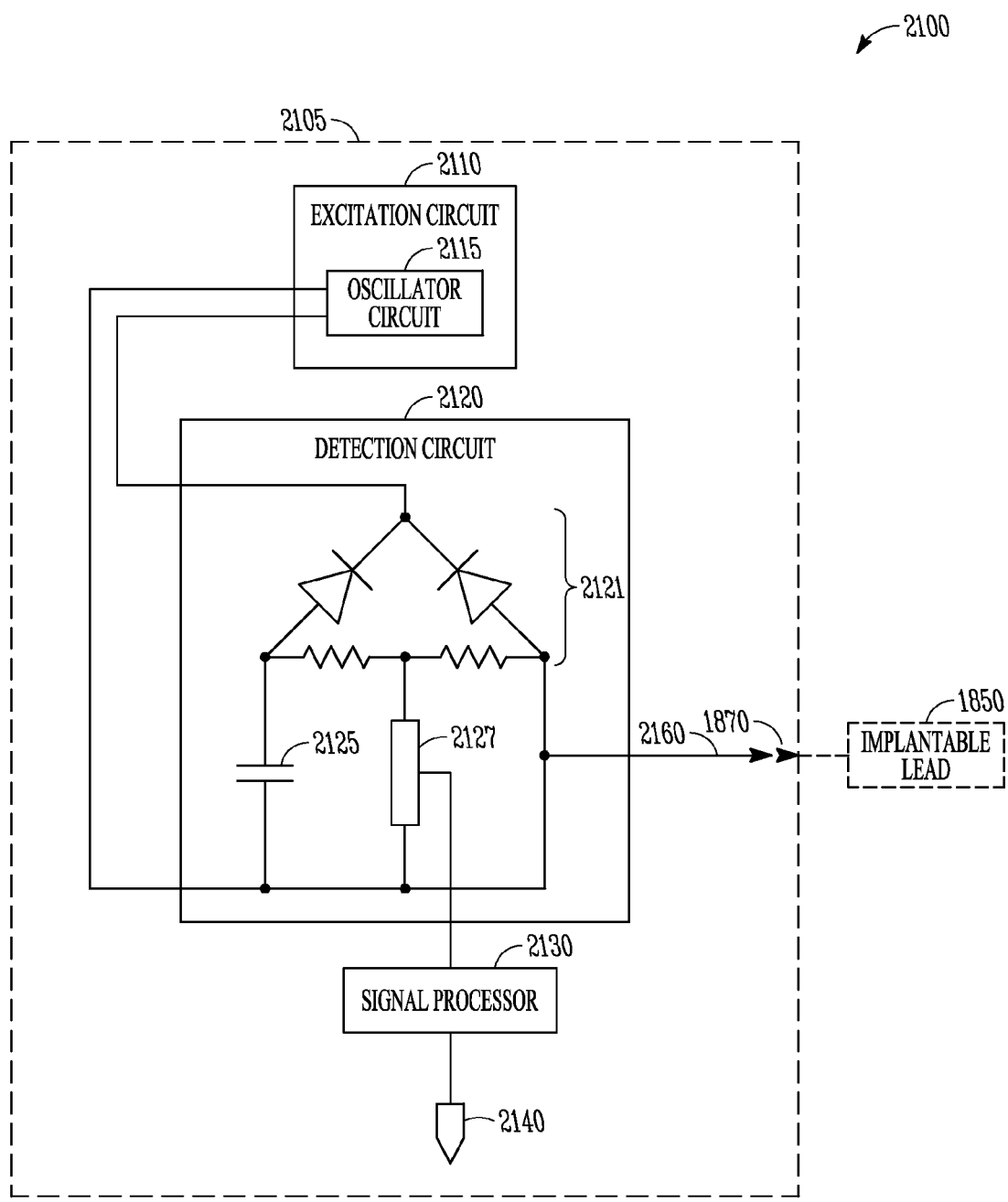
FIG. 21 illustrates generally an example of a portion of a system comprising an excitation circuit that can include an oscillator circuit, a detection circuit comprising a coupling to an implantable lead and a bridge circuit, a signal processor circuit, or an output.

FIG. 21 illustrates generally an example of a system 2100 including ambulatory medical device 2105, such as including an implantable device as shown in the example of FIG. 19, an externally-worn assembly, or a combination of implantable and external assemblies. In this example, an excitation circuit 2110 can include an oscillator circuit 2115 configured to provide a first signal, such as provided to a portion of a detection circuit 2120. In an example, an interconnect 2160 can be coupled to the detection circuit 2120. The detection circuit 2120 can include a bridge circuit 2121, a capacitive element 2125, or an envelope detector 2127, among other components or portions. In the example of FIG. 21, the sensitivity of detection circuit 2120 can vary with respect to a specified excitation frequency. In an illustrative example, the oscillator circuit 2115 can provide a first signal including a sine wave signal with a frequency of around 100 kiloHertz to 1 megaHertz (or including one or more other frequencies). The bridge circuit 2121 can include one or more diodes or other rectifiers exhibiting low forward resistance, such as one or more germanium diode (e.g. type 1N60). In this example, the bridge circuit 2121 can include resistors of about the same values. The implantable lead 1850 can provide a capacitance, and the capacitive element 2125 can include a specified capacitance value approximately equal to the capacitance provided by the implantable lead 1850 when implantable lead 1850 is in equilibrium (e.g., relatively motionless, or subject to a specified baseline of vibration or motion). The capacitance provided by the implantable lead 1850 can be one or more capacitances provided between two or more conductors, such as included in a single implantable lead 1850, or between conductors respectively included in two or more implantable leads. Generally, the one or more capacitances can be provided by a combination of multiple conductors, and such capacitances can be combined in a series or parallel configuration, such as each including a capacitance contribution from one or more pairs of conductors. In an example, the capacitance can be provided between conductors of physically separate implantable leads. Such lead capacitance can vary in proportion or with respect to motion or vibration coupled to the lead such as from surrounding tissue or blood motion. In an example, the envelope detector 2127 can include a relatively high input impedance to achieve a specified sensitivity of the system 2100. The envelope detector 2127 can include one or more of a diode or rectifier detector, or a synchronous detector, such as to improve noise rejection, selectivity, or one or more other characteristics.

In an example, a signal processor 2130 can be configured to receive a signal from the detection circuit 2120, such as provided at least in part by the envelope detector 2127. For example, the signal processor 2130 can be configured to extract information from the received voltage signal indicating a motion of an implantable lead 1850. In an example, the signal processor 2130 can include a low pass filter circuit to process the signal received from the detection circuit 2120. In an example, the signal processor 2130 includes an amplification circuit, or one or more other circuits or components, such as to amplify the received signal. In an example, the signal processor 2130 can include an analog-to-digital converter to convert the information indicative of motion into a digital data signal, such as for storage, further processing, or for presentation to a caregiver or clinician.

In an example, an output 2140 can be configured to receive a signal from the signal processor 2130, and the output 2140 can be configured to transfer the information indicative of motion of the implantable lead 1850 to another implantable or ambulatory medical device, or to an external assembly such as the external assembly 1910 using a wireless or wired communicative coupling. In an example, the output 2140 can be configured to communicate with one or more external assemblies including one or more tabletop or handheld electronic devices (e.g. a cell phone, smart phone, tablet, laptop, or personal digital assistant (PDA), among others), in addition to or instead of one or more external assemblies dedicated for medical diagnosis or assessment.

In an illustrative example, one or more of the detection circuit 2120 or the signal processor 2130 can receive a second signal in response to the first signal, and the second signal can include a portion in-phase with the first signal, and a second portion in quadrature (e.g., ninety degrees out of phase) with the first signal. In this illustrative example, the detection circuit 2120 or the signal processor 2130 can use the quadrature component of the second signal to determine the change in capacitance of the lead system, thus canceling out the effect of the resistive component of an impedance presented by the lead 1850 to the measurement circuit.

Figure 22:
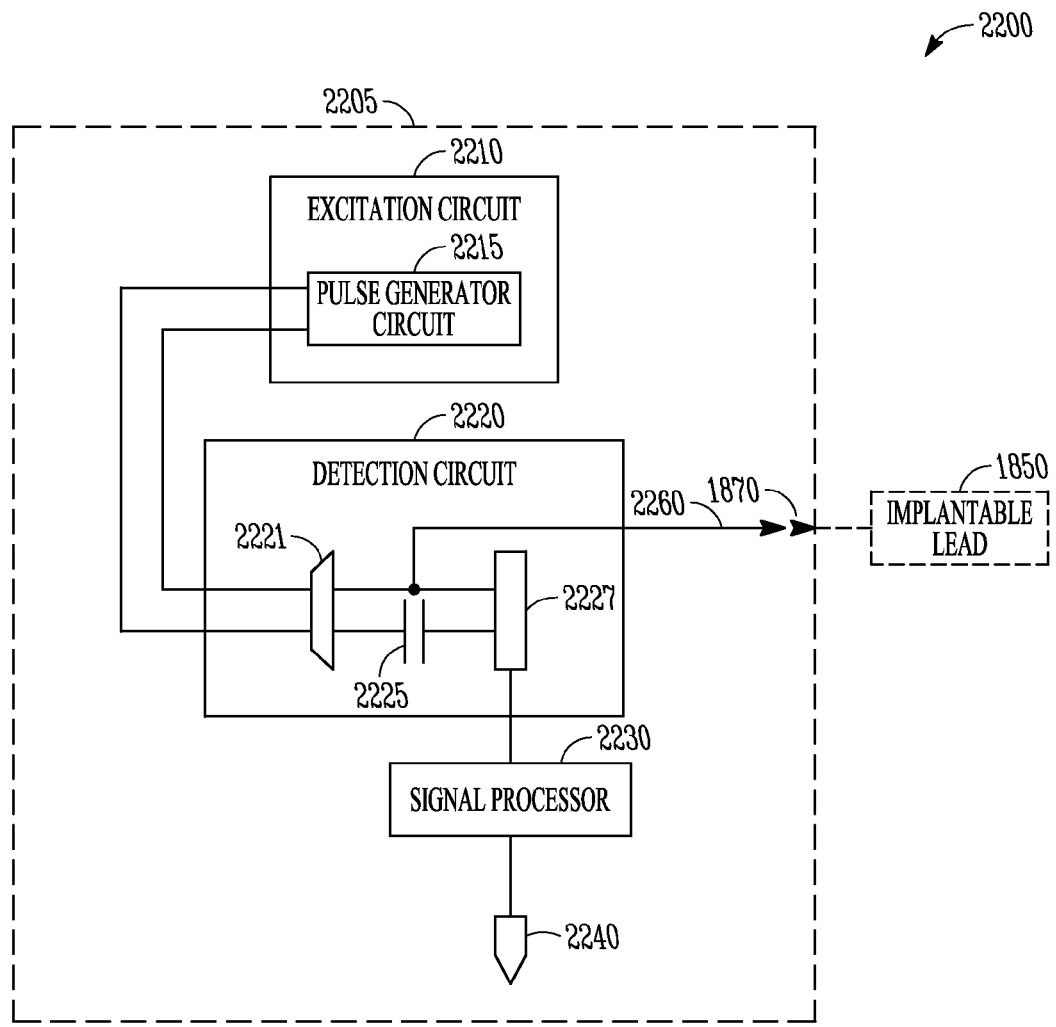
FIG. 22 illustrates generally an example of a portion of a system that can include an excitation circuit such as including a pulse generator circuit, a detection circuit including a coupling to an implantable lead and a voltage detector, a signal processor circuit, or an output.

FIG. 22 illustrates generally an example of a system 2200 including ambulatory medical device 2205, such as including an implantable device as shown in the example of FIG. 19, or an externally-worn assembly. In this example, an excitation circuit 2210 can include a pulse generator circuit 2215 configured to provide a first signal, and a detection circuit 2220. In an example, the detection circuit 2220 can include a multiplexer 2221, a capacitive element 2225, or a voltage detector 2227. In an example, the multiplexer 2221 can be configured to select among one or more inputs, wherein the inputs can be coupled to the excitation circuit 2210, or another signal-generating source. In an example, the multiplexer 2221 can be under the control of the detection circuit 2220 or another component of the ambulatory medical device 2205. An interconnect 2260, the voltage detector 2227, or a lead coupling 1870, among other components, can be coupled to the multiplexer 2221.

One or more portions of the system 2200, such as the interconnect 2260, multiplexer 2221, or voltage detector 2227, can be implemented on a rigid or flexible circuit board, such as including one or more application specific integrated circuits, among other components. In an example, the lead coupling 1870 can be implemented via an electrical and mechanical interconnect in a header block that can be attached to the housing 1901 of an implantable medical device housing, such as shown in FIG. 19. The housing 1901 of the implantable medical device itself can be used as one of the conductors for capacitance or impedance measurement.

In an example, the excitation circuit 2210 can be coupled to the multiplexer 2221. In an example, the multiplexer 2221 can be configured to couple the excitation circuit 2210 to each of the interconnect 2260 and the capacitive element 2225, concurrently or successively. In an example, the concurrent or successive coupling can be performed by the multiplexer 2221 under the direction of a logic circuit included as a portion of the detection circuit 2220. For example, the logic circuit can include a counter or timer such as to provide one or more counts or durations to be used by the logic circuit to switch the state of the multiplexer 2221, such as after a specified duration of time elapses as indicated by the counter or timer. In an example, the logic circuit can be configured to count a number of pulses provided by the excitation circuit 2210. In this example, the logic circuit can be configured to switch the state of the multiplexer 2221, such as after a specified count of a number of pulses is met or exceeded as indicated by the counter.

In the example of FIG. 22, the multiplexer 2221 can be configured to couple the first signal to a first capacitance provided by implantable lead 1850. In an example, a first voltage can be developed across the first capacitance in response to the first signal. A second signal that includes the first voltage can be received by the voltage detector 2227. In this example, a signal processor 2230 can receive the output of the voltage detector 2227. In an example, the signal processor 2230 can be configured to compare the received signal from the first capacitance to a threshold voltage (e.g., monitoring a charging of the first capacitance to reach the specified threshold voltage).

In the example of FIG. 22, the multiplexer 2221 can be configured to couple the first signal to a second capacitance provided by the capacitive element 2225 (e.g., a "reference capacitance," charged using the same or a similar first signal). In an example, the multiplexer 2221 can be configured to provide the first signal to each of the first capacitance and second capacitance, either separately, sequentially, or in combination. In an example, a second voltage can be developed across the second capacitance in response to the first signal. In an example, the second signal that includes the second voltage can be received by the voltage detector 2227. In this example, a signal processor 2230 can receive the output of the voltage detector 2227. In an example, the signal processor 2230 can be configured to compare the received signal from the second capacitance to the specified threshold voltage (e.g., monitoring a charging of the second "reference" capacitance to reach the specified threshold voltage).

In the example of FIG. 22, the signal processor 2230 can be configured to determine a relative indication of information (e.g., a ratio, a difference, etc.) derived from one or more of the first or second voltages measured with respect to the first or second capacitances. Coupling of mechanical vibration to the implantable lead 1850, or other motion of the lead, can cause a detectable change in the capacitance of the lead. For example, the second signal received from the first capacitance can differ from the second signal received from the second capacitance in response to a similar excitation by the first signal. In this manner, a variation between a reference capacitance (e.g., provided by capacitive element 2225) and the capacitance of the lead can be used to provide information corresponding to motion of the implantable lead. In an example, capacitive element 2225 can include, among other things, an additional specified capacitance such as provided by a discrete capacitor, a second implantable lead or combination of conductors, a number of interconnected implantable leads, or a capacitive transducer.

In the example of FIG. 22, the first signal can charge the first capacitance to a first specified threshold voltage, and a corresponding duration of the charge time can be determined (e.g., such as when the first capacitance is charged using a sequence of current pulses or a constant current). In an example, the voltage detector 2227 can be configured to receive the first voltage in response to the charging of the first capacitance. In this example, the signal processor 2230 can be configured to determine a duration of a first charge time, corresponding to a duration where the first voltage is between a lower threshold (e.g., around 0 Volts), and an upper threshold (e.g., the first specified voltage threshold). In an example, the signal processor 2230 can be configured to determine a duration of a second charge time, corresponding to a duration where the second voltage is between the lower and upper thresholds. If the capacitance of the capacitive element 2225 and the lead capacitance are roughly equal, the determined first and second charge times can be roughly equal, such as when the lead 1850 is at rest or equilibrium.

In the example of FIG. 22, the excitation signal (e.g., the first signal), can include a series of current pulses having a specified peak current level, duration, pulse repetition rate, duty cycle, etc. The signal processor 2230 can be configured to count a number of pulses delivered to the lead 1850, or to a capacitive element 2225. For example, the voltage detector 2227 can be configured to receive pulsed signals and the signal processor 2230 can be configured to count the received pulsed signals. In an example, the signal processor 2230 can be configured to count a first count of a number of pulses provided to the first capacitance, such as to reach the specified threshold voltage (e.g., the pulse count can be a proxy for a measurement of a charge time duration, such as when pulses of determinable width and level are used). In an example, the signal processor 2230 can be configured to extract from the first count an indication of lead motion, since the variation in the lead capacitance can provide a difference in a number of pulses needed to reach the specified threshold, such as compared with a baseline number of pulses corresponding to a lead at rest or in equilibrium.

In an example, the sensitivity of the system 2200 can be enhanced by using a comparison between a second capacitance (e.g., a reference capacitance or another pair or combination of lead conductors) and the capacitance of the lead 1850. The signal processor 2230 can be configured to count a second count of a number of pulses provided to the second capacitance (e.g., using a series of pulses of determinable width or level, as above). For example, the signal processor 2230 can be configured to extract from the first and second counts a relative indication of information that can indicate lead motion (e.g., a difference, or ratio, etc., between the first and second counts of pulses). In an illustrative example, the signal processor 2230 can measure multiple pulse durations and perform comparison operations, such as including using one or more techniques disclosed in Pelletier et al. U.S. Pat. No. 4,011,500 entitled "PHYSICAL DISPLACEMENT SENSING WITH DIFFERENTIAL CAPACITOR," which is hereby incorporated by reference in its entirety, including its disclosure of using a differential capacitor to detect a physical displacement.

In an example, an output 2240 can be configured to receive information from the signal processor 2230, and to transfer such information to one or more other portions of the ambulatory medical device 2205, or to communicate with an external assembly.

Figure 23:
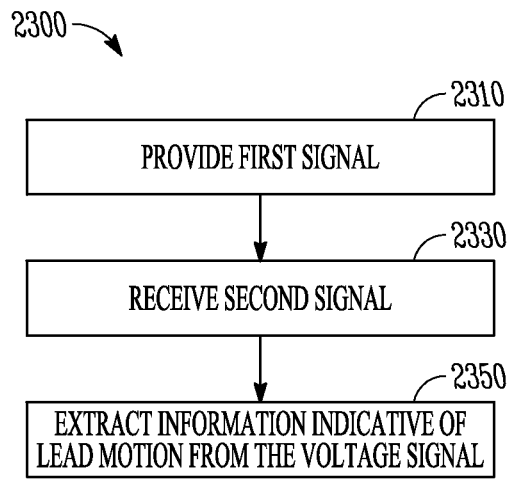
FIG. 23 illustrates generally an example that can include providing a first signal, receiving a second signal, or extracting information indicative of lead motion from the second signal.

FIG. 23 illustrates generally an example 2300 that can include providing a first signal, receiving a second signal, or extracting information indicative of lead motion from the second signal, such as using circuitry or techniques as discussed above in the examples of FIGS. 18-22.

At 2310, a first signal can be provided to excite the ambulatory medical device 1805. In an example, the first signal can be a non-tissue-stimulating electrical signal. For example, the first signal can be an AC signal generated or provided by an excitation circuit 1810. In an example, the first signal can be provided to an implantable lead 1850.

At 2330, a second signal can be received in response to the first signal. In an example, the detection circuit 1820 can be configured to receive the second signal from the implantable lead 1850. In an example, the second signal can include, among other signals, a phase-shifted or modulated version of the first signal, a voltage signal, a logic signal, or a data signal including information indicative of motion of the implantable lead.

At 2350, information can be extracted from the second signal. The extracted information can indicate motion of the implantable lead 1850. In an example, the information can indicate a relative or absolute indication of a displacement of the implantable lead 1850. In an example, the information can include an electrical representation of mechanical vibration or motion coupled to the lead, such as including a heart sound, a blood pressure sound, or respiratory sound, among others.

Figure 24:
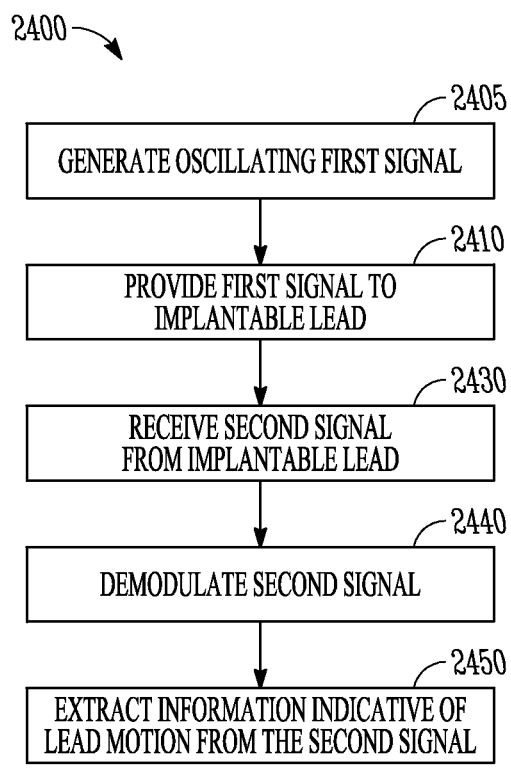
FIG. 24 illustrates generally an example that can include generating an oscillating first signal, providing the first signal to an implantable lead, receiving a second signal from the implantable lead, demodulating the second signal, or extracting information indicative of lead motion from the second signal.

FIG. 24 illustrates generally an example 2400 that can include generating an oscillating first signal, providing the first signal to an implantable lead, receiving a second signal from the implantable lead, demodulating the second signal, or extracting information indicative of lead motion, such as using circuitry or techniques discussed above with respect to FIGS. 18-22.

At 2405, a first signal can be generated by an oscillator circuit included in an excitation circuit 1810. In an example, the oscillator circuit can include a Colpitts oscillator. In an example, the first signal can include an AC signal and the frequency of oscillation can be tunable such as to achieve a specified sensitivity.

At 2410, the first signal can be provided to the implantable lead 1850, such as via an interconnect 2060 and a lead coupling 1870. In an example, the first signal can be coupled through a series capacitor with high DC or near-DC impedance to create a relatively constant current signal into the implantable lead 1850. In an example, a change in capacitance of the implantable lead 1850 can modulate the impedance of the circuit comprising the implantable lead 1850, the lead coupling 1870, and the interconnect 2060.

At 2430, a second signal can be received from the implantable lead 1850, such as in response to the first signal. In an example, the modulated impedance of the circuit comprising the implantable lead 1850, the lead coupling 1870, and the interconnect 2060 can produce the second signal in response to the first signal such that the second signal can be different than the first signal.

At 2440, the second signal can be demodulated to recover the information indicative of lead motion. In an example, the second signal can be received by a detection circuit 2020 wherein a demodulation circuit 2025 can be used to demodulate the received second signal. The demodulation circuit 2025 can include a tuned resonant transformer 2021 or an envelope detector 2023, wherein the transformer 2021 can be configured to provide an impedance-matched coupling between the second signal and the envelope detector. In an example, the second signal can include a voltage that can be detected between conductors in the implantable lead 1850, including a voltage that can include a phase-shifted version of the first signal. In this example, information indicative of lead motion can be realized by extracting a relatively low frequency component of a time-varying voltage from the second signal using the envelope detector 2023. In an example, the second signal comprises a large DC voltage with a small AC voltage superimposed, wherein the AC voltage can result from the response of the first signal to the modulated impedance. In an example, the implantable lead 1850 can be implanted in a heart and provided with the first signal. In this example, the resulting AC component of the second signal can include information about heart wall motion (or information indicative of one or more other mechanical vibrations coupled to the lead 1850).

At 2450, information can be extracted from the demodulated second signal that can indicate motion of the implantable lead 1850. In an example, the second signal can be received from the implantable lead 1850. In an example, the second signal can be relatively constant over time (e.g., relatively constant in frequency or in amplitude, among other parameters) for a stationary or immobilized implantable lead 1850 because the impedance of the implantable lead 1850 can remain relatively unchanged at equilibrium. However, as the implantable lead 1850 undergoes movement (or as mechanical vibration is coupled to the lead), the movement of the implantable lead 1850 can modulate or change the impedance of the system containing the one or more conductors in the implantable lead 1850, and the second signal can deviate from its relatively constant amplitude or frequency. For example, a mechanical vibration coupled to the implantable lead 1850 can produce a microphonic effect such as receiving the vibration information by the implantable lead 1850 and providing a second signal in response to the first signal that is analogous to the received vibration. In this example, the mechanical vibration is effectively translated to an analogous electrical signal.

In an example, more than one implantable lead can be included in the ambulatory medical device 2000, as previously described. In this example, the first signal can be provided to the system comprising the multiple implantable leads and the second signal can be received from the same system. In an example, the relative or independent motion of the two or more leads can modulate the impedance of the system comprising the leads. In an example, the additional leads can provide a greater magnitude of impedance modulation of the system comprising the sensing elements, therefore exaggerating the response signal under some circumstances (e.g., using a "differential" measurement of multiple lead impedances or capacitances). Under some other set of circumstances, the impedance modulation of the system comprising the multiple sensing elements may have a nullifying effect on the response signal. In such an example, the implantable leads can be implanted or configured, or the conductors used for sensing can be selected, in such a manner as to create a specified response or sensitivity.

In an example, the demodulated signal can be provided to a signal processor 2030 for further extracting the information indicative of motion of the implantable lead 1850. In an example, the second signal can be high pass filtered to remove the low frequency wall motion and isolate higher frequency blood flow motion information. In this example, the pitch of the resulting signal can be related to the velocity of the blood flow. In an example, a demodulated and filtered signal can be transmitted, such as via an output 2040, to an external assembly, such as for visual or audible presentation to a clinician or care giver, such as using an audio amplifier. In an example, an examiner can listen to the blood flow information or the heart wall motion information provided by the medical device. For example, when the information indicative of motion includes a subsonic or ultrasonic component, such components can be respectively upconverted or downconverted (e.g., adjusted in speed or frequency) for playback using an audible range of frequencies.

Figure 25:
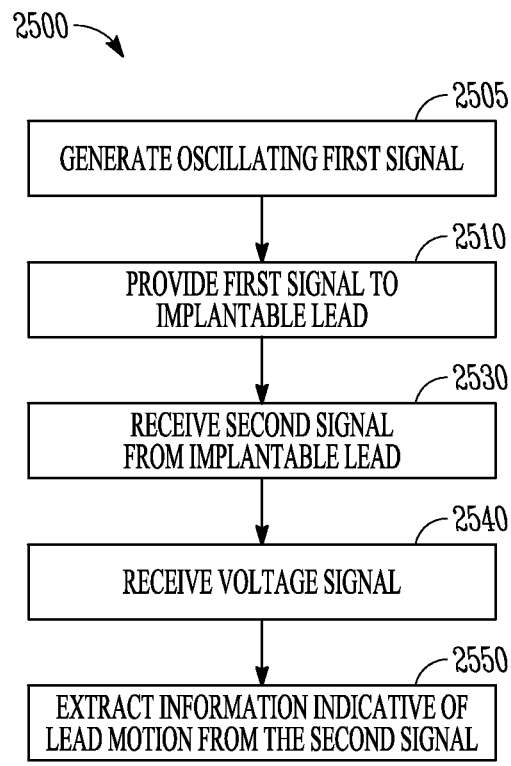
FIG. 25 illustrates generally an example of a portion of a method such as including generating an oscillating first signal, providing the first signal to an implantable lead, receiving a second signal from the implantable lead, receiving a voltage, or extracting information indicative of lead motion from the received voltage.

FIG. 25 illustrates generally an example 2500 that can include generating an oscillating first signal, providing the first signal to an implantable lead, receiving a second signal from the implantable lead, receiving a voltage signal, or extracting information indicative of lead motion from the voltage signal, such as using circuitry or techniques discussed above with respect to FIGS. 18-22.

At 2505, a first signal can be generated by an oscillator circuit included in excitation circuit 1810. In an example, the oscillator circuit can include a Pierce oscillator. In an example, the frequency of oscillation can in part determine the sensitivity of a system 2100. The frequency of the first signal can be specified to correspond to one or more frequencies that exhibit a change in impedance of an implantable lead 1850 at least in part due to motion of the implantable lead 1850.

At 2510, a first signal can be provided to the implantable lead 1850. In an example, the first signal can be an AC signal routed through a bridge circuit 2121. In this example, the implantable lead 1850 can form a portion (e.g., one of the legs) of the bridge circuit 2121. In an example, a capacitive element 2125 forms the leg of the bridge circuit 2121 that is opposite the implantable lead 1850. In an example, positive half cycles of the first signal can charge a first capacitance provided by the implantable lead 1850. In an example, the capacitive element 2125 can act as a second capacitance, which can be charged during negative half cycles of the first signal.

At 2530, a second signal can be received from the implantable lead 1850 wherein the second signal can be a response to the first signal. In an example, the second signal can be a voltage signal indicating a voltage across the first capacitance, and thus a change in capacitance of the implantable lead 1850 can be transformed into a voltage signal. The second signal can be a voltage signal indicating a voltage across the second capacitance.

At 2540, the voltage signal can be received. In an example, a voltage signal indicating a change in capacitance can be received by the envelope detector 2127. In an example, the envelope detector 2127 can be a diode or rectifier detector or a synchronous detector operating at the same frequency as the first signal. In an example, the voltage across the envelope detector 2127 can include a relatively constant value (e.g., amplitude or frequency) when the implantable lead 1850 is at equilibrium. However, when the capacitance of implantable lead 1850 changes, such as during a movement of the implantable lead 1850, the voltage across the envelope detector 2127 can change by an amount proportional to the displacement of the implantable lead 1850, the magnitude of the change in capacitance indicative of displacement.

At 2550, information can be extracted from the envelope detector 2127 that can be indicative of motion of the implantable lead 1850. In an example, a signal can be transmitted to an external source and amplified by an audio amplifier. In an example, an examiner can listen to heart sound information, as discussed above in the example of FIG. 24. In an example, heart wall motion information can be isolated and visually or audibly presented to the examiner (e.g., a clinician or caregiver).

Figure 26:
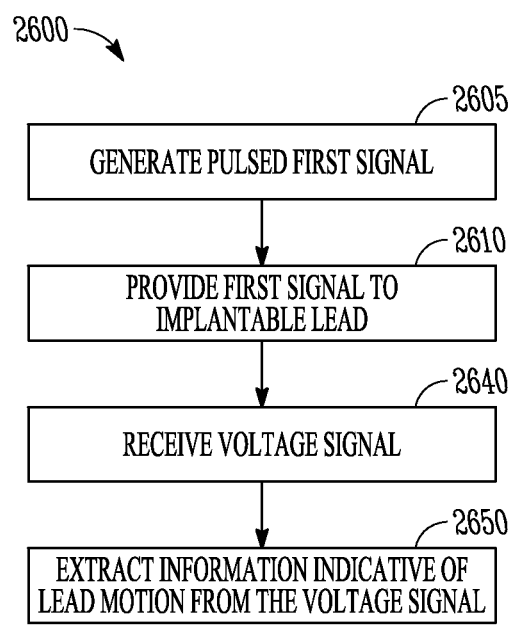
FIG. 26 illustrates generally an example that can include generating a pulsed first signal, providing the first signal to an implantable lead, receiving a voltage, or extracting information indicative of lead motion from the received voltage.

FIG. 26 illustrates generally an example 2600 that can include generating a pulsed first signal, providing the first signal to an implantable lead, receiving a voltage, or extracting information indicative of lead motion, such as using circuitry or techniques discussed above with respect to FIGS. 18-22.

At 2605, a first signal can be generated by a pulse generator. In an example, the pulse generator can produce a sequence of square wave pulses, or pulses having one or more other specified levels, duty cycles, repetition rates, or the like.

At 2610, a first signal can be provided to an implantable lead 1850. In an example, a first signal can be received from the excitation circuit 2210 by the detection circuit 2220. The received first signal can be coupled to the multiplexer 2221 in detection circuit 2220. In an example, the multiplexer 2221 can be coupled to the implantable lead 1850 via the interconnect 2260 and the lead coupling 1870. In an example, the detection circuit 2220 can include a multiplexer 2221 that can control the coupling of the first signal to the implantable lead 1850. The multiplexer 2221 can also be configured to apply a first signal to the capacitive element 2225.

At 2640, a voltage signal can be received. In an example, the multiplexer 2221 can be configured to apply a first signal to the implantable lead 1850 for a specified duration of time. In an example, the voltage signal can include a first voltage measurement of the implantable lead after a specified duration of time. In an example, the multiplexer 2221 can be configured to apply a first signal to the capacitive element 2225 for a specified duration of time (e.g., to charge the capacitive element 2225). The voltage signal can include a second voltage measurement of the capacitive element 2225 after a specified duration of time.

At 2650, information can be extracted from one or more of the first or second voltage signals indicative of motion of an implantable lead 1850. In an example, the voltage signal can be compared to a specified threshold voltage, or one or more voltage signals can be compared to an array of threshold voltages.

Figure 27:
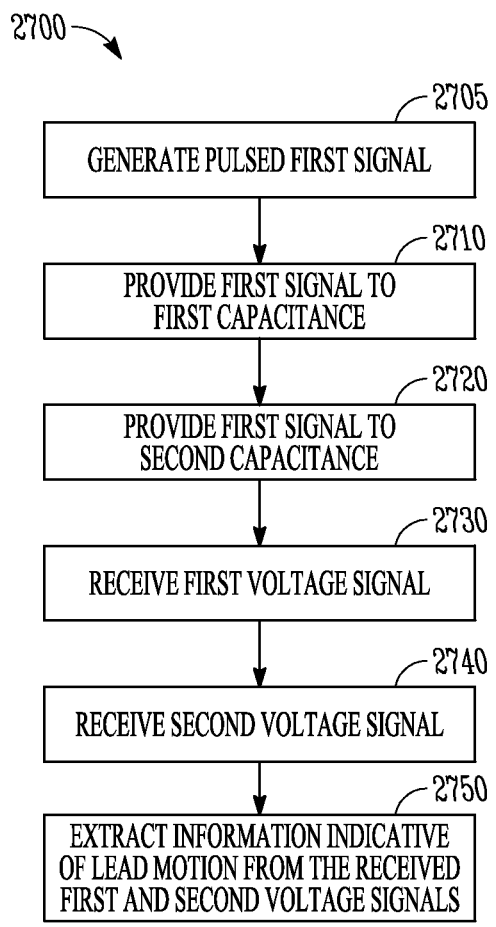
FIG. 27 illustrates generally an example that can include generating a pulsed first signal, providing the first signal to a first capacitance, providing the first signal to a second capacitance, receiving a first voltage, receiving a second voltage, or extracting information indicative of lead motion from the received first and second voltages.

FIG. 27 illustrates generally an example 2700 that can include generating a pulsed first signal, providing the pulsed first signal to a first capacitance, providing the pulsed first signal to a second capacitance, receiving a first voltage, receiving a second voltage, or extracting information indicative of lead motion.

At 2705, a first signal can be generated by a pulse generator. In an example, the pulse generator can produce pulses such as including one or more current or voltage pulses including pulses of a specified amplitude, duty cycle, or morphology, among other parameters.

At 2710, a first signal can be provided to a first capacitance. In an example, the first capacitance can be provided at least in part by the implantable lead 1850. In an example, the first signal can be received from the excitation circuit 2210 by the detection circuit 2220. The received first signal can be coupled to the multiplexer 2221 in the detection circuit 2220. The multiplexer 2221 can be coupled to the implantable lead 1850 via the interconnect 2260 and the lead coupling 1870. In an example, the detection circuit 2220 can operate the multiplexer 2221 to determine when a first signal can be applied to the implantable lead 1850.

At 2720, the first signal can be similarly provided to the second capacitance. For example, the second capacitance can be provided by the capacitive element 2225. In an example, the multiplexer 2221 can be coupled to the capacitive element 2225. In an example, the detection circuit 2220 can operate the multiplexer 2221 to controllably couple the first signal to the second capacitance. The capacitive element 2225 can be a discrete or distributed capacitor or a combination of capacitors providing a specified capacitance value, a second implantable lead, or an array of interconnected implantable leads or conductors, among others.

At 2730, a first voltage signal can be received. The first voltage signal can be a signal in response to the first signal. In an example, the first voltage signal can indicate, among other things, a charge level of the first capacitance or a first count of a number of pulses provided by the first signal.

At 2740, the second voltage signal can be received. The second voltage signal can be a signal in response to the first signal. In an example, the second voltage signal can indicate, among other things, a charge level of the second capacitance or a second count of a number of pulses provided by the first signal.

At 2750, information can be extracted from the first and second voltage signals indicative of motion of the implantable lead 1850. In an example, the first and second voltage signals can represent, respectively, a duration of respective first and second capacitor charge times. In this example, the first charge time can include an interval wherein the voltage across the first capacitance is between a lower voltage threshold and an upper voltage threshold. Similarly, the second charge time can include an interval wherein the voltage across the second capacitance is between the lower and upper voltage thresholds. In an example, information indicative of lead motion can be extracted by determining a relative indication of the first and second durations. For example, the first duration can be measured to be greater or lesser than the second duration. For example, the difference between the first and second durations can indicate the magnitude of the displacement of the implantable lead 1850, wherein the displacement causes a change in the first capacitance. In an example, when the first and second duration of a charge time are approximately equivalent, the relative indication of information can indicate that the implantable lead 1850 is stationary or otherwise at equilibrium.

In an example, the first voltage signal can represent a first count of a number a pulses provided to the first capacitance. Similarly, the second voltage signal can represent a second count of a number of pulses provided to the second capacitance. In an example, information indicative of lead motion can be extracted by determining a relative indication of the first and second counts. For example, the difference between the first and second counts can indicate the magnitude of the displacement of the implantable lead 1850, wherein the displacement causes a change in the first capacitance. In an example, when the first and second counts are approximately equivalent or unchanging, the relative indication of information can indicate that the implantable lead 1850 is stationary or otherwise at equilibrium.

Figure 28:
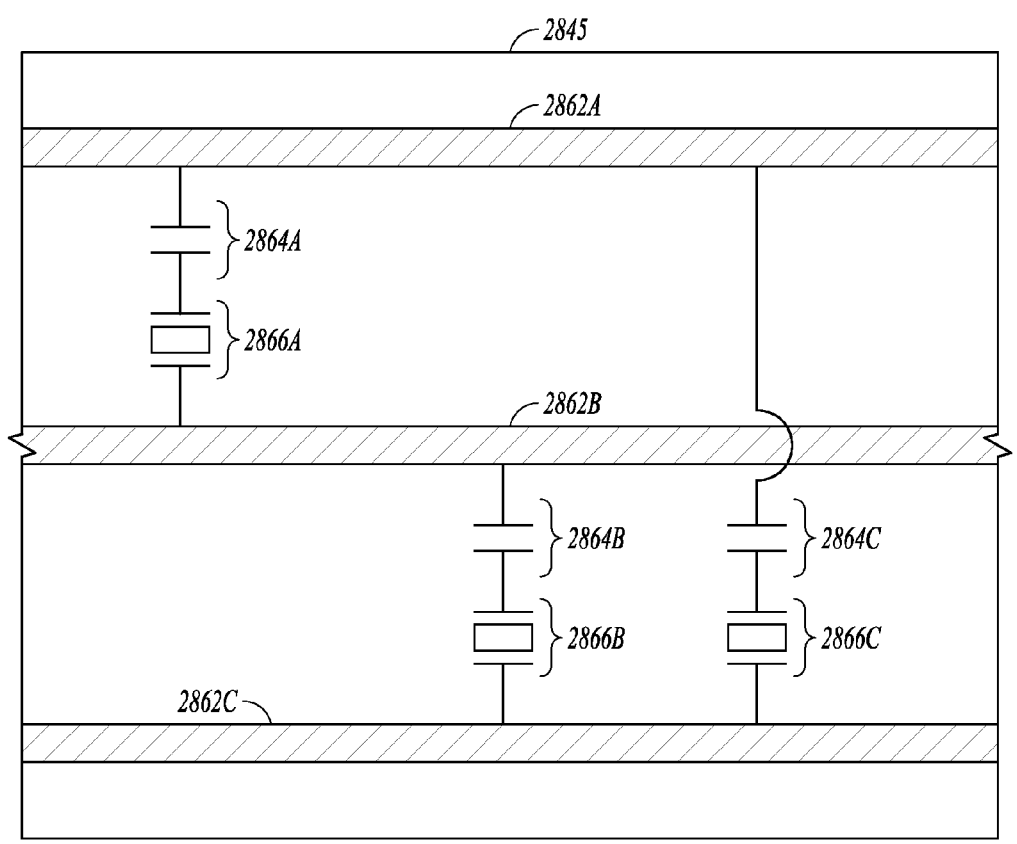
FIG. 28 illustrates generally an example of a portion of an implantable lead assembly that can include one or more transducers.

FIG. 28 illustrates generally an example of a portion of an implantable lead assembly 2845 that can include one or more piezoelectric transducers. In the example of FIG. 28, the implantable lead can include a first conductor 2862A, a second conductor 2862B, or a third conductor 2862C. A first transducer 2866A can be located on or within the lead assembly 2845, such as electrically coupled between the first conductor 2862A and the second conductor 2862B, such as including a first series capacitor 2864A (e.g., a DC-blocking capacitor). Similarly, a second transducer 2866B can be electrically coupled between the second conductor 2862B and the third conductor 2862C, such as via a second series capacitor 2864B. A third transducer 2866C can be electrically coupled between the first conductor 2862A and the third conductor 2862C, such as via a third series capacitor 2864C. Thus, in the example of FIG. 28, one or more of the transducers 2866A-C can be sampled or addressed via measurement or stimulation of a desired conductor pair (e.g., first and third conductors 2862A,C to address the third transducer 2866C, etc.).

In an example, one or more of the transducers 2866A-C can be excited such as to convert a non-therapeutic, non-stimulating electrical signal into acoustic energy (e.g., to provide acoustic energy such as ultrasonic energy). Conversely, one or more of the transducers 2866A-C can be configured for one or more of passive reception of acoustic energy (or mechanical vibration), or for reception of the acoustic transmission provided by another transducer, or the transducer being excited can modulate the excitation signal in response to received mechanical or acoustic energy. One or more of the conductors 2862A-C can be therapy delivery or cardiac electrical activity sensing conductors (e.g., the lead assembly 2845 need not carry extra conductors dedicated for use by the one or more transducers 2866A-C).

One or more of the transducers 2866A-C can include a piezoelectric construction, such as including metal or other conductive materials coupled to a lead-zirconate titanate material (PZT) piezoelectric material or coupled to a polyvinylidene fluoride (PVDF) piezoelectric material. For example, one or more of transducers 2866A-C can be used to measure blood velocity or other physiologic velocities relative to the transducer location, such as using a Doppler technique (e.g., a continuous-wave Doppler flow measurement). For example, a flow signal obtained using such techniques can include a high-frequency portion corresponding to the moving blood, a low frequency portion corresponding to heart wall motion, and a near-DC component such as corresponding to phase noise of an oscillator used to excite the transducer.

In an example, acoustic transmissions can be made between one of the transducers 2866A-C and another one of the transducers 2866A-C, such as to obtain information about a distance between various transducers 2866A-C. Such a distance can be determined via measurement of the time-delay between initiating an acoustic transmission at a first location and receiving a corresponding transmission at a second location. Thus, in the example of FIG. 28, such time-of-flight measurements can provide independent information about three different distances (e.g., between pairs of transducers 2866A-C, or between one or more of the transducers 2866A-C and another acoustic transmitter or receiver elsewhere), which can be tracked to reveal relative changes in displacement of portions of the implantable lead 2845. Multipath or other errors can be controlled or reduced such as by time-gating the received acoustic energy such as to capture the first (e.g., direct) or other desired time-of-flight between a desired transmit-receive transducer pair.

The selection of piezoelectric materials and operating frequency ranges can include considerations of size or mechanical flexibility, or directivity of resulting acoustic (e.g., ultrasonic) transmission or reception. For example, the frequency can be selected to be high enough that the corresponding acoustic wavelength is small with respect to the dimensions of the transducer, providing more omni-directional transmission or reception of acoustic energy.

In an example, the one or more transducers 2866A-C can be addressed using a frequency-selective technique. For example, a resonant device such as a thickness-mode PZT device can be excited with a burst of electrical energy corresponding to the PZT device's resonant frequency. Two or more transducers can be placed parallel to each other electrically, such as at specified locations along the implantable lead assembly 2845, such as including staggered or offset resonant frequencies, such as to provide spatially-addressable transducers that can be addressed using a desired frequency range corresponding to the resonant of a desired transducer at a specified location.

In an example, one or more of the transducers 2866A-C need not be resonant. For example, non-resonant PVDF transducers can be used interchangeably for transmission or reception of acoustic energy. In an example, a narrow-band PZT transmitting transducer can be used, and a broadband PVDF receiving transducer can be used. In this manner, the PVDF receiver need not be carefully matched or tuned to the PZT transmitter.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus including an implantable medical device (IMD), the IMD including:
   an excitation circuit configured to provide a non-tissue stimulating, non-therapeutic electrical excitation signal to a conductor comprising a portion of an implantable lead, the excitation signal comprising a time-varying signal including a first range of frequencies;
   a receiver circuit electrically coupled to the conductor, the receiver circuit configured to receive, in response to the excitation signal, a response signal modulated according to a change in an electrical characteristic of the conductor, the response signal including information about the excited conductor itself that is indicative of a mechanical vibration of the implantable lead due at least in part to one or more of impact of at least a portion of a heart to the implantable lead or friction between the implantable lead and cardiac tissue; and
   a processor circuit configured to determine one or more of a lead mechanical status, or information indicative of valvular activity, using the information about the excited conductor itself that is indicative of the mechanical vibration of the implantable lead.

2. The apparatus of claim 1, wherein the processor circuit is configured to determine the lead mechanical status using the information indicative of the mechanical vibration of the implantable lead.

3. The apparatus of claim 1, wherein the processor circuit is configured to determine the information indicative of valvular activity using the information indicative of the mechanical vibration of the implantable lead.

4. The apparatus of claim 1, wherein the processor is configured to obtain frequency components including or above an audio frequency range, the frequency components including energy corresponding to impact or frictional contact of the implantable lead with at least a portion of the heart.

5. The apparatus of claim 1, wherein the processor is configured to determine the lead mechanical status including one or more of lead fault information or lead maturity information.

6. The apparatus of claim 5, wherein the lead fault information comprises a lead dislodgement indication, including information indicative of a partial dislodgement or information indicative of a full dislodgement, determined at least in part using the information indicative of the mechanical vibration of the implantable lead to determine information about a connection of the implantable lead to at least a portion of the heart.

7. The apparatus of claim 1, wherein the information indicative of valvular activity comprises information indicative of a mechanical vibration of a heart valve, the mechanical vibration of the heart valve coupled to the implantable lead when the implantable lead is located within or near the heart.

8. The apparatus of claim 7, wherein the mechanical vibration of the heart valve comprises information indicative of a valve impacting the implantable lead within the heart, including information indicative of at least one of valve closure, or valve opening.

9. The apparatus of claim 7, comprising a heart sound sensing circuit, the heart sound sensing circuit configured to determine heart sound information using the information indicative of the mechanical vibration of a heart valve.

10. The apparatus of claim 9, wherein the heart sound sensing circuit is configured to determine heart sound information using information indicative of radial compression of at least a portion of the implantable lead, the compression correlative to blood pressure.

11. The apparatus of claim 1, further comprising the implantable lead, wherein the implantable lead is configured to be located within or near the heart, and wherein the implantable lead comprises a piezoelectric acoustic transducer configured to receive acoustic information indicative of the mechanical vibration of the implantable lead, the piezoelectric acoustic transducer coupled to the conductor included in the implantable lead.

12. The apparatus of claim 11, further comprising the conductor, wherein the conductor comprises one or more of a cardiac therapy delivery conductor or a cardiac electrical activity sensing conductor, the conductor configured to be coupled to an implantable electrode included as a portion of the implantable lead.

13. The apparatus of claim 1, wherein the information indicative of the mechanical vibration of the implantable lead includes one or more of magnitude information, or phase information, corresponding to one or more frequencies included in the first range of frequencies, the magnitude information, or phase information, determined at least in part using an electrical response signal provided by the implantable lead in response to the excitation signal and the mechanical vibration of the implantable lead.

14. The apparatus of claim 13, wherein one or more of the magnitude information, or the phase information, includes a time-varying portion corresponding to the mechanical vibration of the implantable lead.

15. The apparatus of claim 1, further comprising the implantable lead including the conductor, the implantable lead configured to be located within or near the heart.

16. A processor-readable medium comprising instructions that, when performed by a processor, cause the processor to:
   provide a non-tissue stimulating, non-therapeutic electrical excitation signal to a conductor comprising a portion of an implantable lead, the excitation signal comprising a time-varying signal including a first range of frequencies;
   receive, in response to the excitation signal, a response signal modulated according to a change in an electrical characteristic of the conductor, the response signal including information about the excited conductor itself that is indicative of a mechanical vibration of the implantable lead due at least in part to one or more of impact of at least a portion of a heart with the implantable lead or friction between the implantable lead and cardiac tissue; and determine one or more of a lead mechanical status, or information indicative of valvular activity using the information about the excited conductor itself that is indicative of the mechanical vibration of the implantable lead.

17. The processor-readable medium of claim 16, comprising instructions that, when performed by the processor, cause the processor to obtain frequency components including or above an audio frequency range, the frequency components including energy corresponding to impact or frictional contact of the implantable lead with at least a portion of the heart.

18. The processor-readable medium of claim 16, wherein the instructions to determine the lead mechanical status include instructions to determine one or more of lead fault information or lead maturity information.

19. The processor-readable medium of claim 16, comprising instructions that, when performed by the processor, cause the processor to determine heart sound information using the information indicative of the mechanical vibration of the implantable lead.

20. The processor-readable medium of claim 19, wherein the instructions to determine heart sound information include instructions to use information indicative radial compression on at least a portion of the implantable lead, the compression corresponding to a blood pressure when the implantable lead is located in or near a blood vessel.

21. A system, comprising:

a means for providing a non-tissue stimulating, non-therapeutic electrical excitation signal to a conductor comprising a portion of an implantable lead, the excitation signal comprising a time-varying signal including a first range of frequencies;

a means for receiving, in response to the excitation signal, a response signal modulated according to a change in an electrical characteristic of the conductor, the response signal including information about the excited conductor itself that is indicative of a mechanical vibration of the implantable lead due at least in part to one or more of impact of at least a portion of a heart with the implantable lead or friction between the implantable lead and cardiac tissue; and a means for detecting one or more of a lead mechanical status, or information indicative of valvular activity using the information about the excited conductor itself that is indicative of the mechanical vibration of the implantable lead.

* * * * *